(12) United States Patent
Goldberg et al.

(10) Patent No.: US 7,718,652 B2
(45) Date of Patent: May 18, 2010

(54) SUBSTITUTED BENZOTHIADIAZINEDIOXIDE DERIVATIVES AND METHODS OF THEIR USE

(75) Inventors: Joel Adam Goldberg, Philadelphia, PA (US); Andrew Fensome, Wayne, PA (US); Casey Cameron McComas, Pheonixville, PA (US); Puwen Zhang, Audubon, PA (US)

(73) Assignee: Wyeth LLC, Madison, NJ (US)

( * ) Notice: Subject to any disclaimer, the term of this patent is extended or adjusted under 35 U.S.C. 154(b) by 404 days.

(21) Appl. No.: 11/955,004

(22) Filed: Dec. 12, 2007

(65) Prior Publication Data

US 2008/0161295 A1 Jul. 3, 2008

Related U.S. Application Data

(60) Provisional application No. 60/869,643, filed on Dec. 12, 2006.

(51) Int. Cl.
*C07D 285/16* (2006.01)
*A61K 31/5415* (2006.01)
(52) U.S. Cl. ..................... 514/222.8; 544/11
(58) Field of Classification Search ................... 544/11; 514/222.8
See application file for complete search history.

(56) References Cited

U.S. PATENT DOCUMENTS

| 3,041,336 | A | 6/1962 | Teufel |
| 3,763,209 | A | 10/1973 | Abildgaard |
| 2006/0014764 | A1 | 1/2006 | Feng et al. |

FOREIGN PATENT DOCUMENTS

| EP | 897921 A1 | 2/1999 |
| GB | 879 592 A | 10/1961 |
| GB | 2362381 A | 11/2001 |
| JP | 58-55482 | 4/1983 |
| WO | WO 00/31074 A2 | 6/2000 |
| WO | WO 00/68216 A1 | 11/2000 |
| WO | WO 2002/085291 A2 | 10/2002 |
| WO | WO 03/070709 A1 | 8/2003 |
| WO | WO 2005/046696 A1 | 5/2005 |
| WO | WO 2005/067933 A1 | 7/2005 |

OTHER PUBLICATIONS

Goehring, R. et al., "1,3-Dihydro-2,1,3-benzothiadiazol-2,2-diones and 3,4-dihydro-1*H*-2,1,3-benzothidiazin-2,2-diones as ligands for the NOP receptor," Bioorganic & Medicinal Chemistry Letters 14 (2004) pp. 5045-5050.
Mewshaw, R. et al., "Bridged γ-Carbolines and Derivatives Possessing Selective and Combined Affinity for 5-HT$_2$ and D$_2$ Receptors,"Journal Med. Chem. (1993), 36, pp. 1488-1495.
Clark, J. et al., "The Synthesis of OrganofluorineCompounds Using Potassium Fluoride-Tetraphenylphosphonium Bromide Systems", Tetrahedron Letters, (1987) 28, pp. 111-114.
Hazard, R. et al., "No. 126.—Obtention, par voie électrochimique, d'hétérocycles azotés à partir d' o-nitrosobenzènes substitutés. I.—Oxydation d' o-hydroxylaminobenzylamines. Préparation de quelques indazoles." Bull. Soc. Chim. FR., (1975) pp. 679-685.
Drayton, C. et al., "Polyfluorocarbanion Chemistry. Part III.[1,2] Reaction of Hexafluoro-propene with Pentafluorobenzonitrile", J. Chem. Soc. Perkins Trans. 1, (1975) pp. 1035-1040.
Okawa, H., et al., "Macro Chelate Rings. III.[*1] Syntheses and Configurations of Complexes of New Ligands, 4,4'-Dimethy1-2,2'-bis-(salicylideneaminomethyl)-diphenyl Ether and 4,4'-dimethyl-2,2'bis(salicylidene-aminomethyl)diphenylamine", Bulletin of the Chemical Society of Japan, 43, (1970) pp. 1729-1733.

*Primary Examiner*—Kahsay T Habte
(74) *Attorney, Agent, or Firm*—Doina G. Ene

(57) ABSTRACT

The present invention is directed to substituted benzothiadiazinedioxide derivatives of formula I:

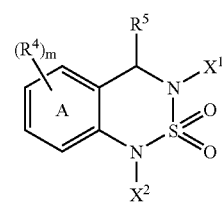

or a pharmaceutically acceptable salt, stereoisomer or tautomer thereof, which are monoamine reuptake inhibitors, compositions containing these derivatives, and methods of their use for the prevention and treatment of conditions, including, inter alia, vasomotor symptoms, sexual dysfunction, gastrointestinal disorders and genitourinary disorder, depression disorders, endogenous behavioral disorders, cognitive disorders, diabetic neuropathy, pain, and other diseases or disorders.

68 Claims, No Drawings

SUBSTITUTED BENZOTHIADIAZINEDIOXIDE DERIVATIVES AND METHODS OF THEIR USE

CROSS-REFERENCE TO RELATED APPLICATIONS

This application claims the benefit under 35 U.S.C. §119 (e) to U.S. Provisional Application Ser. No. 60/869,643, filed Dec. 12, 2006, which is hereby incorporated by reference in its entirety.

FIELD

The present invention relates to substituted benzothiadiazinedioxide derivatives, which are monoamine reuptake inhibitors, compositions containing these derivatives, and methods of their use for the prevention and treatment of diseases or disorders including vasomotor symptoms, depression disorders, endogenous behavioral disorders, cognitive disorders, sexual dysfunction, or pain conditions, in particular vasomotor symptoms.

BACKGROUND

Vasomotor symptoms (VMS), referred to as hot flushes and night sweats, are the most common symptoms associated with menopause, occurring in 60% to 80% of all women following natural or surgically-induced menopause. VMS are likely an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women.

VMS are caused by fluctuations of sex steroid levels and can be disruptive and disabling in both males and females. A hot flush can last up to thirty minutes and vary in their frequency from several times a week to multiple occurrences per day. The patient experiences a hot flush as a sudden feeling of heat that spreads quickly from the face to the chest and back and then over the rest of the body. It is usually accompanied by outbreaks of profuse sweating, and may sometimes occur several times an hour, and it often occurs at night. Hot flushes and outbreaks of sweats occurring during the night can cause sleep deprivation. Psychological and emotional symptoms are also observed, such as nervousness, fatigue, irritability, insomnia, depression, memory loss, headache, anxiety, nervousness or inability to concentrate, and are caused by the sleep deprivation following hot flush and night sweats (Kramer et al., In: Murphy et al., 3$^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons. Many survivors of breast cancer are given tamoxifen, the most prevalent side effect of which is hot flush, and many women treated for breast cancer undergo premature menopause from chemotherapy. Women with a history of breast cancer are also generally been denied estrogen therapy because of concerns about potential recurrence of breast cancer (Loprinzi, et al., Lancet, 2000, 356 (9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these vasomotor symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within Loprinzi, et al., were used to support the claims that the norepinephrine system could be targeted to treat VMS.

Although VMS are most commonly treated by hormone therapy, some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flushes, including steroids, alpha-adrenergic agonists, and beta-blockers, with varying degree of success (Waldinger et al., Maturitas, 2000, 36(3): 165-168).

$\alpha_2$-Adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the $_{\alpha2}$-adrenergic receptors, $\alpha_{2A}$, $\alpha_{2B}$, $\alpha_{2C}$ and $\alpha_{2D}$ (Mackinnon et al., TIPS, 1994, 15: 119; French, Pharmacol. Ther., 1995, 68: 175). A non-select $\alpha_2$-adrenoceptor antagonist, yohimbine, induces a flush and an $\alpha_2$-adrenergic receptor agonist, clonidine, alleviates the yohimbine effect (Katovich, et al., Proceedings of the Society for Experimental Biology & Medicine, 1990, 193(2): 129-35, Freedman et al., Fertility &

Sterility, 2000, 74(1): 20-3). Clonidine has been used to treat hot flush. However, using such treatment is associated with a number of undesired side effects caused by high doses necessary to abate hot flush described herein and known in the related arts.

Chronic pain comes in many forms, including visceral, inflammatory or neuropathic and crosses all therapeutic areas. It is a debilitating condition that exerts a high social cost in terms of productivity, economic impact and quality of life and current therapies have limited efficacy. Currently, first-line pharmacological treatments for neuropathic pain (i.e., diabetic neuropathy and post-herpetic neuralgia) and fibromyalgia include off-label use of the tricyclic (TCA) antidepressants (e.g., amytriptyline) and anticonvulsants (e.g., gabapentin) (Collins et al., *J. Pain Symptom Manage.* 2000, 20(6):449-58; and Marcus *Expert Opin Pharmacother.* 2003, 4(10): 1687-95). However, these therapies are only effective in 30-50% of patients and produce only a partial reduction in pain (~50%). In addition, the clinical benefits of these therapies are often outweighed by the side effects, including dry mouth and sedation. Therefore, newer classes of compounds including non-TCA antidepressants are being evaluated preclinically and clinically for chronic pain indications, and recently duloxetine was approved for the treatment of diabetic neuropathy. Although more tolerable than the older tricyclic antidepressants, these newer compounds are not devoid of side effects that include sexual dysfunction, weight gain and nausea.

While the precise pathophysiological mechanisms involved in the development and maintenance of chronic pain states are not fully understood, the pathways involved in pain perception and modulation have been well described and characterized (Gebhart, In: Yaksh T L, editor. Spinal afferent processing, New York: Plenum, 1986. pp 391-416; Fields, et al., *Annual Review of Neuroscience* 1991, 14: 219-245; Fields, et al. In: Wall P D, Melzack R, editors. Textbook of pain, London: Churchill Livingstone, 1999, pp 309-329; Millan, et al. *Progress in Neurobiology;* 2002, 66:355-474). A major component of this descending pain inhibitory system involves the noradrenergic pathway (Zhuo, et al., *Brain Research* 1991; 550:35-48; Holden, et al. *Neuroscience* 1999; 91: 979-990). It is assumed that norepinephrine (NE), and to a lesser extent serotonin (5-HT) reuptake inhibitor NRIs and SRIs, attenuate pain by preventing presynaptic reuptake of NE/5-HT leading to increased postsynaptic NE/5-HT levels and sustained activation of this descending pain inhibitory pathway. A meta-analysis of antidepressants and neuropathic pain comparing the efficacy of known NRIs, mixed NRI/SRIs and SRIs determined that compounds with NRI activity were more effective in reducing pain, and that select SRIs did not significantly differ from placebo (Collins et al., *J. Pain Symptom Manage.* 2000, 20(6): 449-58). This analysis suggests that compounds with greater NRI versus SRI activity will be more effective for the treatment of pain.

Given the complex multifaceted nature of pain and of thermoregulation and the interplay between the CNS and PNS in maintaining thermoregulatory the homeostasis, multiple therapies and approaches can be developed to target the treatment of pain and vasomotor symptoms. The present invention provides novel compounds and compositions containing these compounds directed to these and other important uses.

SUMMARY

The present invention is directed to cyclic sulfonamide derivatives, which are monoamine reuptake inhibitors, compositions containing these derivatives, and methods of their use for the prevention and treatment of conditions, including, inter alia, vasomotor symptoms (such as hot flush), sexual dysfunction (such as desire-related or arousal-related dysfunction), gastrointestinal disorders and genitourinary disorder (such as stress incontinence or urge incontinence), chronic fatigue syndrome, fibromyalgia syndrome, depression disorders (such as major depressive disorder, generalized anxiety disorder, panic disorder, attention deficit disorder with or without hyperactivity, sleep disturbance, and social phobia), diabetic neuropathy, pain, and combinations thereof.

In one aspect, the present invention is directed to compounds of formula I:

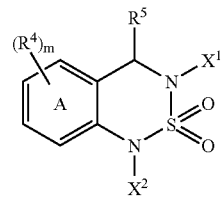

I or a pharmaceutically acceptable salt, tautomer or stereoisomer thereof;

wherein:

n is an integer from 0 to 3;

m is an integer from 0 to 4;

$X^1$ is $R^1$ and $X^2$ is W; or $X^1$ is W and $X^2$ is $R^1$;

W is:

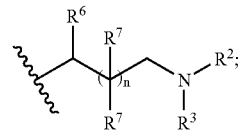

$R^1$ is aryl substituted with 0-3 $R^{11}$ or heteroaryl substituted with 0-3 $R^{11}$;

$R^2$ is H, $C_1$-$C_6$ alkyl, $C_3$-$C_6$ cycloalkyl, $C_2$-$C_6$ alkanol, or aryl-$C_1$-$C_6$ alkyl, where said aryl portion is substituted with 0-3 $R^{12}$ and said alkyl portions may be substituted with 0-3 $R^{13}$;

$R^3$ is H, $C_1$-$C_6$ alkyl, $C_3$-$C_6$ cycloalkyl, $C_2$-$C_6$ alkanol or aryl-$C_1$-$C_6$ alkyl where said aryl portion is substituted with 0-3 $R^{12}$ and said alkyl portions may be substituted with 0-3 $R^{13}$; or $R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;

$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;

$R^5$ is H, $C_1$-$C_6$ alkyl, $C_6$-$C_{10}$ aryl substituted with 0-3 $R^{15}$, $C_6$-$C_{10}$ aryl-$C_1$-$C_6$ alkyl where said aryl portion is substituted with 0-3 $R^{15}$, heteroaryl substituted with 0-3

$R^{15}$, or heteroaryl-$C_1$-$C_6$ alkyl where said heteroaryl portion is substituted with 0-3 $R^{15}$;

$R^6$ is H, $C_1$-$C_6$ alkyl, aryl substituted with 0-3 $R^{16}$, aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, aryl, heteroaryl, alkylsulfoxide, alkylsulfone, alkylsulfonamide, arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N.

In another aspect, the present invention is directed to compounds of formula II:

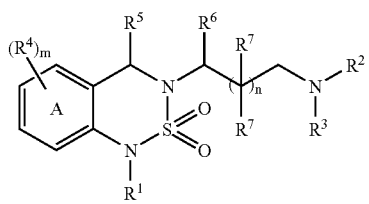

II wherein in the variables are the same as defined for the compound of formula I.

In another aspect, the present invention is directed to compounds of formula III:

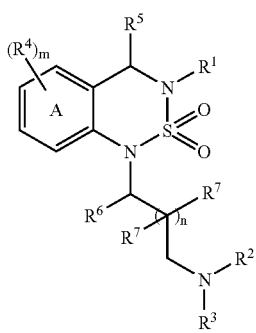

III wherein in the variables are the same as defined for the compound of formula I.

In yet other embodiments, the present invention is directed to compositions, comprising:

a. at least one compound of formula I, II or III; and b. at least one pharmaceutically acceptable carrier.

In another embodiment, the invention is directed to methods for treating or preventing a condition selected from the group consisting of a vasomotor symptom, sexual dysfunction, gastrointestinal disorder, genitourinary disorder, chronic fatigue syndrome, fibromyalgia syndrome, depression disorder, diabetic neuropathy, pain, and combinations thereof in a subject in need thereof, comprising the step of:

administering to said subject an effective amount of a compound of formula I, II or III or pharmaceutically acceptable salt thereof.

DETAILED DESCRIPTION

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value" means dose which results in 50% alleviation of the observed condition or effect (50% mean maximum endpoint).

"Norepinephrine transporter" is abbreviated NET.

"Human norepinephrine transporter" is abbreviated hNET.

"Serotonin transporter" is abbreviated SERT.

"Human serotonin transporter" is abbreviated hSERT.

"Norepinephrine reuptake inhibitor" is abbreviated NRI.

"Selective norepinephrine reuptake inhibitor" is abbreviated SNRI.

"Serotonin reuptake inhibitor" is abbreviated SRI.

"Selective serotonin reuptake inhibitor" is abbreviated SSRI.

"Norepinephrine" is abbreviated NE.

"Serotonin is abbreviated 5-HT.

"Subcutaneous" is abbreviated sc.

"Intraperitoneal" is abbreviated ip.

"Oral" is abbreviated po.

In the context of this disclosure, a number of terms are utilized. The term "treat," "treatment" or "treating" as used herein includes preventative (e.g., prophylactic), curative or palliative treatment.

The term "effective amount," as used herein, refers to an amount effective, at dosages, and for periods of time necessary, to achieve the desired result with respect to treatment of a given disease or disorder. An effective amount is also one in which any toxic or detrimental effects of the components are outweighed by the therapeutically beneficial effects. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

The effective amount of components of the present invention will vary from patient to patient not only with the particular compound, component or composition selected, the route of administration, and the ability of the components (alone or in combination with one or more additional active agents) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to sexual dysfunction, gastrointestinal disorder, genitourinary disorder, chronic fatigue syndrome, fibromyalgia syndrome, depression disorder, diabetic neuropathy, or pain, the compounds of the present invention are administered at a dosage and for a time sufficient to treat the symptom or condition.

For example, for a patient, compounds of formula I, II, or III, or a pharmaceutically acceptable salt thereof, may be administered, preferably, at a dosage of from about 0.1 mg/day to about 1500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the sexual dysfunction, gastrointestinal disorder, genitourinary disorder, chronic fatigue syndrome, fibromyalgia syndrome, depression disorder, diabetic neuropathy, or pain.

The terms "component," "composition," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound; e.g., antibody, small molecule, peptide, oligopeptide, polypeptide, or protein, and is preferably small molecule or peptide.

As used herein, the term "inhibitor" refers to any agent that inhibits, suppresses, represses, or decreases a specific activity, such as norepinephrine reuptake activity. The term "inhibitor" is intended to comprise any compound, e.g., antibody, small molecule, peptide, oligopeptide, polypeptide, or protein (preferably small molecule or peptide) that exhibits a partial, complete, competitive and/or inhibitory effect on mammalian (preferably human norepinephrine reuptake or both serotonin reuptake and norepinephrine reuptake) thus diminishing or blocking (preferably diminishing) some or all of the biological effects of endogenous norepinephrine reuptake or of both serotonin reuptake and the norepinephrine reuptake.

Within the present invention, the compounds of formula I, II or III may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferred is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compounds, compositions, and/or methods of the present invention. The term "subject" or "subjects" is intended to refer to both the male and female gender unless one gender is specifically indicated. Accordingly, the term "patient" comprises any mammal which may benefit from treatment or prevention of a disease or disorder such as a human, especially if the mammal is female, either in the pre-menopausal, peri-menopausal, or post-menopausal period. Furthermore, the term "patient" includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

"Side effect" refers to a consequence other than the one(s) for which an agent or measure is used, as one or more adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and hot flushes (Janowsky, et al., *Journal of Clinical Psychiatry*, 1984, 45(10 Pt 2): 3-9).

"Vasomotor symptoms" (also called "vasomotor instability symptoms" and "vasomotor disturbances") include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" (sometimes called "hot flash") is an art-recognized term that refers to an episodic disturbance in body temperature typically consisting of a sudden skin flushing, usually accompanied by perspiration in a subject.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

The term "sexual dysfunction" includes, but is not limited to, conditions relating to disorders of sexual desire and/or arousal.

As used herein, "gastrointestinal and genitourinary disorders" includes irritable bowel syndrome, symptomatic GERD, hypersensitive esophagus, nonulcer dyspepsia, non-cardiac chest pain, biliary dyskinesia, sphincter of Oddi dysfunction, incontinence (i.e., urge incontinence, stress incontinence, genuine stress incontinence, and mixed incontinence, including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof, whether or not correlated with Epstein-Barr virus infection.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, the term "depression disorder" includes major depressive disorder, generalized anxiety disorder, panic disorder, attention deficit disorder with or without hyperactivity, sleep disturbance, social phobia, and combinations thereof.

The compounds of the present invention can also be used to treat a cognitive disorder or an endogenous behavioral disorder. As used herein, a "cognitive disorder" includes changes or defects in alertness; mild cognitive impairment (MCI), characterized by problems with memory, language, or other mental functions which is severe enough to be noticeable or be detected by tests, but not serious enough to significantly interfere with daily life; cognitive disorder NOS (not otherwise specified), characterized by a syndrome of cognitive impairment that does not meet the criteria for delerium, dementia or amnesic disorders; age-related cognitive decline (ARCD); and cognitive arousal (such as increased arousal states). A cognition disorder can be ideopathic, or can be caused by a variety of other factors such as a congenital defect, alcohol or drug addiction, transient or permanent pharmacologic effects of drugs, organic or infectious disease (e.g., Alzheimer's disease, Parkinson's disease, AIDS), trauma (e.g., brain injury, stroke) or advanced age. As used herein, an "endogenous behavioral disorder" includes attention deficit disorder/attention deficit hyperactivity disorder (ADD/ADHD, including adult and pediatric forms of predominantly inattentive, predominantly hyperactive, or combined types), obsessive-compulsive disorder (OCD), oppositional or oppositional explosive defiant disorder (ODD/OEDD), anxiety and panic disorders (APD) and temper, rage and outburst behavior disorder (TROBD).

As used herein, the term "pain" includes both acute and chronic nociceptic or neuropathic pain, which includes centralized pain, peripheral pain, or combination thereof. The term includes many different types of pain including, but not limited to, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purposes of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. A branched alkyl group has at least 3 carbon atoms (e.g., an isopropyl group), and in various embodiments, has up to 6 carbon atoms, i.e., a branched lower alkyl group. A branched alkyl group has at least 3 carbon atoms (e.g., an isopropyl group), and in various embodiments, has up to 6 carbon atoms, i.e., a branched lower alkyl group. Examples of branched lower alkyl groups include, but are not limited to:

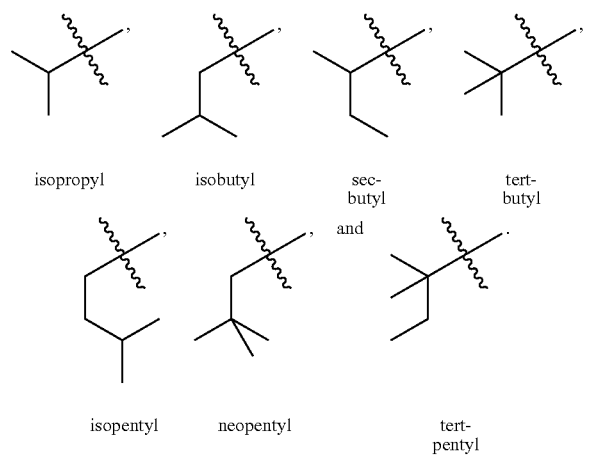

"Alkenyl," as used herein, refers to an alkyl group of at least two carbon atoms having one or more double bonds, wherein alkyl is as defined herein. Alkenyl groups can be optionally substituted. Preferably, alkenyl groups have two to six carbon atoms ("$C_2$-$C_6$ alkenyl").

"Alkynyl," as used herein, refers to an alkyl group of at least two carbon atoms having one or more triple bonds, wherein alkyl is as defined herein. Alkynyl groups can be optionally substituted. Preferably, alkynyl groups have two to six carbon atoms ("$C_2$-$C_6$ alkynyl").

"Alkylenyl", "alkenylenyl", "alkynylenyl", and "arylenyl" refer to the subsets of alkyl, alkenyl, alkynyl and aryl groups, respectively, as defined herein, including the same residues as alkyl, alkenyl, alkynyl, and aryl but having two points of attachment within a chemical structure. Examples of $C_1$-$C_6$alkylenyl include methylenyl (—$CH_2$—), ethylenyl (—$CH_2CH_2$—), propylenyl (—$CH_2CH_2CH_2$—), and dimethylpropylenyl (—$CH_2C(CH_3)_2CH_2$—). Likewise, examples of $C_2$-$C_6$alkenylenyl include ethenylenyl (—CH=CH— and propenylenyl (—CH=CH—$CH_2$—). Examples of $C_2$-$C_6$alkynylenyl include ethynylenyl (—C≡C—) and propynylenyl (—C≡C—$CH_2$—). Examples of arylenyl groups include phenylenyl;

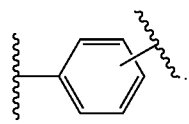

Preferably, arylenyl groups contain 6 carbon atoms ($C_6$).

"Halo," as used herein, refers to chloro, bromo, fluoro, and iodo.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred ($C_6$-$C_{10}$ aryl). Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 4- to 12-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than two. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Alkoxy," as used herein, refers to the group R—O— where R is an alkyl group as defined herein. Preferably, alkoxy groups have from 1 to 6 carbon atoms ($C_1$-$C_6$ alkoxy).

"Alkanoyloxy," as used herein, refers to the group R—C(=O)—O— where R is an alkyl group of 1 to 5 carbon atoms.

"Alkylsulfoxide," as used herein, refers to as used herein, refers to S(=O)—R, where R is alkyl, as defined above.

"Alkylsulfone," as used herein, refers to —S(=O)$_2$—R, where R is alkyl, as defined above.

"Alkylsulfonamide," as used herein, refers to —NR—S(=O)$_2$—R, where each R is independently, alkyl, as defined above or the NR part may also be NH.

"Arylsulfonamide," as used herein, refers to —NR—S(=O)$_2$—R', where R is H or alkyl and R' is aryl, as defined above.

"Alkylamido," as used herein, refers to —NR—C(=O)—R, where each R is independently, alkyl, as defined above, or the NR part may also be NH.

"Arylamido," as used herein, refers to —NR—C(=O)—R", where R is H or alkyl, as defined herein, and R" is aryl, as defined herein. Preferred arylamido groups have from 6 to 10 carbon atoms ($C_6$-$C_{10}$).

"Phenylamido," as used herein, refers to —NR—C(=O)-phenyl, where R is H or alkyl, as defined above.

Unless indicated otherwise, the nomenclature of substituents that are not explicitly defined herein are arrived at by naming the terminal portion of the functionality followed by the adjacent functionality toward the point of attachment. For example, the substituent "arylalkoxycarbonyl" refers to the group (aryl)-(alkyl)-O—C(O)—.

It is understood that the above definitions are not intended to include impermissible substitution patterns (e.g., methyl substituted with 5 fluoro groups). Such impermissible substitution patterns are well known to the skilled artisan.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of another example, the term "5-9 membered heteroaryl group" is specifically intended to individually disclose a heteroaryl group having 5, 6, 7, 8, 9, 5-9, 5-8, 5-7, 5-6, 6-9, 6-8, 6-7, 7-9, 7-8, and 8-9 ring atoms.

The term "protecting group" or "$G_p$" with respect to amine groups, hydroxyl groups and sulfhydryl groups refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; carbamates; e.g. BOC; imides, such as phthalimide, Fmoc, Cbz, PMB, benzyl, and dithiosuccinimide; and others. Examples of protected or capped sulfhydryl groups include, but are not limited to, thioethers such as S-benzyl thioether, and S-4-picolyl thioether; substituted S-methyl derivatives such as hemithio, dithio and aminothio acetals; and others.

Reference to "activated" or "an activating group" or "$G_a$" as used herein indicates having an electrophilic moiety bound to a substituent, capable of being displaced by a nucleophile. Examples of preferred activating groups are halogens, such as Cl, Br or I, and F; triflate; mesylate, or tosylate; esters; aldehydes; ketones; epoxides; and the like. An example of an activated group is acetylchloride, which is readily attacked by a nucleophile, such as piperidine group to form a N-acetylpiperidine functionality.

The term "deprotecting" refers to removal of a protecting group, such as removal of a benzyl or BOC group bound to an amine. Deprotecting may be preformed by heating and/or addition of reagents capable of removing protecting groups. In preferred embodiments, the deprotecting step involves addition of an acid, base, reducing agent, oxidizing agent, heat, or any combination thereof. One preferred method of removing BOC groups from amino groups is to add HCl in ethyl acetate. Many deprotecting reactions are well known in the art and are described in Protective Groups in Organic Synthesis, Greene, T. W., John Wiley & Sons, New York, N.Y., (1st Edition, 1981), the entire disclosure of which is herein incorporated by reference.

In one aspect, the present invention is directed to compounds of formula I:

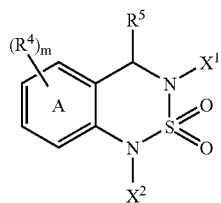

or a pharmaceutically acceptable salt, tautomer or stereoisomer thereof;
wherein:
n is an integer from 0 to 3;
m is an integer from 0 to 4;
$X^1$ is $R^1$ and $X^2$ is W; or
$X^1$ is W and $X^2$ is $R^1$;
W is:

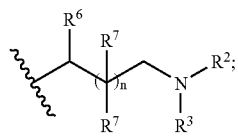

$R^1$ is aryl substituted with 0-3 $R^{11}$ or heteroaryl substituted with 0-3 $R^{11}$;
$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;
$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or
$R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;
$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, arylsulfonamide, alkylamido, or arylamido;
$R^5$ is H, $C_1$-$C_6$ alkyl, $C_6$-$C_{10}$ aryl substituted with 0-3 $R^{15}$, $C_6$-$C_{10}$ aryl-$C_1$-$C_6$ alkyl where said aryl portion is substituted with 0-3 $R^{15}$, heteroaryl substituted with 0-3 $R^{15}$, or heteroaryl-$C_1$-$C_6$ alkyl where said heteroaryl portion is substituted with 0-3 $R^{15}$;
$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;
$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or
$R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;
$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, arylsulfonamide, alkylamido, or arylamido;
$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N.

In a more particular embodiment of the compound of formula I, $X^1$ is W and $X^2$ is $R^1$. Alternatively, $X^1$ is $R^1$ and $X^2$ is W.

In another aspect, the present invention is directed to compounds of formula II:

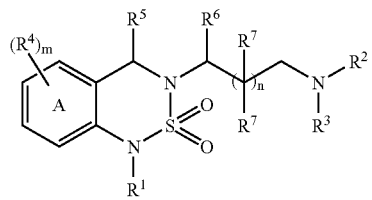

wherein in the variables are the same as defined for the compound of formula I.

In another aspect, the present invention is directed to compounds of formula III:

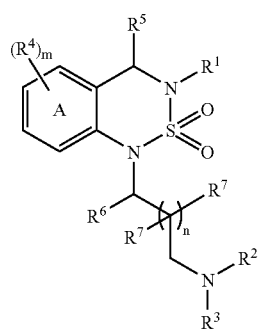

wherein in the variables are the same as defined for the compound of formula I.

In certain preferred embodiments of the compounds of formula I, II or III, n is 1.

In certain preferred embodiments of the compounds of formula I, II or III, m is an integer from 0 to 2. In certain other preferred embodiments of the compounds of formula I, m is an integer from 0 to especially 0 to 1 In certain preferred embodiments of the compounds of formula I, m is 0.

In certain preferred embodiments of the compounds of formula I II or III, $R^1$ is aryl substituted with 0-3 $R^{11}$. In certain more preferred embodiments, $R^1$ is phenyl, tolyl, xylyl, methoxy-phenyl, fluoro-phenyl, difluoro-phenyl, trifluoro-phenyl, chloro-phenyl, fluoro-chloro-phenyl, bromo-phenyl, trifluoromethyl-phenyl trifluoromethoxy-phenyl, methyl-fluoro-phenyl, methoxy-fluoro-phenyl, or naphthyl.

In certain preferred embodiments of the compounds of formula I II or III, $R^1$ is heteroaryl substituted with 0-3 $R^1$. In certain more preferred embodiments, $R^1$ is pyridinyl, methyl-pyridinyl, ethyl-pyridinyl, methoxy-pyridinyl, or quinolinyl.

In certain preferred embodiments of the compounds of formula I II or III, $R^2$ is H, methyl, ethyl, cyclopropyl, or n-butyl. In certain more preferred embodiments, $R^2$ is hydrogen or methyl.

In certain preferred embodiments of the compounds of formula I II or III, $R^3$ is H, methyl, ethyl, cyclopropyl, or n-butyl. In certain more preferred embodiments, $R^3$ is hydrogen or methyl.

In certain preferred embodiments of the compounds of formula I II or III, $R^2$ and $R^3$, together with the nitrogen through which they are attached, form a heterocyclic ring of 6 ring atoms, where one carbon may be optionally replaced with O.

In certain preferred embodiments of the compounds of formula I II or III, $R^4$ is, independently at each occurrence, $C_1$-$C_6$ alkyl, $C_1$-$C_6$ alkoxy, halo, $CF_3$, $OCF_3$, nitrile, or aryl substituted with 0-3 $R^{14}$. In certain more preferred embodiments, $R^4$ is, independently at each occurrence, methyl, methoxy, fluoro, chloro, bromo, $CF_3$, $OCF_3$, nitrile, or phenyl.

In certain preferred embodiments of the compounds of formula I II or III, $R^5$ is H, $C_1$-$C_6$ alkyl, or phenyl. In certain more preferred embodiments, $R^5$ is hydrogen or methyl.

In certain preferred embodiments of the compounds of formula I II or III, $R^6$ is H, $C_1$-$C_6$ alkyl, or phenyl. In certain more preferred embodiments, $R^6$ is hydrogen or methyl.

In certain preferred embodiments of the compounds of formula I II or III, $R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido. In certain preferred embodiments, on a single carbon, one $R^7$ is H and the other $R^7$ is H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido. In certain embodiments, both $R^7$ groups are H.

In certain preferred embodiments of the compounds of formula I II or III, $R^7$ and one of said $R^2$ and $R^3$, together with the nitrogen and carbon through which they are attached, form a heterocyclic or heterobicyclic ring of 3 to 12 ring atoms, where one carbon may be optionally substituted with $R^{13}$ and any additional N atom substituted with $C_1$-$C_4$ alkyl.

In certain preferred embodiments of the compounds of formula I II or III, $R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, aryl, heteroaryl, alkylsulfoxide, alkylsulfone, alkylsulfonamide, arylsulfonamide, alkylamido, or arylamido. In certain more preferred embodiments, $R^{11}$ is methyl, methoxy, chloro, or fluoro, especially fluoro. In certain more preferred embodiments, $R^{12}$ is fluoro.

In certain preferred embodiments of the compounds of formula I II or III, $R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl. In certain more preferred embodiments, $R^{13}$, $R^{14}$, $R^{15}$, and $R^{16}$ are, independently at each occurrence, fluoro.

Preferred compounds of the present invention include:
3-(2,2-dioxido-1-phenyl-1,4-dihydro-3H-2,1,3-benzothiadiazin-3-yl)-N-methylpropan-1-amine;
3-[1-(3-fluorophenyl)-2,2-dioxido-1,4-dihydro-3H-2,1,3-benzothiadiazin-3-yl]-N-methylpropan-1-amine;
N-methyl-3-[1-(3-methylphenyl)-2,2-dioxido-1,4-dihydro-3H-2,1,3-benzothiadiazin-3-yl]propan-1-amine;
3-[1-(3-methoxyphenyl)-2,2-dioxido-1,4-dihydro-3H-2,1,3-benzothiadiazin-3-yl]-N-methylpropan-1-amine;
3-[1-(4-chlorophenyl)-2,2-dioxido-1,4-dihydro-3H-2,1,3-benzothiadiazin-3-yl]-N-methylpropan-1-amine;
3-[1-(3-chloro-4-fluorophenyl)-2,2-dioxido-1,4-dihydro-3H-2,1,3-benzothiadiazin-3-yl]-N-methylpropan-1-amine;
3-[1-(4-fluorophenyl)-2,2-dioxido-1,4-dihydro-3H-2,1,3-benzothiadiazin-3-yl]-N-methylpropan-1-amine;
N-methyl-3-[1-(4-methylphenyl)-2,2-dioxido-1,4-dihydro-3H-2,1,3-benzothiadiazin-3-yl]propan-1-amine;
3-[1-(4-methoxyphenyl)-2,2-dioxido-1,4-dihydro-3H-2,1,3-benzothiadiazin-3-yl]-N-methylpropan-1-amine;
3-[1-(3,4-difluorophenyl)-2,2-dioxido-1,4-dihydro-3H-2,1,3-benzothiadiazin-3-yl]-N-methylpropan-1-amine;
2-[1-(2-fluorophenyl)-2,2-dioxido-1,4-dihydro-3H-2,1,3-benzothiadiazin-3-yl]-N-methylethanamine;
N-{2-[1-(2-fluorophenyl)-2,2-dioxido-1,4-dihydro-3H-2,1,3-benzothiadiazin-3-yl]ethyl}cyclopropanamine;
3-[1-(2-fluorophenyl)-2,2-dioxido-1,4-dihydro-3H-2,1,3-benzothiadiazin-3-yl]-N-methylpropan-1-amine;
N-{3-[1-(2-fluorophenyl)-2,2-dioxido-1,4-dihydro-3H-2,1,3-benzothiadiazin-3-yl]propyl}cyclopropanamine;
4-[1-(2-fluorophenyl)-2,2-dioxido-1,4-dihydro-3H-2,1,3-benzothiadiazin-3-yl]-N-methylbutan-1-amine;
N-{4-[1-(2-fluorophenyl)-2,2-dioxido-1,4-dihydro-3H-2,1,3-benzothiadiazin-3-yl]butyl}cyclopropanamine;
2-[6-fluoro-1-(2-fluorophenyl)-2,2-dioxido-1,4-dihydro-3H-2,1,3-benzothiadiazin-3-yl]-N-methylethanamine;
N-{2-[6-fluoro-1-(2-fluorophenyl)-2,2-dioxido-1,4-dihydro-3H-2,1,3-benzothiadiazin-3-yl]ethyl}cyclopropanamine;
3-[6-fluoro-1-(2-fluorophenyl)-2,2-dioxido-1,4-dihydro-3H-2,1,3-benzothiadiazin-3-yl]-N-methylpropan-1-amine;
N-{3-[6-fluoro-1-(2-fluorophenyl)-2,2-dioxido-1,4-dihydro-3H-2,1,3-benzothiadiazin-3-yl]propyl}cyclopropanamine;
4-[6-fluoro-1-(2-fluorophenyl)-2,2-dioxido-1,4-dihydro-3H-2,1,3-benzothiadiazin-3-yl]-N-methylbutan-1-amine;
N-{4-[6-fluoro-1-(2-fluorophenyl)-2,2-dioxido-1,4-dihydro-3H-2,1,3-benzothiadiazin-3-yl]butyl}cyclopropanamine;
(2S)-4-[6-fluoro-1-(2-fluorophenyl)-2,2-dioxido-1,4-dihydro-3H-2,1,3-benzothiadiazin-3-yl]-1-(methylamino)butan-2-ol;
(2S)-4-[1-(2-fluorophenyl)-2,2-dioxido-1,4-dihydro-3H-2,1,3-benzothiadiazin-3-yl]-1-(methylamino)butan-2-ol;
3-[3-(2-fluorophenyl)-2,2-dioxido-3,4-dihydro-1H-2,1,3-benzothiadiazin-1-yl]-N-methylpropan-1-amine;
2-[3-(2-fluorophenyl)-2,2-dioxido-3,4-dihydro-1H-2,1,3-benzothiadiazin-1-yl]-N-methylethanamine; and
pharmaceutically acceptable salts thereof.

Additional preferred compounds of the present invention include:
4-[1-phenyl-2,2-dioxido-1,4-dihydro-3H-2,1,3-benzothiadiazin-3-yl]-N-methylbutan-1-amine;

4-[1-(2,6-difluorophenyl)-2,2-dioxido-1,4-dihydro-3H-2,1,3-benzothiadiazin-3-yl]-N-methylbutan-1-amine;
4-[1-(2-fluoro-4-methylphenyl)-2,2-dioxido-1,4-dihydro-3H-2,1,3-benzothiadiazin-3-yl]-N-methylbutan-1-amine;
4-[1-(2-chlorophenyl)-2,2-dioxido-1,4-dihydro-3H-2,1,3-benzothiadiazin-3-yl]-N-methylbutan-1-amine;
4-[1-(2,4,6-trifluorophenyl)-2,2-dioxido-1,4-dihydro-3H-2,1,3-benzothiadiazin-3-yl]-N-methylbutan-1-amine;
4-[6-fluoro-1-phenyl-2,2-dioxido-1,4-dihydro-3H-2,1,3-benzothiadiazin-3-yl]-N-methylbutan-1-amine;
4-[6-fluoro-1-(2,6-difluorophenyl)-2,2-dioxido-1,4-dihydro-3H-2,1,3-benzothiadiazin-3-yl]-N-methylbutan-1-amine;
4-[6-fluoro-1-(2-chlorophenyl)-2,2-dioxido-1,4-dihydro-3H-2,1,3-benzothiadiazin-3-yl]-N-methylbutan-1-amine;
4-[6-fluoro-1-(2-fluoro-4-methylphenyl)-2,2-dioxido-1,4-dihydro-3H-2,1,3-benzothiadiazin-3-yl]-N-methylbutan-1-amine;
4-[6-fluoro-1-(2,4,6-trifluorophenyl)-2,2-dioxido-1,4-dihydro-3H-2,1,3-benzothiadiazin-3-yl]-N-methylbutan-1-amine;
4-[6-chloro-1-phenyl-2,2-dioxido-1,4-dihydro-3H-2,1,3-benzothiadiazin-3-yl]-N-methylbutan-1-amine;
4-[6-chloro-1-(2-fluorophenyl)-2,2-dioxido-1,4-dihydro-3H-2,1,3-benzothiadiazin-3-yl]-N-methylbutan-1-amine;
4-[6-chloro-1-(2,6-difluorophenyl)-2,2-dioxido-1,4-dihydro-3H-2,1,3-benzothiadiazin-3-yl]-N-methylbutan-1-amine;
4-[6-chloro-1-(2-fluoro-4-methylphenyl)-2,2-dioxido-1,4-dihydro-3H-2,1,3-benzothiadiazin-3-yl]-N-methylbutan-1-amine;
4-[6-chloro-1-(2-chlorophenyl)-2,2-dioxido-1,4-dihydro-3H-2,1,3-benzothiadiazin-3-yl]-N-methylbutan-1-amine;
4-[6-chloro-1-(2,4,6-trifluorophenyl)-2,2-dioxido-1,4-dihydro-3H-2,1,3-benzothiadiazin-3-yl]-N-methylbutan-1-amine;
4-[6-methyl-1-phenyl-2,2-dioxido-1,4-dihydro-3H-2,1,3-benzothiadiazin-3-yl]-N-methylbutan-1-amine;
4-[6-methyl-1-(2-fluorophenyl)-2,2-dioxido-1,4-dihydro-3H-2,1,3-benzothiadiazin-3-yl]-N-methylbutan-1-amine;
4-[6-methyl-1-(2,6-difluorophenyl)-2,2-dioxido-1,4-dihydro-3H-2,1,3-benzothiadiazin-3-yl]-N-methylbutan-1-amine;
4-[6-methyl-1-(2-fluoro-4-methylphenyl)-2,2-dioxido-1,4-dihydro-3H-2,1,3-benzothiadiazin-3-yl]-N-methylbutan-1-amine;
4-[6-methyl-1-(2-chlorophenyl)-2,2-dioxido-1,4-dihydro-3H-2,1,3-benzothiadiazin-3-yl]-N-methylbutan-1-amine;
4-[6-methyl-1-(2,4,6-trifluorophenyl)-2,2-dioxido-1,4-dihydro-3H-2,1,3-benzothiadiazin-3-yl]-N-methylbutan-1-amine;
4-[6-cyano-1-phenyl-2,2-dioxido-1,4-dihydro-3H-2,1,3-benzothiadiazin-3-yl]-N-methylbutan-1-amine;
4-[6-cyano-1-(2-fluorophenyl)-2,2-dioxido-1,4-dihydro-3H-2,1,3-benzothiadiazin-3-yl]-N-methylbutan-1-amine;
4-[6-cyano-1-(2,6-difluorophenyl)-2,2-dioxido-1,4-dihydro-3H-2,1,3-benzothiadiazin-3-yl]-N-methylbutan-1-amine;
4-[6-cyano-1-(2-fluoro-4-methylphenyl)-2,2-dioxido-1,4-dihydro-3H-2,1,3-benzothiadiazin-3-yl]-N-methylbutan-1-amine;
4-[6-cyano-1-(2-chlorophenyl)-2,2-dioxido-1,4-dihydro-3H-2,1,3-benzothiadiazin-3-yl]-N-methylbutan-1-amine;
4-[6-cyano-1-(2,4,6-trifluorophenyl)-2,2-dioxido-1,4-dihydro-3H-2,1,3-benzothiadiazin-3-yl]-N-methylbutan-1-amine;
4-[1-(2,6-difluorophenyl)-2,2-dioxido-1,4-dihydro-3H-2,1,3-benzothiadiazin-3-yl]-N-methylpropan-1-amine;
4-[1-(2-fluoro-4-methylphenyl)-2,2-dioxido-1,4-dihydro-3H-2,1,3-benzothiadiazin-3-yl]-N-methylpropan-1-amine;
4-[1-(2-chlorophenyl)-2,2-dioxido-1,4-dihydro-3H-2,1,3-benzothiadiazin-3-yl]-N-methylpropan-1-amine;
4-[1-(2,4,6-trifluorophenyl)-2,2-dioxido-1,4-dihydro-3H-2,1,3-benzothiadiazin-3-yl]-N-methylpropan-1-amine;
4-[6-fluoro-1-phenyl-2,2-dioxido-1,4-dihydro-3H-2,1,3-benzothiadiazin-3-yl]-N-methylpropan-1-amine;
4-[6-fluoro-1-(2,6-difluorophenyl)-2,2-dioxido-1,4-dihydro-3H-2,1,3-benzothiadiazin-3-yl]-N-methylpropan-1-amine;
4-[6-fluoro-1-(2-fluoro-4-methylphenyl)-2,2-dioxido-1,4-dihydro-3H-2,1,3-benzothiadiazin-3-yl]-N-methylpropan-1-amine;
4-[6-fluoro-1-(2-chlorophenyl)-2,2-dioxido-1,4-dihydro-3H-2,1,3-benzothiadiazin-3-yl]-N-methylpropan-1-amine;
4-[6-fluoro-1-(2,4,6-trifluorophenyl)-2,2-dioxido-1,4-dihydro-3H-2,1,3-benzothiadiazin-3-yl]-N-methylpropan-1-amine;
4-[6-chloro-1-phenyl-2,2-dioxido-1,4-dihydro-3H-2,1,3-benzothiadiazin-3-yl]-N-methylpropan-1-amine;
4-[6-chloro-1-(2-fluorophenyl)-2,2-dioxido-1,4-dihydro-3H-2,1,3-benzothiadiazin-3-yl]-N-methylpropan-1-amine;
4-[6-chloro-1-(2,6-difluorophenyl)-2,2-dioxido-1,4-dihydro-3H-2,1,3-benzothiadiazin-3-yl]-N-methylpropan-1-amine;
4-[6-chloro-1-(2-fluoro-4-methylphenyl)-2,2-dioxido-1,4-dihydro-3H-2,1,3-benzothiadiazin-3-yl]-N-methylpropan-1-amine;
4-[6-chloro-1-(2-chlorophenyl)-2,2-dioxido-1,4-dihydro-3H-2,1,3-benzothiadiazin-3-yl]-N-methylpropan-1-amine;
4-[6-chloro-1-(2,4,6-trifluorophenyl)-2,2-dioxido-1,4-dihydro-3H-2,1,3-benzothiadiazin-3-yl]-N-methylpropan-1-amine;
4-[6-methyl-1-phenyl-2,2-dioxido-1,4-dihydro-3H-2,1,3-benzothiadiazin-3-yl]-N-methylpropan-1-amine;
4-[6-methyl-1-(2-fluorophenyl)-2,2-dioxido-1,4-dihydro-3H-2,1,3-benzothiadiazin-3-yl]-N-methylpropan-1-amine;
4-[6-methyl-1-(2,6-difluorophenyl)-2,2-dioxido-1,4-dihydro-3H-2,1,3-benzothiadiazin-3-yl]-N-methylpropan-1-amine;
4-[6-methyl-1-(2-fluoro-4-methylphenyl)-2,2-dioxido-1,4-dihydro-3H-2,1,3-benzothiadiazin-3-yl]-N-methylpropan-1-amine;
4-[6-methyl-1-(2-chlorophenyl)-2,2-dioxido-1,4-dihydro-3H-2,1,3-benzothiadiazin-3-yl]-N-methylpropan-1-amine;
4-[6-methyl-1-(2,4,6-trifluorophenyl)-2,2-dioxido-1,4-dihydro-3H-2,1,3-benzothiadiazin-3-yl]-N-methylpropan-1-amine;
4-[6-cyano-1-phenyl-2,2-dioxido-1,4-dihydro-3H-2,1,3-benzothiadiazin-3-yl]-N-methylpropan-1-amine;
4-[6-cyano-1-(2-fluorophenyl)-2,2-dioxido-1,4-dihydro-3H-2,1,3-benzothiadiazin-3-yl]-N-methylpropan-1-amine;
4-[6-cyano-1-(2,6-difluorophenyl)-2,2-dioxido-1,4-dihydro-3H-2,1,3-benzothiadiazin-3-yl]-N-methylpropan-1-amine;

4-[6-cyano-1-(2-fluoro-4-methylphenyl)-2,2-dioxido-1,4-dihydro-3H-2,1,3-benzothiadiazin-3-yl]-N-methylpropan-1-amine;

4-[6-cyano-1-(2-chlorophenyl)-2,2-dioxido-1,4-dihydro-3H-2,1,3-benzothiadiazin-3-yl]-N-methylpropan-1-amine;

4-[6-cyano-1-(2,4,6-trifluorophenyl)-2,2-dioxido-1,4-dihydro-3H-2,1,3-benzothiadiazin-3-yl]-N-methylpropan-1-amine; and pharmaceutically acceptable salts thereof.

In certain preferred embodiments of the compounds of formula I, II or III, the pharmaceutically acceptable salt is a hydrochloride.

Another aspect of the invention provides a process for the preparation of a compound of Formula II:

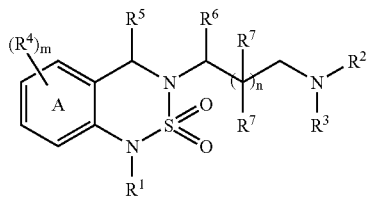

II or a pharmaceutically acceptable salt, tautomer or stereoisomer thereof;

wherein:

n is an integer from 0 to 3;

m is an integer from 0 to 4;

$R^1$ is $C_6$-$C_{10}$ aryl substituted with 0-3 $R^{11}$ or heteroaryl substituted with 0-3 $R^{11}$;

$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;

$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or $R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;

$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;

$R^5$ is H, $C_1$-$C_6$ alkyl, $C_6$-$C_{10}$ aryl substituted with 0-3 $R^{15}$, $C_6$-$C_{10}$ aryl-$C_1$-$C_6$ alkyl where said aryl portion is substituted with 0-3 $R^{15}$, heteroaryl substituted with 0-3 $R^{15}$, or heteroaryl-$C_1$-$C_6$ alkyl where said heteroaryl portion is substituted with 0-3 $R^{15}$;

$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N;

said process comprising:

reacting $G_{a1}$-$R^1$ with a compound of formula IIA:

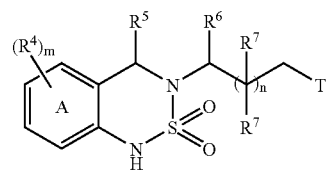

IIA to form a compound of formula IIB:

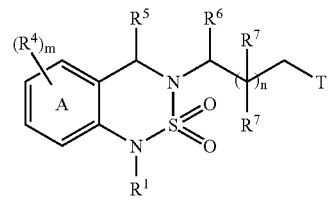

IIB wherein, $G_{a1}$ and $G_{a2}$ are independently, activating groups;

$G_{p1}$ is a protecting group;

T is —$N(R^2)(G_{p1})$, $G_{a2}$, or —$N(R^2)(R^3)$;

wherein, if T is —$N(R^2)(R^3)$, the compound of formula II is formed; or if T is —$N(R^2)(G_{p1})$, the process further comprises:

deprotecting the compound of formula IIB to form a deprotected compound;

wherein, if $R^3$ in the compound of formula II is H, then the compound of formula II is formed; or if $R^3$ is other than H, the process further comprises reacting the deprotected compound with activated-$R^3$, wherein the compound of formula II is formed; or if T is $G_{a2}$, the process further comprises:

reacting the compound of formula IIB with —$N(R^2)(R^3)$ to form the compound of formula II; or reacting the compound of formula IIB with —$N(R^2)(G_{p1})$ to form a protected compound;

deprotecting the protected compound to form a deprotected compound;
wherein,
if $R^3$ in the compound of formula II is H, then the compound of formula II is formed; or
if $R^3$ is other than H, the process further comprises reacting the deprotected compound with activated-$R^3$,
wherein the compound of formula II is formed.

In another embodiment, activated-$R^3$ is halo-$R^3$.

In another embodiment, the compound of formula IIA is formed by:
reacting sulfamide with a compound of formula IIC:

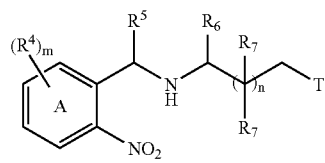

IIC thereby forming a compound of formula IIA.

In another embodiment, the step of reacting sulfamide with a compound of formula IC is performed in the presence of a reducing agent. More particularly, the reducing agent is a reducing agent listed in the Examples section.

In another embodiment, the compound of formula IIC is formed by: reacting a compound of formula IID:

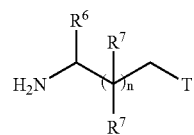

IID with a compound of formula IIE:

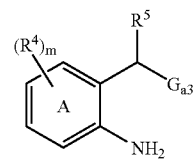

IIE wherein, $G_{a3}$ is an activating group;

thereby forming the compound of formula IIC.

In another embodiment, the activating group is selected from the group consisting of halo, tosylate, mesylate, and triflate. More particularly, the activating group is Cl.

In another embodiment, the protecting group is selected from the group consisting of BOC, benzyl, acetyl, PMB, $C_1$-$C_6$ alkyl, Fmoc, Cbz, trifluoroacetyl, tosyl and triphenylmethyl. More particularly, the protecting group is BOC.

In another embodiment, the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

In another embodiment, any one of the steps is performed at or above 30° C. or any one of the steps includes a purification step comprising at least one of: filtration, extraction, chromatography, trituration, or recrystallization.

In another embodiment, any one of the steps is performed in: a protic solvent, an aprotic solvent, a polar solvent, a nonpolar solvent, a protic polar solvent, an aprotic nonpolar solvent, or an aprotic polar solvent.

Another aspect of the invention provides a process for the preparation of a compound of formula II:

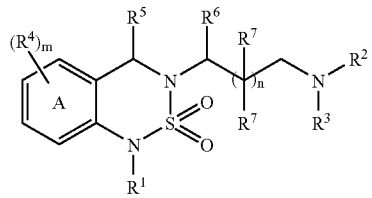

II or a pharmaceutically acceptable salt, tautomer or stereoisomer thereof;

wherein:

n is an integer from 0 to 3;

m is an integer from 0 to 4;

$R^1$ is $C_6$-$C_{10}$ aryl substituted with 0-3 $R^{11}$ or heteroaryl substituted with 0-3 $R^{11}$.

$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;

$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or $R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;

$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;

$R^5$ is H;

$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N;

said process comprising:

reacting a compound of formula IIF:

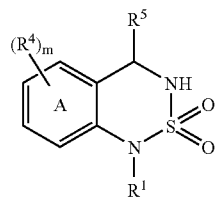

with a compound of formula IIG:

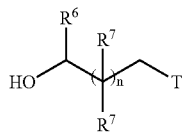

IIG to form a compound of formula IIB:

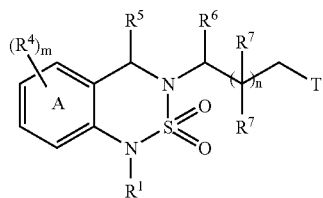

IIB wherein,

T is —$N(R^2)(G_{p1})$, $G_{a2}$, or —$N(R^2)(R^3)$;

wherein, if T is —$N(R^2)(R^3)$, the compound of formula II is formed;

if T is —$N(R^2)(G_{p1})$, the process further comprises:

deprotecting the compound of formula IIB to form a deprotected compound;

wherein, if $R^3$ in the compound of formula II is H, then the compound of formula II is formed; or if $R^3$ is other than H, the process further comprises reacting the deprotected compound with activated-$R^3$, wherein the compound of formula II is formed; or if T is $G_{a2}$, the process further comprises:

reacting the compound of formula IIB with —$N(R^2)(R^3)$ to form the compound of formula II; or reacting the compound of formula IIB with —$N(R^2)(G_{p1})$ to form a protected compound;

deprotecting the protected compound to form a deprotected compound;

wherein, if $R^3$ in the compound of formula II is H, then the compound of formula II is formed; or if $R^3$ is other than H, the process further comprises reacting the deprotected compound with activated-$R^3$, wherein the compound of formula II is formed.

In another embodiment, the reacting step is performed in the presence of dialkyl azodicarboxylate and triphenylphosphine ($PPh_3$). More particularly, the dialkyl azodicarboxylate is diisopropyl azodicarboxylate.

In another embodiment, activated-$R^3$ is halo-$R^3$.

In another embodiment, T is Cl. Alternatively, T is Br.

In another embodiment, the compound of formula IIF is prepared by: reacting sulfamide with a compound of formula IIH:

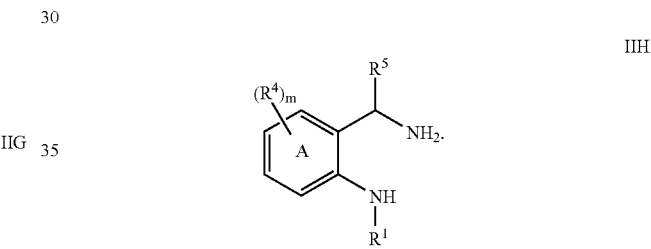

IIH

In another embodiment, the compound of formula IIH is prepared by: reducing a compound of formula IIJ:

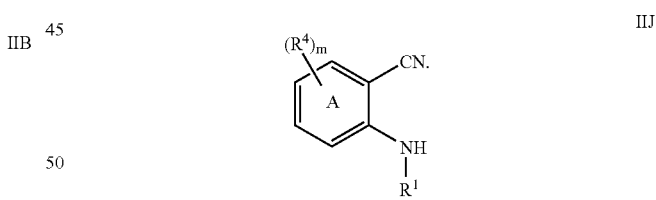

IIJ

In another embodiment, the reducing step comprises contacting the compound of formula IIJ with borane.

In another embodiment, the compound of formula IIJ is prepared by: reacting $R^1NH_2$ with a compound of formula IIK:

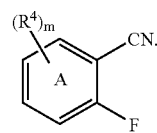

IIK

In another embodiment, the reacting step is performed in the presence of a base. More particularly, the base is potassium tertiary butoxide (KOt-Bu).

In another embodiment, the activating group is selected from the group consisting of halo, tosylate, mesylate, triflate, and oxo. More particularly, the activating group is Br.

In another embodiment, the protecting group is selected from the group consisting of BOC, benzyl, acetyl, PMB, $C_1$-$C_6$ alkyl, Fmoc, Cbz, trifluoroacetyl, tosyl and triphenylmethyl. More particularly, the protecting group is BOC.

In another embodiment, the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

In another embodiment, any one of steps is performed at or above 30° C. or any one of steps further comprises a purification step comprising at least one of: filtration, extraction, chromatography, trituration, or recrystallization.

In another embodiment, any one of the steps is performed in: a protic solvent, an aprotic solvent, a polar solvent, a nonpolar solvent, a protic polar solvent, an aprotic nonpolar solvent, or an aprotic polar solvent.

Another aspect of the invention provides a compound of formula IIA, formula IIB, formula IIC, formula IID, formula IIE, formula IIF, formula IIG, formula IIH, formula IIJ, formula IIK, or a combination thereof.

It is understood that the present invention provides each of the process steps in isolation and/or in combination with other steps (i.e. a partial or total synthesis). Additionally, the present invention includes compounds comprising any of the intermediates involved in the process steps. Additionally, the present invention includes compositions comprising any of the intermediates involved in the process steps and reagents, solvents, acids, bases, reducing agents, oxidizing agents, catalysts and other intermediates present in the reaction mixture.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972), the entire disclosures of which are herein incorporated by reference.

The present invention includes prodrugs of the compounds of formula I, II or III. "Prodrug," as used herein, means a compound which is convertible in vivo by metabolic means (e.g. by hydrolysis) to a compound of formula I, II or III. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975), the entire disclosures of which are herein incorporated by reference.

Further, the compounds of formula I, II or III may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991, the entire disclosure of which is herein incorporated by reference.

Compounds of the present invention are suitably prepared in accordance with the following general description and specific examples. Variables used are as defined for formula I, II or III, unless otherwise noted. The reagents used in the preparation of the compounds of this invention can be either commercially obtained or can be prepared by standard procedures described in the literature. In accordance with this invention, compounds of formula I and II may be produced by the following reaction schemes (Schemes 1 to 4).

The compounds of this invention contain chiral centers, providing for various stereoisomeric forms such as diastereomeric mixtures, enantiomeric mixtures as well as optical isomers. The individual optical isomers can be prepared directly through asymmetric and/or stereospecific synthesis or by conventional chiral separation of optical isomers from the enantiomeric mixture.

Scheme 1

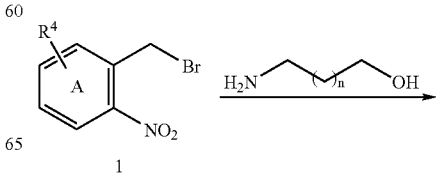

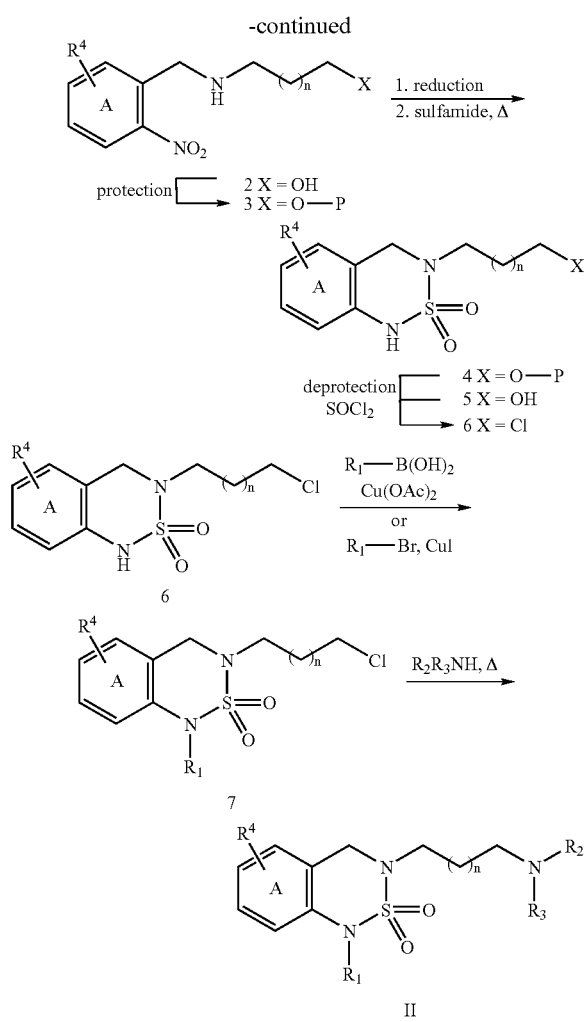

Nitroarenes with a suitable leaving group on a benzylic carbon ortho to the nitro group, such as bromomethyl-nitroarene 1, can be substituted with an ω-hydroxyalkylamine under standard conditions for nucleophilic substitution reactions (see J. March, "Advanced Organic Chemistry" 4$^{th}$ edition, John Wiley & Sons, 1992 incorporated herein by reference) to provide secondary amine 2. Other examples of suitable leaving groups for this transformation include chloride, iodide, mesylate, tosylate, or related species. The free hydroxy group of 2 may be protected to provide 3 using any of the known compatible protecting groups (denoted as P in Scheme 1) such as a silyl ether. (See T. W. Greene and P. G. M. Wuts "Protective Groups in Organic Synthesis" 3$^{rd}$ edition, John Wiley & Sons, 1999, incorporated herein by reference, for a description of appropriate protecting groups, and for reaction conditions for installation and cleavage.) The nitro group of 3 can then be reduced to aniline using standard conditions (See R. C Larock, "Comprehensive Organic Transformations," 2$^{nd}$ edition, John Wiley & Sons, 1999, incorporated herein by reference) for reducing nitroarenes, such as zinc powder. After reduction, the diamine can be cyclized to form sulfamide 4. Any of the known reactions or reaction sequences for forming cyclic sulfamides could be used, such as heating the diamine and sulfamide in refluxing diglyme. The hydroxyl group of 4, if protected, can then be unmasked to provide 5 using the appropriate deprotection conditions, such as TBAF for silyl ethers, and then converted into a suitable leaving group for nucleophilic substitution, such as chloride to make structure 6. Pendant aryl or heteroaryl groups ($R_1$) can be introduced onto the sulfamide template 6 by coupling aryl or heteroaryl boronic acids or boronate esters using copper(II) acetate, or other copper- or palladium-catalyzed reaction conditions known in the chemical literature, to provide 7. Aryl and heteroaryl groups ($R_1$) could likewise be appended to 6 by copper or palladium-catalyzed coupling of the corresponding halides, triflates, or other compatible organometallic reagents. (For information on some of the methods which could be used for the introduction of $R_1$ by an arylation reaction, see the following references incorporated herein by reference: Deng, Wei; Liu, Lei; Zhang, Chen; Liu, Min; Guo, Qing-Xiang. "Copper-catalyzed cross-coupling of sulfonamides with aryl iodides and bromides facilitated by amino acid ligands" *Tetrahedron Letters* 2005, 46, 7295-7298; Burton, George; Cao, Ping; Li, Gang; Rivero, Ralph. "Palladium-Catalyzed Intermolecular Coupling of Aryl Chlorides and Sulfonamides under Microwave Irradiation." *Organic Letters* 2003, 5, 4373-4376; He, Huan; Wu, Yong-Jin. "Copper-catalyzed N-arylation of sulfonamides with aryl bromides and iodides using microwave heating." *Tetrahedron Letters* 2003, 44, 3385-3386; Yin, Jingjun; Buchwald, Stephen L. "Pd-Catalyzed Intermolecular Amidation of Aryl Halides: The Discovery that Xantphos Can Be Trans-Chelating in a Palladium Complex." *Journal of the American Chemical Society* 2002, 124, 6043-6048. Combs, Andrew P.; Rafalski, Maria. "N-Arylation of Sulfonamides on Solid Supports" *Journal of Combinatorial Chemistry* 2000, 2, 29-32; Rafalski, Maria; Saubern, Simon; Lam, Patrick Y. S.; Combs, Andrew P. "Cupric acetate-mediated N-arylation by arylboronic acids: Solid-supported C—N cross-coupling reaction. "Book of Abstracts, 218th ACS National Meeting, New Orleans, Aug. 22-26, 1999), the entire disclosure of which are herein incorporated by reference. An alternative synthesis of 7 could employ first coupling the sulfamide nitrogen of 4 or 5 to aryl or heteroaryl groups $R_1$ as described for 6, and then the free or protected hydroxyl group converted to a leaving group such as chloride as described above. The chloride or other suitable leaving group on 7 could then be displaced by a suitable primary or secondary amine ($R_2R_3NH$), such as methyl amine, following standard reaction conditions for nucleophilic substitutions, resulting in compounds of formula I or II.

Scheme 2

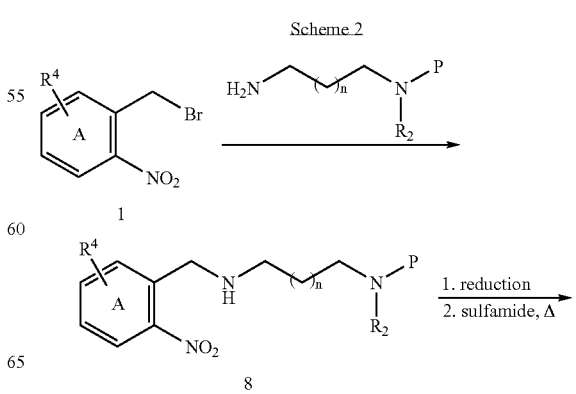

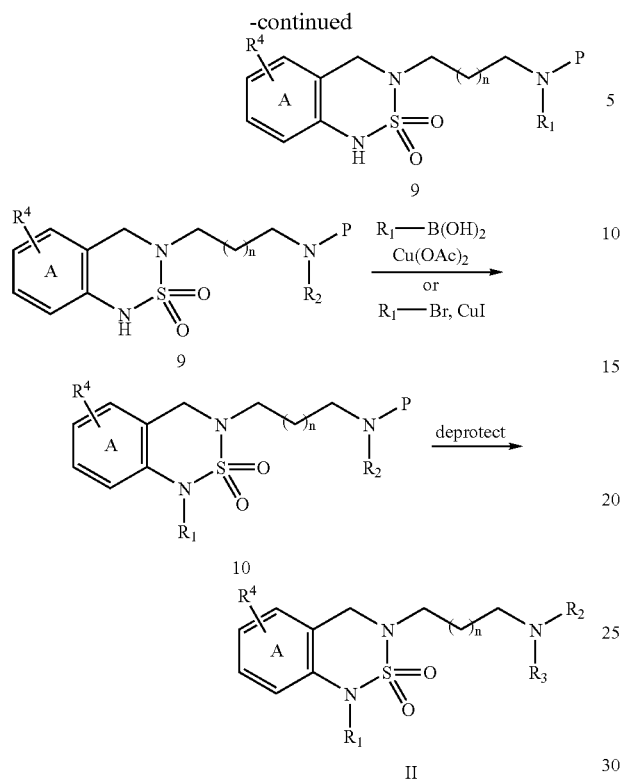
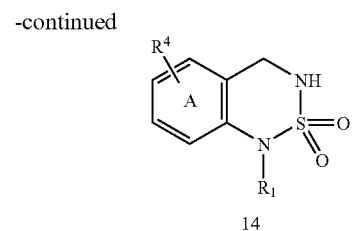

An alternative synthesis of the compounds of formula I or II beginning with 1 could involve installation of the side chain containing a protected primary or secondary amine, using standard alkylation conditions, resulting in structure 8. Any compatible amine protecting group (denoted as P in Scheme 2), such as t-butoxycarbonyl) could be used. The nitro group of 8 could then be reduced to the aniline using standard conditions, and the resulting diamine converted to 9 using known methods for installing sulfonyl groups, such as heating in the presence of sulfamide. Aryl or heteroaryl groups $R_1$ can then be appended to 9 using known copper- or palladium-catalyzed arylation conditions, resulting in structure 10. Appropriate deprotection conditions, such as HCl for t-butoxycarbonyl, can then be used to remove the amine protecting group providing.

Scheme 3

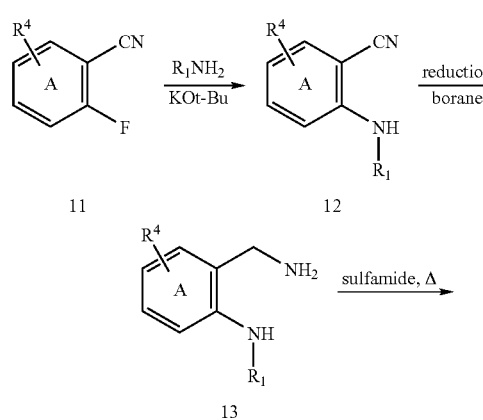

Compounds of formula I or II can also be made starting with ortho-fluoro-cyanoarene 11. Nucleophilic aromatic substitution of fluoride could be achieved with the anion of a suitable aniline, resulting in structure 12. Suitable conditions for this transformation could include deprotonation of the aniline with a strong base, such as butyllithium, before reaction with the aryl fluoride. Nitrile 12 could then be reduced under standard conditions, such as treatment with lithium aluminum hydride, to provide structure 13. Diamine 13 could then be converted to 14 using known methods for installing sulfonyl groups, such as heating in presence of sulfamide. The side chain could then be appended to 14 using standard Mitsunobu conditions with an appropriate alcohol containing a terminal leaving group such as chloride, to provide 7. Structure 7 could also be made from 14 by nucleophilic substitution of a reagent containing a leaving-groups at both ends of the side chain, such as 1-bromo-3-chloropropane. The chloride or other suitable leaving group on 7 could then be displaced by a suitable primary or secondary amine ($R_2R_3NH$), such as methyl amine, following standard reaction conditions for nucleophilic substitutions, resulting in compounds of formula I or II. Alternatively, structure 10 could be prepared by substituting 14 with an alcohol sidechain containing a protected primary or secondary amine using standard Mitsunobu conditions. Deprotection of 10 could then be achieved using appropriate conditions, resulting in compounds of formula I or II.

Scheme 4

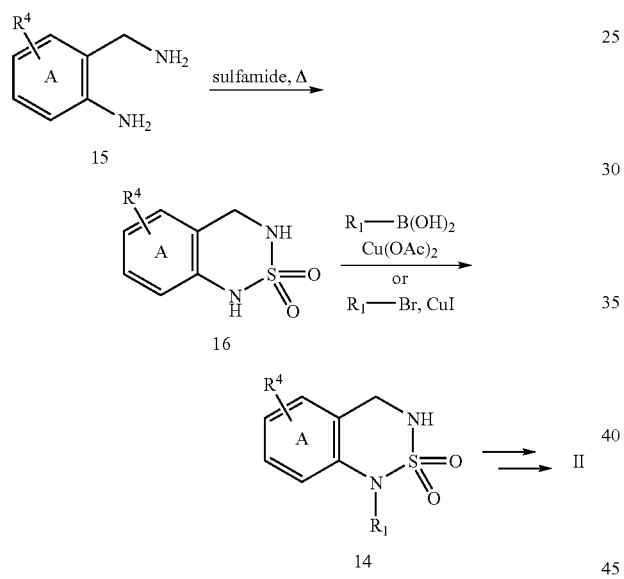

Another method for the synthesis of compounds of formula I or II can begin with diamine 15. Reaction of 15 with sulfamide, or any other suitable reagent of introducing a sulfonyl group, could generate structure 16. The aryl-sulfamide nitrogen of 16 could then be coupled to aryl or heteroaryl groups $R_1$ using known copper- or palladium-catalyzed arylation conditions, resulting in structure 14. Structure 14 could then be converted to a compound of formula I or II by the sequence described in Scheme 3.

Scheme 5

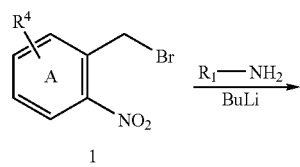

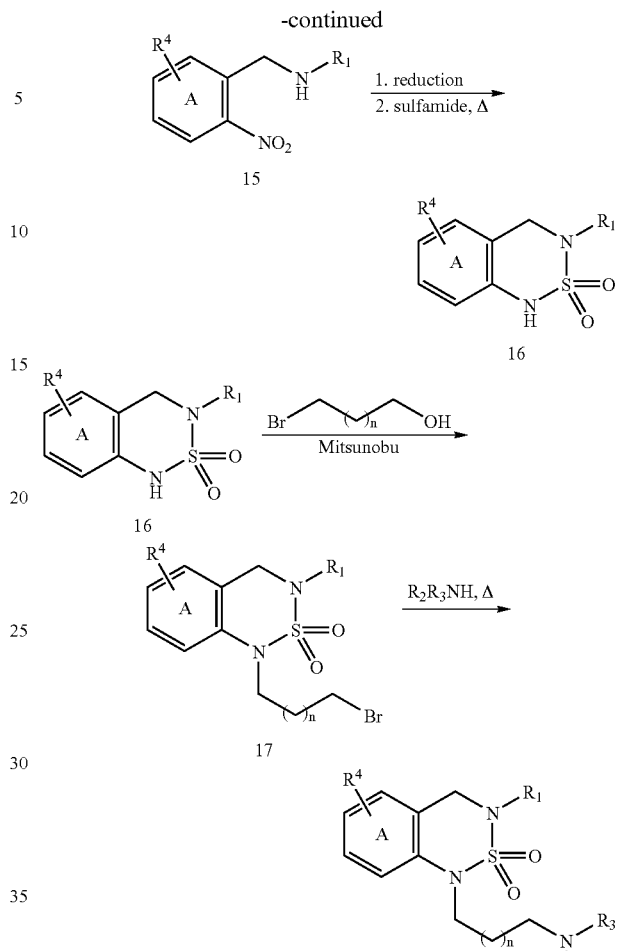

Compounds of formula III can also be made starting with bromomethyl-nitroarene 1, followed by substitution with a primary amine. The nitro group of 15 can then be reduced to aniline using standard conditions (See R. C Larock, "Comprehensive Organic Transformations," $2^{nd}$ edition, John Wiley & Sons, 1999, incorporated herein by reference) for reducing nitroarenes, such as zinc powder. After reduction, the diamine can be cyclized to form sulfamide 16. Any of the known reactions or reaction sequences for forming cyclic sulfamides could be used, such as heating the diamine and sulfamide in refluxing diglyme. The side chain could then be appended to 16 using standard Mitsunobu conditions with an appropriate alcohol containing a terminal leaving group such as bromide, to provide 17. Structure 17 could also be made from 14 by nucleophilic substitution of a reagent containing a leaving-groups at both ends of the side chain, such as 1-bromo-3-chloropropane. The chloride or other suitable leaving group on 7 could then be displaced by a suitable primary or secondary amine ($R_2R_3NH$), such as methyl amine, following standard reaction conditions for nucleophilic substitutions, resulting in compounds of formula III. Alternatively, structure III could be prepared by substituting 17 with an alcohol sidechain containing a protected primary or secondary amine using standard Mitsunobu conditions.

Deprotection could then be achieved using appropriate conditions, resulting in compounds of formula III.

In other embodiments, the invention is directed to pharmaceutical compositions, comprising:
a. at least one compound of formula I, II or III or pharmaceutically acceptable salt thereof; and
b. at least one pharmaceutically acceptable carrier.

Generally, the compound of formula I, II or III, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, II or III, or a pharmaceutically acceptable salt thereof, will be present at a level of at least about 1%, by weight, based on the total weight of the pharmaceutical composition. More preferably, the compound of formula I, II or III, or a pharmaceutically acceptable salt thereof, will be present at a level of at least about 5%, by weight, based on the total weight of the pharmaceutical composition. Even more preferably, the compound of formula I, II or III or a pharmaceutically acceptable salt thereof will be present at a level of at least about 10%, by weight, based on the total weight of the pharmaceutical composition. Yet even more preferably, the compound of formula I, II or III, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985), the entire disclosure of which is herein incorporated by reference. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to about 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions for parenteral administration, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other condition or disorder. Such administration includes use of each type of therapeutic agent in a concurrent manner. In either case, the treatment regimen will provide beneficial effects of the drug combination in treating the conditions or disorders described herein.

The route of administration may be any enteral or parenteral route which effectively transports the active compound of formula I, II or III, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intrathecal, intra-articular, intranasal, ophthalmic solution or an ointment. Furthermore, the administration of compound of formula I, II or III, or pharmaceutically acceptable salt thereof, with other active ingredients may be separate, consecutive or simultaneous.

In one embodiment, the present invention is directed to methods for treating or preventing a condition selected from the group consisting of a vasomotor symptom, sexual dysfunction, gastrointestinal disorder, genitourinary disorder, chronic fatigue syndrome, fibromyalgia syndrome, depression disorder, diabetic neuropathy, pain, and combinations thereof in a subject in need thereof, comprising the step of:

administering to said subject an effective amount of a compound of formula I, II or III or pharmaceutically acceptable salt thereof.

In certain embodiments, the vasomotor symptom is hot flush.

In certain embodiments, the sexual dysfunction is desire-related or arousal-related.

In certain embodiments, the gastrointestinal disorder or the genitourinary disorder is stress incontinence or urge incontinence.

In certain embodiments, the condition is chronic fatigue syndrome.

In certain embodiments, the condition is fibromyalgia syndrome.

In certain embodiments, the condition is a depression disorder selected from the group consisting of major depressive disorder, generalized anxiety disorder, panic disorder, attention deficit disorder with or without hyperactivity, sleep disturbance, social phobia, and combinations thereof.

In certain embodiments, the disorder is an endogenous behavioral disorder or a cognitive disorder.

In certain embodiments, the condition is diabetic neuropathy.

In certain embodiments, the condition is pain.

In certain embodiments, the pain is acute centralized pain, acute peripheral pain, or a combination thereof.

In certain embodiments, the pain is chronic centralized pain, chronic peripheral pain, or a combination thereof.

In certain embodiments, the pain is neuropathic pain, visceral pain, musculoskeletal pain, bony pain, cancer pain, inflammatory pain, or a combination thereof.

In certain embodiments, the neuropathic pain is associated with diabetes, post traumatic pain of amputation, lower back pain, cancer, chemical injury, toxins, major surgery, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, viral infection, bacterial infection, metastatic infiltration, adiposis dolorosa, burns, central pain conditions related to thalamic conditions, or a combination thereof.

In certain embodiments, the neuropathic pain is post-herpetic neuralgia.

In certain embodiments, the visceral pain is associated with ulcerative colitis, irritable bowel syndrome, irritable bladder, Crohn's disease, rheumatologic (arthralgias), tumors, gastritis, pancreatitis, infections of the organs, biliary tract disorders, or a combination thereof.

In certain embodiments, the pain is female-specific pain.

The present invention provides a treatment for vasomotor symptoms by methods of recovering the reduced activity of norepinephrine. Without wishing to be bound by any theory, norepinephrine activity in the hypothalamus or in the brainstem can be elevated by (i) blocking the activity of the NE transporter, (ii) blocking the activity of the presynaptic adrenergic $\alpha_2$ receptor with an antagonist, or (iii) blocking the activity of 5-HT on NE neurons with a 5-HT$_{2a}$ antagonist.

The compounds of the invention are also useful to prevent and treat pain. The pain may be, for example, acute pain or chronic pain. The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pain associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

3-(2,2-dioxido-1-phenyl-1,4-dihydro-3H-2,1,3-benzothiadiazin-3-yl)-N-methylpropan-1-amine hydrochloride

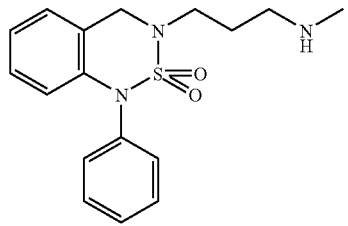

Step 1: A solution of 2-nitrobenzyl amine (17 g, 78 mmol) in DMF (50 mL) was cooled to 0° C. and treated dropwise with a solution of 3-amino-1-propanol (50 mL, 0.65 mol) in DMF (150 mL) over 0.5 hours. The reaction mixture was stirred at 0° C. for 1 hour, then warmed to room temperature for 2 hours, and evaporated to a red oil. The crude product residue was purified by flash chromatography (SiO$_2$, 10% 0.5 M NH$_3$-methanol/dichloromethane) to afford 3-[(2-nitrobenzyl)amino]propan-1-ol (16 g, 98%) as a yellow oil:

HPLC purity 99.1% at 210-370 nm, 5.9 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{10}H_{14}N_2O_3$+H+, 211.10772; found (ESI, [M+H]$^+$), 211.1074.

Step 2: A solution of 3-[(2-nitrobenzyl)amino]propan-1-ol (1.1 g, 5.0 mmol) in dichloromethane (50 mL) was treated with imidazole (0.68 g, 10 mmol) and tert-butylchlorodiphenylsilane (1.4 mL, 5.5 mmol) and stirred at 23° C. for 2 hours. The reaction mixture was quenched by the addition of H$_2$O (50 mL) and 2 M aqueous NaOH (10 mL), and extracted with dichloromethane (2×50 mL), dried (Na$_2$SO$_4$), and evaporated. Flash chromatography (SiO$_2$, 5-50% ethyl acetate/hexanes) provided 3-{[tert-butyl(diphenyl)silyl]oxy}-N-(2-nitrobenzyl) propan-1-amine (1.8 g, 80%) as a yellow oil:

HPLC purity 99.0% at 210-370 nm, 10.4 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{26}H_{32}N_2O_3Si$+H+, 449.22550; found (ESI, [M+H]$^+$), 449.226.

Step 3: A solution of 3-{[tert-butyl(diphenyl)silyl]oxy}-N-(2-nitrobenzyl)propan-1-amine (1.6 g, 3.6 mmol) in ethanol (20 mL) was treated with a solution of ammonium chloride (0.97 g, 18 mmol) in H$_2$O (10 mL). The suspension was heated to 50° C., treated with zinc powder (3.5 g, 53 mmol), and stirred for 1.5 hours. The reaction mixture was cooled to room temperature, and filtered. The filtrate was diluted with H$_2$O, extracted with dichloromethane, and dried (Na$_2$SO$_4$). Flash chromatography (SiO$_2$, 0-10% 0.5 M NH$_3$-methanol/dichloromethane) provided 2-{[(3-{[tert-butyl(diphenyl)silyl]oxy}propyl)amino]methyl}aniline (1.4 g, 94%) as a yellow oil:

HPLC purity 100.0% at 210-370 nm, 10.3 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{26}H_{34}N_2OSi$+H+, 419.25132; found (ESI, [M+H]$^+$), 419.2425.

Step 4: A solution of 2-{[(3-{[tert-butyl(diphenyl)silyl]oxy}propyl)amino]methyl}aniline (0.45 g, 1.1 mmol) and sulfamide (0.12 g, 1.3 mmol) in diglyme (5 mL) was added dropwise to a flask containing refluxing diglyme (3 mL) over 10 minutes. The reaction mixture was stirred at reflux for 1 hour, then cooled to room temperature and evaporated to a brown oil. The crude reaction product was purified by flash chromatography (SiO$_2$, 3-30% ethyl acetate/hexanes) to afford 3-(3-{[tert-butyl(diphenyl)silyl]oxy}propyl)-3,4-dihydro-1H-2,1,3-benzothiadiazine 2,2-dioxide (0.50 g, 95%) as a colorless oil:

HPLC purity 98.6% at 210-370 nm, 11.9 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{26}H_{32}N_2O_3SSi$+H+, 481.19757; found (ESI, [M+H]$^+$+), 481.201.

Step 5: A solution of 3-(3-{[tert-butyl(diphenyl)silyl]oxy}propyl)-3,4-dihydro-1H-2,1,3-benzothiadiazine 2,2-dioxide (0.44 g, 0.92 mmol) in tetrahydrofuran (4 mL) was treated with tetrabutylammonium fluoride (1.4 mL of a 1 M solution in tetrahydrofuran, 1.4 mmol) and acetic acid (0.16 mL, 2.8 mmol), and stirred at 23° C. for 18 hours. The reaction mixture was diluted with H$_2$O (50 mL) and extracted with dichloromethane (2×50 mL), dried (Na$_2$SO$_4$), and evaporated. Flash chromatography (SiO$_2$, 2.5-100% ethyl acetate/hexanes) provided 3-(2,2-dioxido-1,4-dihydro-3H-2,1,3-benzothiadiazin-3-yl)propan-1-ol (0.20 g, 90%) as a colorless oil:

HPLC purity 100.0% at 210-370 nm, 6.4 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{10}H_{14}N_2O_3S$+H+, 243.07979; found (ESI, [M+H]$^+$), 243.0793.

Step 6: A solution of 3-(2,2-dioxido-1,4-dihydro-3H-2,1,3-benzothiadiazin-3-yl)propan-1-ol (1.0 g, 4.1 mmol) in dichloromethane (20 mL) was treated with thionyl chloride (0.91 mL, 12.3 mmol) and dimethylformamide (0.20 mL) and stirred at 23° C. for 16 hours. Additional thionyl chloride (0.30 mL, 4.1 mmol) was added and stirring was continued for an additional 4 hours. The reaction mixture was quenched by the addition of methanol (5 mL) and evaporated. Flash chromatography (SiO$_2$, 3-40% ethyl acetate/hexanes) provided 3-(3-chloropropyl)-3,4-dihydro-1H-2,1,3-benzothiadiazine 2,2-dioxide (0.85 g, 79%) as a yellow oil:

HPLC purity 100.0% at 210-370 nm, 9.5 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{10}H_{13}ClN_2O_2S+H+$, 261.04590; found (ESI, [M+H]$^+$), 261.0464.

Step 7: A solution of 3-(3-chloropropyl)-3,4-dihydro-1H-2,1,3-benzothiadiazine 2,2-dioxide (0.46 g, 1.75 mmol) in dichloromethane (10 mL) was treated with pyridine (0.16 mL, 2.6 mmol), phenylboronic acid (0.43 g, 3.5 mmol) and copper(II) acetate (0.48 g, 2.6 mmol) and stirred at 23° C. for 16 hours. The reaction mixture was quenched by the addition of ammonium hydroxide (10 mL), diluted with methanol (2.0 mL), extracted with dichloromethane (3×10 mL), dried (Na$_2$SO$_4$), and evaporated. Flash chromatography (SiO$_2$, 3-40% ethyl acetate/hexanes) provided 3-(3-chloropropyl)-1-phenyl-3,4-dihydro-1H-2,1,3-benzothiadiazine 2,2-dioxide (0.055 g, 9.4%) as a yellow film:

HPLC purity 100.0% at 210-370 nm, 11.4 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{16}H_{17}ClN_2O_2S+H+$, 337.07720; found (ESI, [M+H]$^+$), 337.0782.

Step 8: 3-(3-chloropropyl)-1-phenyl-3,4-dihydro-1H-2,1,3-benzothiadiazine 2,2-dioxide (0.030 g, 0.089 mmol) was dissolved in an 8 M solution of methylamine in tetrahydrofuran (5 mL), treated with KI (0.030 g, 0.18 mmol), and stirred in a capped vial at 50° C. for 20 hours. The reaction mixture was evaporated and the residue purified by flash chromatography (SiO$_2$, 0-5% 7 M NH$_3$-methanol/dichloromethane). The purified free-base was dissolved in ethyl ether (10 mL) and treated with hydrogen chloride (1.0 mL of a 2 M solution in ethyl ether), resulting in a white precipitate that was isolated by decantation and dried under vacuum to afford 3-(2,2-dioxido-1-phenyl-1,4-dihydro-3H-2,1,3-benzothiadiazin-3-yl)-N-methylpropan-1-amine hydrochloride (0.030 g, 92%) as a white solid:

HPLC purity 98.7% at 210-370 nm, 7.1 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for C17H21N3O2S+H+, 332.14272; found (ESI, [M+H]+), 332.1433.

Example 2

3-[1-(3-fluorophenyl)-2,2-dioxido-1,4-dihydro-3H-2,1,3-benzothiadiazin-3-yl]-N-methylpropan-1-amine hydrochloride

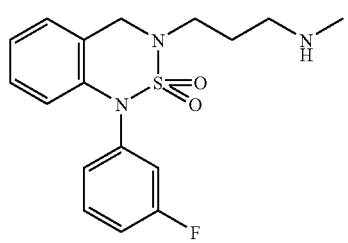

Step 1: In an analogous manner to Example 1 step 7, 3-(3-chloropropyl)-3,4-dihydro-1H-2,1,3-benzothiadiazine 2,2-dioxide (400 mg) was coupled to m-fluorophenylboronic acid to provide 3-(3-chloropropyl)-1-(3-fluorophenyl)-3,4-dihydro-1H-2,1,3-benzothiadiazine 2,2-dioxide (78 mg):

HPLC purity 100.0% at 210-370 nm, 11.6 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{16}H_{16}ClFN_2O_2S+H+$, 355.06778; found (ESI, [M+H]$^+$), 355.0692.

Step 2: In an analogous manner to Example 1, step 8, 3-(3-chloropropyl)-1-(3-fluorophenyl)-3,4-dihydro-1H-2,1, 3-benzothiadiazine 2,2-dioxide (32 mg) was reacted with methylamine and then treated with HCl to provide 3-[1-(3-fluorophenyl)-2,2-dioxido-1,4-dihydro-3H-2,1,3-benzothiadiazin-3-yl]-N-methylpropan-1-amine hydrochloride (26 mg):

HPLC purity 99.2% at 210-370 nm, 10.0 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for C17H20FN3O2S+H+, 350.13330; found (ESI, [M+H]+), 350.1321.

Example 3

N-methyl-3-[1-(3-methylphenyl)-2,2-dioxido-1,4-dihydro-3H-2,1,3-benzothiadiazin-3-yl]propan-1-amine hydrochloride

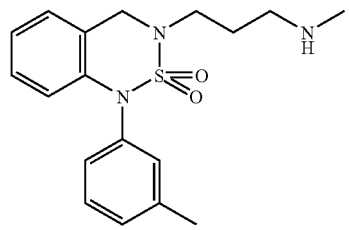

Step 1: In an analogous manner to Example 1 step 7, 3-(3-chloropropyl)-3,4-dihydro-1H-2,1,3-benzothiadiazine 2,2-dioxide (408 mg) was coupled to m-tolylboronic acid to provide 3-(3-chloropropyl)-1-(3-methylphenyl)-3,4-dihydro-1H-2,1,3-benzothiadiazine 2,2-dioxide (39 mg):

HPLC purity 97.1% at 210-370 nm, 10.5 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{17}H_{19}ClN_2O_2S+H+$, 351.09285; found (ESI, [M+H]+), 351.0978.

Step 2: In an analogous manner to Example 1, step 8, 3-(3-chloropropyl)-1-(3-methylphenyl)-3,4-dihydro-1H-2, 1,3-benzothiadiazine 2,2-dioxide (21 mg) was reacted with methylamine and then treated with HCl to provide N-methyl-3-[1-(3-methylphenyl)-2,2-dioxido-1,4-dihydro-3H-2,1,3-benzo thiadiazin-3-yl]propan-1-amine hydrochloride (18 mg):

HPLC purity 100.0% at 210-370 nm, 10.3 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{18}H_{23}N_3O_2S$+H+, 346.15837; found (ESI, [M+H]+), 346.1599.

Example 4

3-[1-(3-methoxyphenyl)-2,2-dioxido-1,4-dihydro-3H-2,1,3-benzothiadiazin-3-yl]-N-methylpropan-1-amine hydrochloride

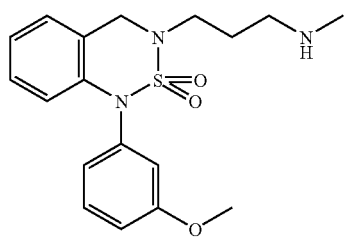

Step 1: In an analogous manner to Example 1 step 7, 3-(3-chloropropyl)-3,4-dihydro-1H-2,1,3-benzothiadiazine 2,2-dioxide (456 mg) was coupled to m-methoxyphenylboronic acid to provide 3-(3-chloropropyl)-1-(3-methoxyphenyl)-3,4-dihydro-1H-2,1,3-benzothiadiazine 2,2-dioxide (63 mg):

HPLC purity 94.2% at 210-370 nm, 10.2 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{17}H_{19}ClN_2O_3S$+H+, 367.08777; found (ESI, [M+H]+), 367.086.

Step 2: In an analogous manner to Example 1, step 8, 3-(3-chloropropyl)-1-(3-methoxyphenyl)-3,4-dihydro-1H-2,1,3-benzothiadiazine 2,2-dioxide (33 mg) was reacted with methylamine and then treated with HCl to provide 3-[1-(3-methoxyphenyl)-2,2-dioxido-1,4-dihydro-3H-2,1,3-benzothiadiazin-3-yl]-N-methylpropan-1-amine hydrochloride (21 mg):

HPLC purity 100.0% at 210-370 nm, 9.9 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{18}H_{23}N_3O_3S$+H+, 362.15329; found (ESI, [M+H]+), 362.1532.

Example 5

3-[1-(4-chlorophenyl)-2,2-dioxido-1,4-dihydro-3H-2,1,3-benzothiadiazin-3-yl]-N-methylpropan-1-amine hydrochloride

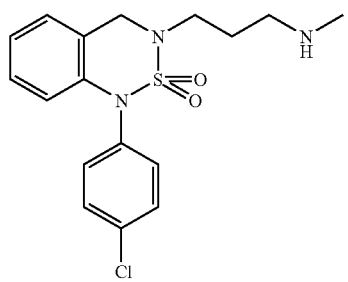

Step 1: In an analogous manner to Example 1 step 7, 3-(3-chloropropyl)-3,4-dihydro-1H-2,1,3-benzothiadiazine 2,2-dioxide (468 mg) was coupled to p-chloro phenylboronic acid to provide 1-(4-chlorophenyl)-3-(3-chloropropyl)-3,4-dihydro-1H-2,1,3-benzothiadiazine 2,2-dioxide (50 mg):

MS (ES) m/z 370.8;

HPLC purity 100.0% at 210-370 nm, 10.7 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

Step 2: In an analogous manner to Example 1, step 8, 1-(4-chlorophenyl)-3-(3-chloropropyl)-3,4-dihydro-1H-2,1, 3-benzothiadiazine 2,2-dioxide (27 mg) was reacted with methylamine and then treated with HCl to provide 3-[1-(4-chlorophenyl)-2,2-dioxido-1,4-dihydro-3H-2,1,3-benzothiadiazin-3-yl]-N-methylpropan-1-amine hydrochloride (24 mg):

HPLC purity 98.0% at 210-370 nm, 10.8 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{17}H_{20}ClN_3O_2S$+H+, 366.10375; found (ESI, [M+H]+), 366.1040.

Example 6

3-[1-(3-chloro-4-fluorophenyl)-2,2-dioxido-1,4-dihydro-3H-2,1,3-benzothiadiazin-3-yl]-N-methylpropan-1-amine hydrochloride

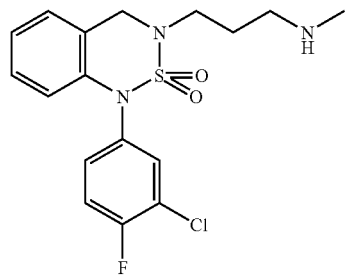

Step 1: In an analogous manner to Example 1 step 7, 3-(3-chloropropyl)-3,4-dihydro-1H-2,1,3-benzothiadiazine 2,2-dioxide (522 mg) was coupled to 3-chloro-4-fluorophenylboronic acid to provide 1-(3-chloro-4-fluorophenyl)-3-(3-chloropropyl)-3,4-dihydro-1H-2,1,3-benzothiadiazine 2,2-dioxide (138 mg):

HPLC purity 100.0% at 210-370 nm, 10.8 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{16}H_{15}Cl_2FN_2O_2S$+H+, 389.02881; found (ESI, [M+H]+), 389.0284.

Step 2: In an analogous manner to Example 1, step 8, 1-(3-chloro-4-fluorophenyl)-3-(3-chloropropyl)-3,4-dihydro-1H-2,1,3-benzothiadiazine 2,2-dioxide (73 mg) was reacted with methylamine and then treated with HCl to provide 3-[1-(3-chloro-4-fluorophenyl)-2,2-dioxido-1,4-dihydro-3H-2,1,3-benzothiadiazin-3-yl]-N-methylpropan-1-amine hydrochloride (61 mg):

HPLC purity 88.8% at 210-370 nm, 10.9 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{17}H_{19}ClFN_3O_2S$+H+, 384.09433; found (ESI, [M+H]+), 384.0937.

Example 7

3-[1-(4-fluorophenyl)-2,2-dioxido-1,4-dihydro-3H-2,1,3-benzothiadiazin-3-yl]-N-methylpropan-1-amine hydrochloride

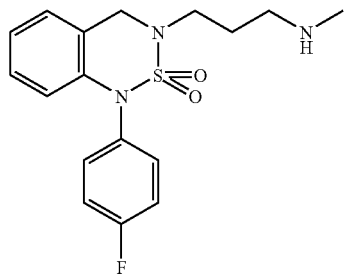

Step 1: In an analogous manner to Example 1 step 7, 3-(3-chloropropyl)-3,4-dihydro-1H-2,1,3-benzothiadiazine 2,2-dioxide (417 mg) was coupled to p-fluorophenylboronic acid to provide 3-(3-chloropropyl)-1-(4-fluorophenyl)-3,4-dihydro-1H-2,1,3-benzothiadiazine 2,2-dioxide (67 mg):

HPLC purity 100.0% at 210-370 nm, 11.6 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{16}H_{16}ClFN_2O_2S$+H+, 355.06778; found (ESI, [M+H]+), 355.0671.

Step 2: In an analogous manner to Example 1, step 8, 3-(3-chloropropyl)-1-(4-fluorophenyl)-3,4-dihydro-1H-2,1,3-benzothiadiazine 2,2-dioxide (50 mg) was reacted with methylamine and then treated with HCl to provide 3-[1-(4-fluorophenyl)-2,2-dioxido-1,4-dihydro-3H-2,1,3-benzothiadiazin-3-yl]-N-methylpropan-1-amine hydrochloride (46 mg):

HPLC purity 100.0% at 210-370 nm, 10.2 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{17}H_{20}FN_3O_2S$+H+, 350.13330; found (ESI, [M+H]+), 350.133.

Example 8

N-methyl-3-[1-(4-methylphenyl)-2,2-dioxido-1,4-dihydro-3H-2,1,3-benzothiadiazin-3-yl]propan-1-amine hydrochloride

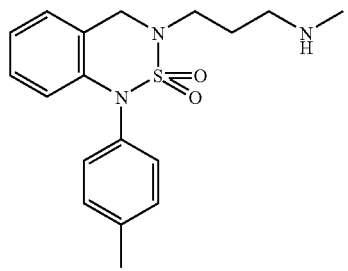

Step 1: In an analogous manner to Example 1 step 7, 3-(3-chloropropyl)-3,4-dihydro-1H-2,1,3-benzothiadiazine 2,2-dioxide (408 mg) was coupled to p-tolylboronic acid to provide 3-(3-chloropropyl)-1-(4-methylphenyl)-3,4-dihydro-1H-2,1,3-benzothiadiazine 2,2-dioxide (99 mg):

HPLC purity 100.0% at 210-370 nm, 12.0 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{17}H_{19}ClN_2O_2S$+H+, 351.09285; found (ESI, [M+H]+), 351.092.

Step 2: In an analogous manner to Example 1, step 8, 3-(3-chloropropyl)-1-(4-methylphenyl)-3,4-dihydro-1H-2,1,3-benzothiadiazine 2,2-dioxide (81 mg) was reacted with methylamine and then treated with HCl to provide N-methyl-3-[1-(4-methylphenyl)-2,2-dioxido-1,4-dihydro-3H-2,1,3-benzothiadiazin-3-yl]propan-1-amine hydrochloride (61 mg):

HPLC purity 100.0% at 210-370 nm, 10.8 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{18}H_{23}N_3O_2S$+H+, 346.15837; found (ESI, [M+H]+), 346.1595.

Example 9

3-[1-(4-methoxyphenyl)-2,2-dioxido-1,4-dihydro-3H-2,1,3-benzothiadiazin-3-yl]-N-methylpropan-1-amine hydrochloride

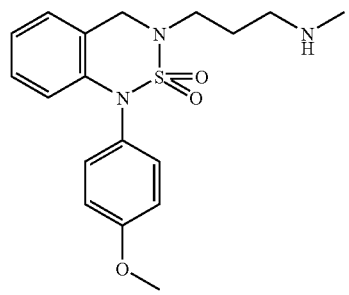

Step 1: In an analogous manner to Example 1 step 7, 3-(3-chloropropyl)-3,4-dihydro-1H-2,1,3-benzothiadiazine 2,2-dioxide (456 mg) was coupled to p-methoxyphenylboronic acid to provide 3-(3-chloropropyl)-1-(4-methoxyphenyl)-3,4-dihydro-1H-2,1,3-benzothiadiazine 2,2-dioxide (132 mg):

HPLC purity 100.0% at 210-370 nm, 11.6 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{17}H_{19}ClN_2O_3S$+H+, 367.08777; found (ESI, [M+H]+), 367.0867.

Step 2: In an analogous manner to Example 1, step 8, 3-(3-chloropropyl)-1-(4-methoxyphenyl)-3,4-dihydro-1H-2,1,3-benzothiadiazine 2,2-dioxide (105 mg) was reacted with methylamine and then treated with HCl to provide 3-[1-(4-methoxyphenyl)-2,2-dioxido-1,4-dihydro-3H-2,1,3-benzothiadiazin-3-yl]-N-methylpropan-1-amine hydrochloride (32 mg):

HPLC purity 100.0% at 210-370 nm, 10.2 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{18}H_{23}N_3O_3S$+H+, 362.15329; found (ESI, [M+H]+), 362.1548.

Example 10

3-[1-(3,4-difluorophenyl)-2,2-dioxido-1,4-dihydro-3H-2,1,3-benzothiadiazin-3-yl]-N-methylpropan-1-amine hydrochloride

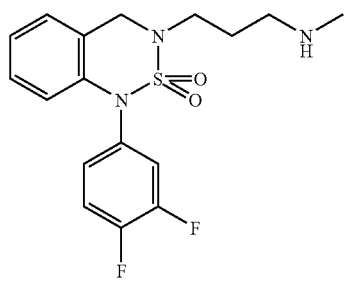

Step 1: In an analogous manner to Example 1 step 7, 3-(3-chloropropyl)-3,4-dihydro-1H-2,1,3-benzothiadiazine 2,2-dioxide (474 mg) was coupled to 3,4-difluorophenylboronic acid to provide 3-(3-chloropropyl)-1-(3,4-difluorophenyl)-3,4-dihydro-1H-2,1,3-benzothiadiazine 2,2-dioxide (92 mg):

HPLC purity 98.9% at 210-370 nm, 11.8 minutes; Xterra RP18, 3.5μ, 150×4.6 mm column, 1.2 mL/min, 85/15-5/95 (ammonium formate buffer pH=3.5/ACN+MeOH) for 10 minutes, hold 4 minutes.

HRMS: calculated for $C_{16}H_{15}ClF_2N_2O_2S+H+$, 373.05836; found (ESI, [M+H]$^+$), 373.059.

Step 2: In an analogous manner to Example 1, step 8, 3-(3-chloropropyl)-1-(3,4-difluorophenyl)-3,4-dihydro-1H-2,1,3-benzothiadiazine 2,2-dioxide (71 mg) was reacted with methylamine and then treated with HCl to provide 3-[1-(3,4-difluorophenyl)-2,2-dioxido-1,4-dihydro-3H-2,1,3-benzothiadiazin-3-yl]-N-methyl propan-1-amine hydrochloride (53 mg):

HPLC purity 95.9% at 210-370 nm, 10.6 minutes; Xterra RP18, 3.5μ, 150×4.6 mm column, 1.2 mL/min, 85/15-5/95 (ammonium bicarbonate buffer pH=9.5/ACN+MeOH) for 10 minutes, hold 4 minutes.

HRMS: calculated for $C_{17}H_{19}F_2N_3O_2S+H+$, 368.12388; found (ESI, [M+H]$^+$), 368.1237.

Example 11

2-[1-(2-fluorophenyl)-2,2-dioxido-1,4-dihydro-3H-2,1,3-benzothiadiazin-3-yl]-N-methylethanamine

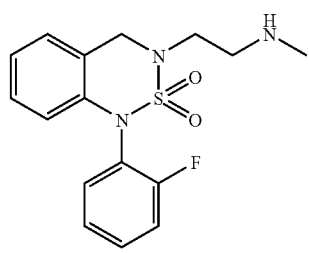

Step 1: A solution of fluoroaniline (6.8 ml, 71 mmol) in DMF (100 ml) was treated with potassium tert-butoxide (12.7 g, 113 mmol) and then with 2-fluorobenzonitrile (7.5 ml, 71 mmol) that was slowly added to the stirring reaction with a syringe and stirred at 23° C. for 16 h. The reaction mixture was diluted with H$_2$O (100 mL) and extracted with ethyl ether (3×50 mL), dried with (MgSO$_4$), and evaporated. Flash chromatography (SiO$_2$, 2-100% dichloromethane/heptane) provided 2-[(2-fluorophenyl)amino]benzonitrile (8.4 g 56%) as an orange solid:

HPLC purity 100.0% at 210-370 nm, 9.4 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{13}H_9FN_2+H+$, 213.08225; found (ESI, [M+H]$^+$), 213.0822.

Step 2: A solution of 1M Borane in THF (175 ml, 175 mmol) cooled to 0° C. in a 500 ml flack. The 2-[(2-fluorophenyl)amino]benzonitrile was added to the reaction flask in small portions and was warmed to room temperature for 15 h. The reaction mixture was evaporated and then was quenched by the addition of H$_2$O (20 mL). To the quenched reaction flask 2 N HCl (200 mL) was added and then the reaction was refluxed for 2 h. and then cooled to room temperature. The reaction mixture was transferred to an Erlenmeyer flask where 2 N NaOH (210 mL) was slowly added to the flask. The pH was checked to insure that the pH was basic. The aqueous product was extracted with dichloromethane, dried with MgSO$_4$, and evaporated. Flash chromatography (SiO$_2$, 0-10% 0.5 M NH$_3$-methanol/dichloromethane) provided 2-(aminomethyl)-N-(2-fluorophenyl)aniline (4.98 g, 67%) as a brown oil:

HPLC purity 98.5% at 210-370 nm, 5.8 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{13}H_{13}FN_2+H+$, 217.11355; found (ESI, [M+H]$^+$ Calc'd), 217.1136.

Step 3: A solution of 2-(aminomethyl)-N-(2-fluorophenyl)aniline (2.07 g, 9.6 mmol) and sulfamide (1.1 g, 11.5 mmol) in diglyme (10 mL) was added to a flask containing refluxing diglyme (15 mL) over 10 min. The reaction mixture was stirred at reflux for 1 h, then cooled to room temperature and was evaporated to a brown oil. The crude reaction product was purified by flash chromatography (SiO$_2$, 3-50% ethyl acetate/heptane) to afford 1-(2-fluorophenyl)-3,4-dihydro-1H-2,1,3-benzothiadiazine 2,2-dioxide (1.86 g, 70%) as a white solid:

HPLC purity 100.0% at 210-370 nm, 8.3 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{13}H_{11}FN_2O_2S+H+$, 279.05980; found (ESI, [M+H]+ Calc'd), 279.0598.

Step 4: A solution of 1-(2-fluorophenyl)-3,4-dihydro-1H-2,1,3-benzothiadiazine 2,2-dioxide (0.46 g, 1.7 mmol) in tetrahydrofuran (20 mL) was cool to 0° C. and treated with triphenylphosphine (0.65 g, 2.5 mmol), bromoethanol (0.25 mL, 3.5 mmol) and diisopropyl azodicarboxylate (0.5 mL, 2.6 mmol). After the final addition, the reaction mixture was warmed to room temperature for 2 h, evaporated to a brown oil. The crude product residue was purified by flash chromatography (SiO$_2$, 3-50% ethyl acetate/heptane) to afford 3-(2-bromoethyl)-1-(2-fluorophenyl)-3,4-dihydro-1H-2,1,3-benzothiadiazine 2,2-dioxide (0.44 g, 63%) as a white solid:

HPLC purity 92.5% at 210-370 nm, 10.0 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{15}H_{14}BrFN_2O_2S+H+$, 385.00161; found (ESI, [M+H]+ Calc'd), 385.0016.

Step 5: 3-(2-bromoethyl)-1-(2-fluorophenyl)-3,4-dihydro-1H-2,1,3-benzothiadiazine 2,2-dioxide (0.96 g, 0.25 mmol) was dissolved in an 8 M solution of methylamine in ethanol (4 ml) and was stirred in a capped vial at room temperature for two hours. The reaction mixture was evaporated and the residue purified by flash chromatography (SiO$_2$, 0-5% 7 M NH$_3$-methanol/dichloromethane). The purified free-base was dissolved in dichloromethane (3 mL) and treated with hydrogen chloride (1.0 mL of a 2 M solution in ethyl ether), resulting in a white precipitate that was evaporated and dried under vacuum to afford 2-[1-(2-fluorophenyl)-2,2-dioxido-1,4-dihydro-3H-2,1,3-benzothiadiazin-3-yl]-N-methylethanamine (0.071 g, 85%) as a white solid:

HPLC purity 100.0% at 210-370 nm, 6.5 min.; Xterra RP18, 3.5µ, 150×4.6 mm column, 1.2 mL/min, 85/15-5/95 (ammonium formate buffer pH 3.5/acetonitrile) gradient for 10 min, then hold for 4 min.

HRMS: calcd for C$_{16}$H$_{18}$FN$_3$O$_2$S+H+, 336.11765; found (ESI, [M+H]+ Obs'd), 336.1170.

Example 12

N-{2-[1-(2-fluorophenyl)-2,2-dioxido-1,4-dihydro-3H-2,1,3-benzothiadiazin-3-yl]ethyl}cyclopropanamine

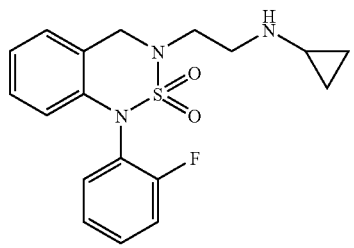

In an analogous manner to Example 11 step 5, 3-(2-bromoethyl)-1-(2-fluorophenyl)-3,4-dihydro-1H-2,1,3-benzothiadiazine 2,2-dioxide (0.96 g, 0.25 mmol) was reacted with cyclopropylamine and then treated with HCl to afford N-{2-[1-(2-fluorophenyl)-2,2-dioxido-1,4-dihydro-3H-2,1,3-benzothiadiazin-3-yl]ethyl}cyclopropanamine as a white solid:

HPLC purity 100.0% at 210-370 nm, 7.0 min.; Xterra RP18, 3.5µ, 150×4.6 mm column, 1.2 mL/min, 85/15-5/95 (ammonium formate buffer pH 3.5/acetonitrile) gradient for 10 min, then hold for 4 min.

HRMS: calcd for C$_{18}$H$_{20}$FN$_3$O$_2$S+H+, 362.13330; found (ESI, [M+H]+ Calc'd), 362.1333.

Example 13

3-[1-(2-fluorophenyl)-2,2-dioxido-1,4-dihydro-3H-2,1,3-benzothiadiazin-3-yl]-N-methylpropan-1-amine

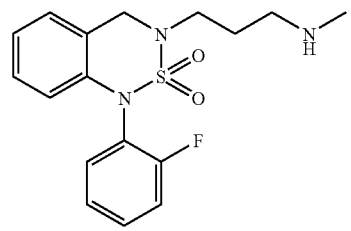

Step 1: In an analogous manner to Example 11 step 4, a solution of 1-(2-fluorophenyl)-3,4-dihydro-1H-2,1,3-benzothiadiazine 2,2-dioxide (0.49 g, 1.8 mmol) was reacted with 3-bromopropanol (0.31 mL, 3.6 mmol) to afford 3-(3-bromopropyl)-1-(2-fluorophenyl)-3,4-dihydro-1H-2,1,3-benzothiadiazine 2,2-dioxide (0.44 g, 63%) as a white solid:

HPLC purity 99.4% at 210-370 nm, 10.2 min.; Xterra RP18, 3.5µ, 150×4.6 mm column, 1.2 mL/min, 85/15-5/95 (ammonium formate buffer pH 3.5/acetonitrile) gradient for 10 min, then hold for 4 min.

HRMS: calcd for C$_{16}$H$_{16}$BrFN$_2$O$_2$S+H+, 399.01726; found (ESI, [M+H]+ Obs'd), 399.0170.

Step 2: In an analogous manner to Example 11 step 5, 3-(3-bromopropyl)-1-(2-fluorophenyl)-3,4-dihydro-1H-2,1,3-benzothiadiazine 2,2-dioxide (0.1 g, 0.23 mmol) was reacted to methylamine and then treated with HCl to provide 3-[1-(2-fluorophenyl)-2,2-dioxido-1,4-dihydro-3H-2,1,3-benzothiadiazin-3-yl]-N-methylpropan-1-amine as a white solid:

HPLC purity 98.6% at 210-370 nm, 6.8 min.; Xterra RP18, 3.5µ, 150×4.6 mm column, 1.2 mL/min, 85/15-5/95 (ammonium formate buffer pH 3.5/acetonitrile) gradient for 10 min, then hold for 4 min.

HRMS: calcd for C$_{17}$H$_{20}$FN$_3$O$_2$S+H+, 350.13330; found (ESI, [M+H]+ Obs'd), 350.1327.

Example 14

N-{3-[1-(2-fluorophenyl)-2,2-dioxido-1,4-dihydro-3H-2,1,3-benzothiadiazin-3-yl]propyl}cyclopropanamine

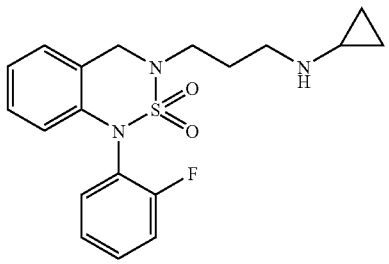

In an analogous manner to Example 11 step 5, 3-(3-bromopropyl)-1-(2-fluorophenyl)-3,4-dihydro-1H-2,1,3-benzothiadiazine 2,2-dioxide (0.1 g, 0.25 mmol) was reacted to cyclopropylamine and then treated with HCl to provide N-{3-[1-(2-fluorophenyl)-2,2-dioxido-1,4-dihydro-3H-2,1,3-benzothiadiazin-3-yl]propyl}cyclopropanamine (0.089 g, 94%) as a white solid:

HPLC purity 100.0% at 210-370 nm, 7.3 min.; Xterra RP18, 3.5µ, 150×4.6 mm column, 1.2 mL/min, 85/15-5/95 (ammonium formate buffer pH 3.5/acetonitrile) gradient for 10 min, then hold for 4 min.

HRMS: calcd for C$_{19}$H$_{22}$FN$_3$O$_2$S+H+, 376.14895; found (ESI, [M+H]+ Obs'd), 376.1487.

Example 15

4-[1-(2-fluorophenyl)-2,2-dioxido-1,4-dihydro-3H-2,1,3-benzothiadiazin-3-yl]-N-methylbutan-1-amine

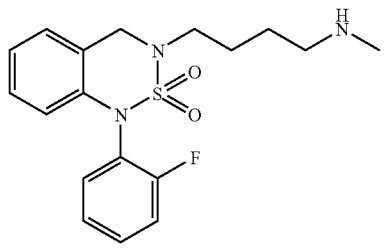

Step 1: In an analogous manner to Example 11 step 4, a solution of 1-(2-fluorophenyl)-3,4-dihydro-1H-2,1,3-benzothiadiazine 2,2-dioxide (0.75 g, 2.7 mmol) was reacted with 4-bromobutanol (0.83 mL, 5.2 mmol) to afford 3-(4-bromobutyl)-1-(2-fluorophenyl)-3,4-dihydro-1H-2,1,3-benzothiadiazine 2,2-dioxide (0.74 g, 66%) as a white solid:

HPLC purity 97.6% at 210-370 nm, 10.6 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{17}H_{18}BrFN_2O_2S+H+$, 413.03291; found (ESI, [M+H]+ Obs'd), 413.0327.

Step 2: In an analogous manner to Example 11 step 5, 3-(4-bromobutyl)-1-(2-fluorophenyl)-3,4-dihydro-1H-2,1,3-benzothiadiazine 2,2-dioxide (0.11 g, 0.26 mmol) was reacted to methylamine and then treated with HCl to provide 4-[1-(2-fluorophenyl)-2,2-dioxido-1,4-dihydro-3H-2,1,3-benzothiadiazin-3-yl]-N-methylbutan-1-amine (0.078 g, 82%) as a white solid:

HPLC purity 100.0% at 210-370 nm, 7.2 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{18}H_{22}FN_3O_2S+H+$, 364.14895; found (ESI, [M+H]+ Obs'd), 364.1482.

Example 16

N-{4-[1-(2-fluorophenyl)-2,2-dioxido-1,4-dihydro-3H-2,1,3-benzothiadiazin-3-yl]butyl}cyclopropanamine

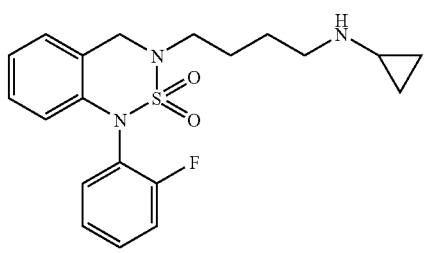

In an analogous manner to Example 11 step 5, 3-(4-bromobutyl)-1-(2-fluorophenyl)-3,4-dihydro-1H-2,1,3-benzothiadiazine 2,2-dioxide (0.11 g, 0.26 mmol) was reacted to cyclopropylamine and then treated with HCl to provide N-{4-[1-(2-fluorophenyl)-2,2-dioxido-1,4-dihydro-3H-2,1,3-benzothiadiazin-3-yl]butyl}cyclopropanamine (0.099 g, 92%) as a white solid:

HPLC purity 99.1% at 210-370 nm, 7.6 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{20}H_{24}FN_3O_2S+H+$, 390.16460; found (ESI, [M+H]+ Obs'd), 390.1640.

Example 17

2-[6-fluoro-1-(2-fluorophenyl)-2,2-dioxido-1,4-dihydro-3H-2,1,3-benzothiadiazin-3-yl]-N-methylethanamine

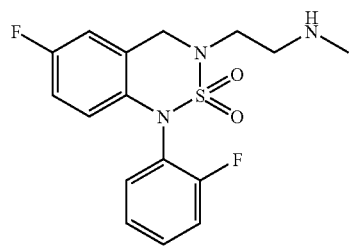

Step 1: In an analogous manner to Example 11 step 4, a solution of 6-fluoro-1-(2-fluorophenyl)-3,4-dihydro-1H-2,1,3-benzothiadiazine 2,2-dioxide (1.01 g, 3.4 mmol) was reacted with bromoethanol (0.95 mL, 13.4 mmol) to afford 3-(2-bromoethyl)-6-fluoro-1-(2-fluorophenyl)-3,4-dihydro-1H-2,1,3-benzothiadiazine 2,2-dioxide (0.943 g, 69%) as white solid:

HPLC purity 95.7% at 210-370 nm, 10.2 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

Step 2: In an analogous manner to Example 11 step 5, 3-(2-bromoethyl)-6-fluoro-1-(2-fluorophenyl)-3,4-dihydro-1H-2,1,3-benzothiadiazine 2,2-dioxide (0.1 g, 0.25 mmol) was reacted to methylamine and then treated with HCl to provide 2-[6-fluoro-1-(2-fluorophenyl)-2,2-dioxido-1,4-dihydro-3H-2,1,3-benzothiadiazin-3-yl]-N-methylethanamine (0.081 g, 92%) as a white solid:

HPLC purity 96.3% at 210-370 nm, 6.8 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{16}H_{17}F_2N_3O_2S+H+$, 354.10823; found (ESI, [M+H]+ Obs'd), 354.1078.

Example 18

N-{2-[6-fluoro-1-(2-fluorophenyl)-2,2-dioxido-1,4-dihydro-3H-2,1,3-benzothiadiazin-3-yl]ethyl}cyclopropanamine

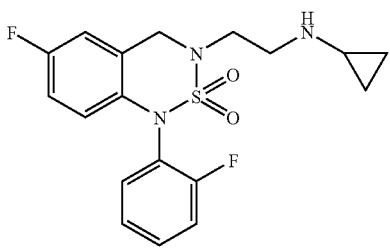

In an analogous manner to Example 11 step 5, 3-(2-bromoethyl)-6-fluoro-1-(2-fluorophenyl)-3,4-dihydro-1H-2,1,3-benzothiadiazine 2,2-dioxide (0.1 g, 0.25 mmol) was reacted to cyclopropylamine and then treated with HCl to provide N-{2-[6-fluoro-1-(2-fluorophenyl)-2,2-dioxido-1,4-dihydro-3H-2,1,3-benzothiadiazin-3-yl]ethyl}cyclopropanamine (0.099 g, 95%) as a white solid:

HPLC purity 100.0% at 210-370 nm, 7.3 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{18}H_{19}F_2N_3O_2S+H+$, 380.12388; found (ESI, [M+H]+ Obs'd), 380.1236.

Example 19

3-[6-fluoro-1-(2-fluorophenyl)-2,2-dioxido-1,4-dihydro-3H-2,1,3-benzothiadiazin-3-yl]-N-methylpropan-1-amine

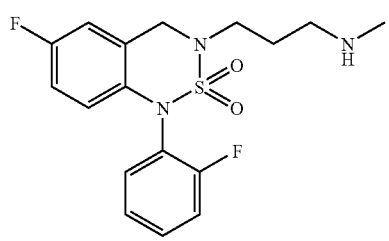

Step 1: In an analogous manner to Example 11 step 4, a solution of 6-fluoro-1-(2-fluorophenyl)-3,4-dihydro-1H-2,1,3-benzothiadiazine 2,2-dioxide (0.51 g, 1.7 mmol) was reacted with 3-bromopropanol (0.25 mL, 2.8 mmol) to afford 3-(3-bromopropyl)-6-fluoro-1-(2-fluorophenyl)-3,4-dihydro-1H-2,1,3-benzothiadiazine 2,2-dioxide (0.51 g, 71%) as a white solid:

HPLC purity 85.2% at 210-370 nm, 10.4 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

Step 2: In an analogous manner to Example 111 step 5, 3-(3-bromopropyl)-6-fluoro-1-(2-fluorophenyl)-3,4-dihydro-1H-2,1,3-benzothiadiazine 2,2-dioxide (0.1 g, 0.25 mmol) was reacted to methylamine and then treated with HCl to provide 3-[6-fluoro-1-(2-fluorophenyl)-2,2-dioxido-1,4-dihydro-3H-2,1,3-benzothiadiazin-3-yl]-N-methylpropan-1-amine (0.102 g, 68%) as a white solid:

HPLC purity 98.2% at 210-370 nm, 7.2 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{17}H_{19}F_2N_3O_2S+H+$, 368.12388; found (ESI, [M+H]+ Obs'd), 368.1230.

Example 20

N-{3-[6-fluoro-1-(2-fluorophenyl)-2,2-dioxido-1,4-dihydro-3H-2,1,3-benzothiadiazin-3-yl]propyl}cyclopropanamine

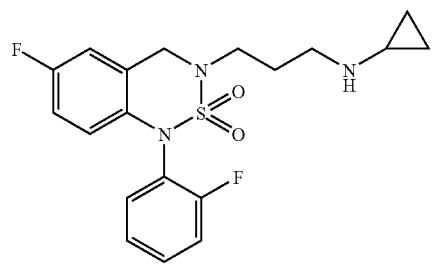

In an analogous manner to Example 11 step 5, 3-(3-bromopropyl)-6-fluoro-1-(2-fluorophenyl)-3,4-dihydro-1H-2,1,3-benzothiadiazine 2,2-dioxide (0.1 g, 0.25 mmol) was reacted to cyclopropylamine and then treated with HCl to provide N-{3-[6-fluoro-1-(2-fluorophenyl)-2,2-dioxido-1,4-dihydro-3H-2,1,3-benzothiadiazin-3-yl]propyl}cyclopropanamine (0.102 g, 96%) as a white solid:

HPLC purity 100.0% at 210-370 nm, 7.6 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{19}H_{21}F_2N_3O_2S+H+$, 394.13953; found (ESI, [M+H]+ Obs'd), 394.1388.

Example 21

4-[6-fluoro-1-(2-fluorophenyl)-2,2-dioxido-1,4-dihydro-3H-2,1,3-benzothiadiazin-3-yl]-N-methylbutan-1-amine

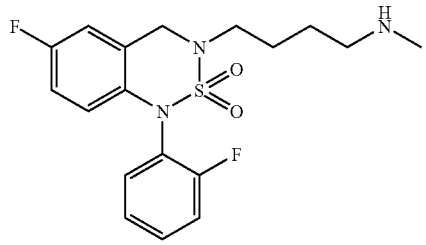

Step 1: In an analogous manner to Example 11 step 4, a solution of 6-fluoro-1-(2-fluorophenyl)-3,4-dihydro-1H-2,1,3-benzothiadiazine 2,2-dioxide (0.51 g, 1.7 mmol) was reacted with 4-bromobutanol (0.53 mL, 3.4 mmol) to afford 3-(4-bromobutyl)-6-fluoro-1-(2-fluorophenyl)-3,4-dihydro-1H-2,1,3-benzothiadiazine 2,2-dioxide (0.55 g, 74%) as a white solid:

HPLC purity 95.1% at 210-370 nm, 10.7 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

Step 2: In an analogous manner to Example 11 step 5, 3-(4-bromobutyl)-6-fluoro-1-(2-fluorophenyl)-3,4-dihydro-1H-2,1,3-benzothiadiazine 2,2-dioxide (0.11 g, 0.25 mmol) was reacted to methylamine and then treated with HCl to provide 4-[6-fluoro-1-(2-fluorophenyl)-2,2-dioxido-1,4-dihydro-3H-2,1,3-benzothiadiazin-3-yl]-N-methylbutan-1-amine (0.085 g, 81%) as a white solid:

HPLC purity 100.0% at 210-370 nm, 7.5 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{18}H_{21}F_2N_3O_2S+H+$, 382.13953; found (ESI, [M+H]+ Obs'd), 382.1384.

Example 22

N-{4-[6-fluoro-1-(2-fluorophenyl)-2,2-dioxido-1,4-dihydro-3H-2,1,3-benzothiadiazin-3-yl]butyl}cyclopropanamine

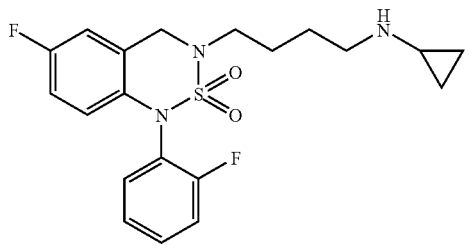

In an analogous manner to Example 11 step 5, 3-(4-bromobutyl)-6-fluoro-1-(2-fluorophenyl)-3,4-dihydro-1H-2,1,3-benzothiadiazine 2,2-dioxide (0.11 g, 0.25 mmol) was reacted to cyclopropylamine and then treated with HCl to provide N-{4-[6-fluoro-1-(2-fluorophenyl)-2,2-dioxido-1,4-dihydro-3H-2,1,3-benzothiadiazin-3-yl]butyl}cyclopropanamine (0.094 g, 85%) as a white solid:

HPLC purity 100.0% at 210-370 nm, 7.8 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{20}H_{23}F_2N_3O_2S+H+$, 408.15518; found (ESI, [M+H]+ Obs'd), 408.1541.

Example 23

(2S)-4-[6-fluoro-1-(2-fluorophenyl)-2,2-dioxido-1,4-dihydro-3H-2,1,3-benzothiadiazin-3-yl]-1-(methylamino)butan-2-ol

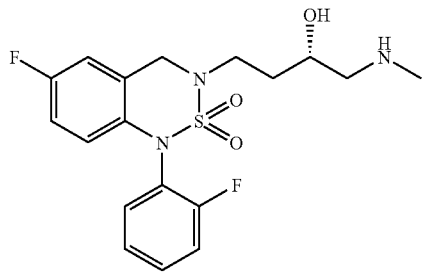

Step 1: A solution 6-fluoro-1-(2-fluorophenyl)-3,4-dihydro-1H-2,1,3-benzothiadiazine 2,2-dioxide (0.13 g, 0.29 mmol) in acetone (3 mL) was treated with potassium carbonate (0.11 g, 0.81 mmol), (S)-(−)-4-Bromo-1,2-epoxybutane (0.14 mL, 1.41 mmol) and was heated to 45° C. for two h then at room temperature for 14 h. The reaction mixture was diluted with ethyl ether (40 mL) and washed with sat. sodium bicarbonate (2×20 mL), the organic layer was isolated, dried with MgSO₄ and evaporated. The crude reaction product was purified by flash chromatography (SiO₂, 3-50% ethyl acetate/heptane) to provided 6-fluoro-1-(2-fluorophenyl)-3-{2-[(2S)-oxiran-2-yl]ethyl}-3,4-dihydro-1H-2,1,3-benzothiadiazine 2,2-dioxide (0.17 g, 67%) as a white solid.

HPLC purity No impurity was detected at 210-370 nm; Xterra RP18, 3.5μ, 150×4.6 mm column, 1.2 mL/min, A: 10 mM AmmoniumFormate in water (ph 3.5); B: 50:50 ACN:MeOH.

HRMS: calcd for $C_{17}H_{16}F_2N_2O_3S+H+$, 367.09224; found (ESI, [M+H]+ Obs'd), 367.0922.

Step 2: 6-fluoro-1-(2-fluorophenyl)-3-{2-[(2S)-oxiran-2-yl]ethyl}-3,4-dihydro-1H-2,1,3-benzothiadiazine 2,2-dioxide (0.12 g, 0.29 mmol) was dissolved in an 8 M solution of methylamine in ethanol (3 mL, 24 mmol) and was heated to 100° C. for 192 sec. in the microwave. The reaction mixture was evaporated and the residue purified by flash chromatography (SiO₂, 0-5% 7 M NH₃-methanol/dichloromethane). The purified free-base was dissolved in dichloromethane (3 mL) and treated with hydrogen chloride (1.0 mL of a 2 M solution in ethyl ether), resulting in a white precipitate that was evaporated and dried under vacuum to provide (2S)-4-[6-fluoro-1-(2-fluorophenyl)-2,2-dioxido-1,4-dihydro-3H-2,1,3-benzothiadiazin-3-yl]-1-(methylamino)butan-2-ol (0.10 g. 83%) as a white solid.

HPLC purity No impurity was detected at 210-370 nm; Xterra RP18, 3.5μ, 150×4.6 mm column, 1.2 mL/min, A: 10 mM AmmoniumFormate in water (ph 3.5); B: 50:50 ACN:MeOH.

HRMS: calcd for $C_{18}H_{21}F_2N_3O_3S+H+$, 398.13444; found (ESI, [M+H]+ Obs'd), 398.1352.

Example 24

(2S)-4-[1-(2-fluorophenyl)-2,2-dioxido-1,4-dihydro-3H-2,1,3-benzothiadiazin-3-yl]-1-(methylamino)butan-2-ol

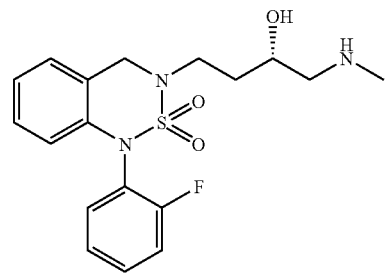

Step 1: A solution of 1-(2-fluorophenyl)-3,4-dihydro-1H-2,1,3-benzothiadiazine 2,2-dioxide (0.20 g, 0.72 mmol) in acetone (3 mL) was treated with potassium carbonate (0.11 g, 0.81 mmol), (S)-(−)-4-Bromo-1,2-epoxybutane (0.15 mL, 1.46 mmol) and was heated to 40° C. for two h then at room temperature for 14 h. The reaction mixture was diluted with ethyl ether (40 mL) and washed with 2 N sodium hydroxide (2×20 mL), the organic layer was isolated, dried with MgSO₄ and evaporated. The crude reaction product was purified by flash chromatography (SiO$_2$, 3-50% ethyl acetate/heptane) to provided 1-(2-fluorophenyl)-3-{2-[(2S)-oxiran-2-yl]ethyl}-3,4-dihydro-1H-2,1,3-benzothiadiazine 2,2-dioxide (0.22 g, 86%) as a white solid.

HPLC purity No impurity was detected at 210-370 nm; Xterra RP18, 3.5μ, 150×4.6 mm column, 1.2 mL/min, A: 10 mM AmmoniumFormate in water (ph 3.5); B: 50:50 ACN:MeOH.

HRMS: calcd for C$_{17}$H$_{17}$FN$_2$O$_3$S+H+, 349.10167; found (ESI, [M+H]+ Obs'd), 349.1017.

Step 2: 1-(2-fluorophenyl)-3-{2-[(2S)-oxiran-2-yl]ethyl}-3,4-dihydro-1H-2,1,3-benzothiadiazine 2,2-dioxide (0.12 g, 0.29 mmol) was dissolved in an 8 M solution of methylamine in ethanol (3 mL, 24 mmol) and was heated to 100° C. for 192 sec. in the microwave. The reaction mixture was evaporated and the residue purified by flash chromatography (SiO$_2$, 0-5% 7 M NH$_3$-methanol/dichloromethane). The purified free-base was dissolved in dichloromethane (3 mL) and treated with hydrogen chloride (1.0 mL of a 2 M solution in ethyl ether), resulting in a white precipitate that was evaporated and dried under vacuum to provide (2S)-4-[1-(2-fluorophenyl)-2,2-dioxido-1,4-dihydro-3H-2,1,3-benzothiadiazin-3-yl]-1-(methylamino)butan-2-ol (0.10 g, 80%) as a white solid.

HPLC purity One or more impurities are detected at 210-370 nm; Xterra RP18, 3.5μ, 150×4.6 mm column, 1.2 mL/min, A: 10 mM Ammonium Formate in water (ph 3.5); B: 50:50 ACN:MeOH.

HRMS: calcd for C$_{18}$H$_{22}$FN$_3$O$_3$S+H+, 380.14387; found (ESI, [M+H]+ Obs'd), 380.1445.

Example 25

3-[3-(2-fluorophenyl)-2,2-dioxido-3,4-dihydro-1H-2,1,3-benzothiadiazin-1-yl]-N-methylpropan-1-amine

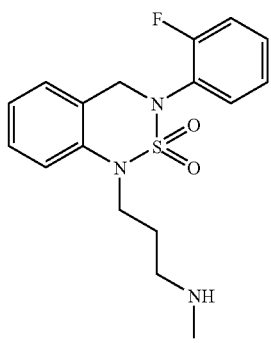

Step 1: A solution of 2-fluoroaniline (6.8 mL, 70 mmol) in tetrahydrofuran (200 mL) was cooled to −78° C. and treated with n-butyllithium (31 mL of a 2.5 M solution in hexanes, 77 mmol). After 1 h, the reaction mixture was treated with a solution of 2-nitrobenzylbromide (15.1 g, 70 mL) in tetrahydrofuran (50 mL), and warmed to room temperature and stirred for 16 h. The reaction mixture was diluted with ethyl ether (500 mL), and washed with H$_2$O (500 mL), and evaporated. Flash chromatography (SiO$_2$, 5-20% ethyl acetate/hexanes) provided 2-fluoro-N-(2-nitrobenzyl)aniline (13.4 g) as a yellow solid:

MS (ES) m/z 247.1;

HPLC purity 100.0% at 210-370 nm, 10.0 min.; Xterra RP18, 3.5μ, 150×4.6 mm column, 1.2 mL/min, 85/15-5/95 (Ammon. Form. Buff. Ph=3.5/ACN+MeOH) for 10 min, hold 4 min.

Step 2: A solution of 2-fluoro-N-(2-nitrobenzyl)aniline (9.8 g, 40 mmol) in ethanol (200 mL) was treated with a solution of ammonium chloride (11 g, 66 mmol) in H$_2$O (200 mL) and zinc dust (40 g, 66 mmol), and the reaction mixture was stirred at 50° C. for 2 h. The reaction mixture was filtered, diluted with ethyl ether (1 L), washed with H$_2$O (1 L) and evaporated to provide N-(2-aminobenzyl)-2-fluoroaniline (8 g) as a pink solid:

MS (ESI) m/z 217;

HPLC purity 98.3% at 210-370 nm, 9.0 min.; Xterra RP18, 3.5μ, 150×4.6 mm column, 1.2 mL/min, 85/15-5/95 (Ammon. Form. Buff. Ph=3.5/ACN+MeOH) for 10 min, hold 4 min.

Step 3: A solution of N-(2-aminobenzyl)-2-fluoroaniline (4.3 g, 20 mmol) in diglyme (50 mL) was treated with sulfamide (2.5 g, 26 mmol) and heated to reflux for 0.5 h. The reaction mixture was evaporated and the oily residue purified by flash chromatography (SiO$_2$, 10-100% ethyl acetate/hexanes) to provide 3-(2-fluorophenyl)-3,4-dihydro-1H-2,1,3-benzothiadiazine 2,2-dioxide (3.0 g) as a tan solid:

MS (ES) m/z 279.0;

HPLC purity 89.9% at 210-370 nm, 8.5 min.; Xterra RP18, 3.5μ, 150×4.6 mm column, 1.2 mL/min, 85/15-5/95 (Ammon. Form. Buff. Ph=3.5/ACN+MeOH) for 10 min, hold 4 min.

Step 4: 3-(2-fluorophenyl)-3,4-dihydro-1H-2,1,3-benzothiadiazine 2,2-dioxide (0.25 g, 0.9 mmol), 3-bromopropanol (0.094 mL, 1.1 mmol), diisopropylazodicarboxylate (0.21 mL, 1.08 mmol), and triphenylphosphine (0.28 g, 1.08 mol) in tetrahydrofuran (3 mL) were stirred at room temperature for 16 hours. The reaction was poured into saturated aqueous sodium chloride (20 mL) and extracted with ethyl acetate. The organics were dried over anhydrous sodium sulfate and concentrated on silica gel (0-100° C. ethyl acetate/hexane) to provide 1-(3-bromopropyl)-3-(2-fluorophenyl)-3,4-dihydro-1H-2,1,3-benzothiadiazine 2,2-dioxide (0.17 g, 47%) as a yellow solid:

MS (ESI) m/z 399;

HPLC purity 77.3% at 210-370 nm, 10.2 min.; Xterra RP18, 3.5μ, 150×4.6 mm column, 1.2 mL/min, 85/15-5/95 (Ammon. Form. Buff. Ph=3.5/ACN+MeOH) for 10 min, hold 4 min.

Step 5: 1-(3-bromopropyl)-3-(2-fluorophenyl)-3,4-dihydro-1H-2,1,3-benzothiadiazine 2,2-dioxide (0.15 g, 0.38 mmol) and an 33% MeNH$_2$ in MeOH (15 mL) was stirred in a sealed tube at room temperature for 16 hours. The reaction was poured into saturated aqueous sodium bicarbonate (20 mL), extracted with ethyl acetate (20 mL), and dried over anhydrous sodium sulfate. The organics were concentrated onto silica gel. Purification via Isco (0-100% dichloromethane containing 15% ammonia in methanol/dichloromethane) followed by treatment with 1 N hydrochloric acid in ether gave 3-[3-(2-fluorophenyl)-2,2-dioxido-3,4-dihydro-1H-2,1,3-benzothiadiazin-1-yl]-N-methylpropan-1-amine (0.056 g, 40%) as an off-white amorphous solid:

HPLC purity 100.0% at 210-370 nm, 6.6 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for C$_{17}$H$_{20}$FN$_3$O$_2$S+H$^+$, 350.13330; found (ESI, [M+H]$^+$ Obs'd), 350.1337.

Example 26

2-[3-(2-fluorophenyl)-2,2-dioxido-3,4-dihydro-1H-2,1,3-benzothiadiazin-1-yl]-N-methylethanamine

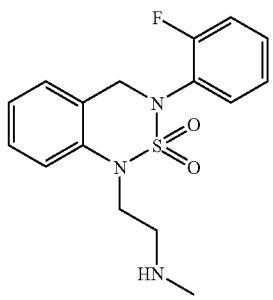

Step 1: In an analogous manner to example 25, step 4, 3-(2-fluorophenyl)-3,4-dihydro-1H-2,1,3-benzothiadiazine 2,2-dioxide (0.24 g, 0.86 mmol) was treated with 2-bromobutanol (0.073 mL g, 1.0 mmol) to give 1-(2-bromoethyl)-3-(2-fluorophenyl)-3,4-dihydro-1H-2,1,3-benzothiadiazine 2,2-dioxide (0.16 g, 48%).

Step 2: In an analogous manner to example 25, step 5, 1-(2-bromoethyl)-3-(2-fluorophenyl)-3,4-dihydro-1H-2,1,3-benzothiadiazine 2,2-dioxide (0.16 g, 0.4 mmol) was treated with 33% MeNH$_2$ in MeOH (15 mL). Treatment with 1 N hydrochloric acid in ether gave 2-[3-(2-fluorophenyl)-2,2-dioxido-3,4-dihydro-1H-2,1,3-benzothiadiazin-1-yl]-N-methylethanamine (0.065 g, 42%) as a yellow solid:

HPLC purity 100.0% at 210-370 nm, 6.3 min.; Xterra RP18, 3.5μ, 150×4.6 mm column, 1.2 mL/min, 85/15-5/95 (ammonium formate buffer pH 3.5/acetonitrile) gradient for 10 min, then hold for 4 min.

HRMS: calcd for $C_{16}H_{18}FN_3O_2S+H^+$, 336.11765; found (ESI, $[M+H]^+$ Obs'd), 336.1181.

In a manner analogous to Example 11, Steps 1-5, the following compounds are prepared:

Example 27

4-[1-phenyl-2,2-dioxido-1,4-dihydro-3H-2,1,3-benzothiadiazin-3-yl]-N-methylbutan-1-amine

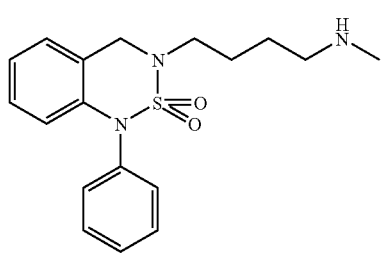

Example 28

4-[1-(2,6-difluorophenyl)-2,2-dioxido-1,4-dihydro-3H-2,1,3-benzothiadiazin-3-yl]-N-methylbutan-1-amine

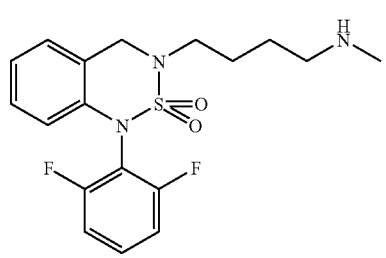

Example 29

4-[1-(2-fluoro-4-methylphenyl)-2,2-dioxido-1,4-dihydro-3H-2,1,3-benzothiadiazin-3-yl]-N-methylbutan-1-amine

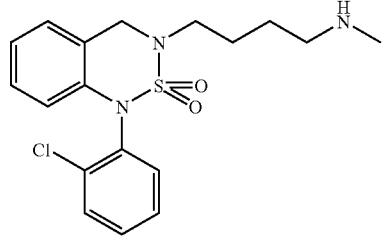

Example 30

4-[1-(2-chlorophenyl)-2,2-dioxido-1,4-dihydro-3H-2,1,3-benzothiadiazin-3-yl]-N-methylbutan-1-amine

Example 31

4-[1-(2,4,6-trifluorophenyl)-2,2-dioxido-1,4-dihydro-3H-2,1,3-benzothiadiazin-3-yl]-N-methylbutan-1-amine

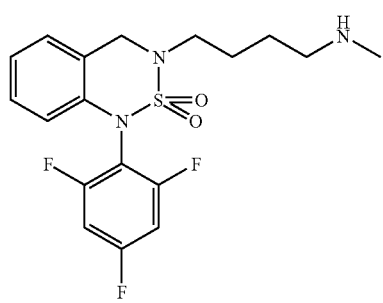

Example 32

4-[6-fluoro-1-phenyl-2,2-dioxido-1,4-dihydro-3H-2,1,3-benzothiadiazin-3-yl]-N-methylbutan-1-amine

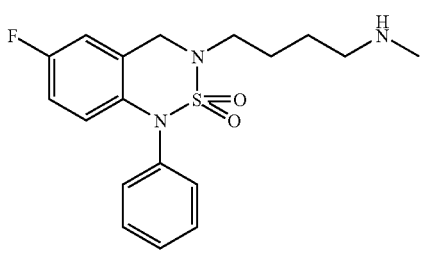

Example 33

4-[6-fluoro-1-(2,6-difluorophenyl)-2,2-dioxido-1,4-dihydro-3H-2,1,3-benzothiadiazin-3-yl]-N-methylbutan-1-amine

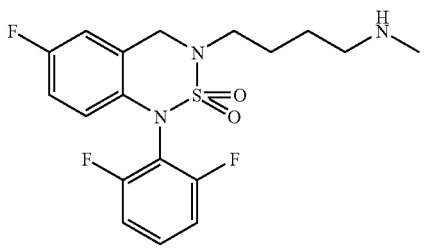

Example 34

4-[6-fluoro-1-(2-chlorophenyl)-2,2-dioxido-1,4-dihydro-3H-2,1,3-benzothiadiazin-3-yl]-N-methylbutan-1-amine

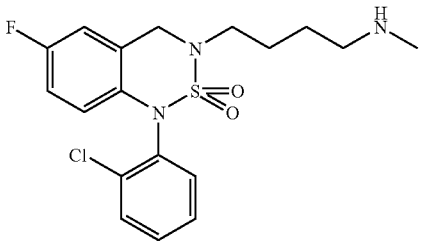

Example 35

4-[6-fluoro-1-(2-fluoro-4-methylphenyl)-2,2-dioxido-1,4-dihydro-3H-2,1,3-benzothiadiazin-3-yl]-N-methylbutan-1-amine

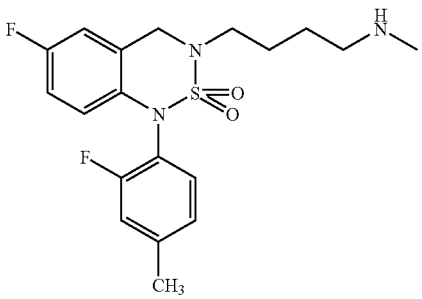

Example 36

4-[6-fluoro-1-(2,4,6-trifluorophenyl)-2,2-dioxido-1,4-dihydro-3H-2,1,3-benzothiadiazin-3-yl]-N-methylbutan-1-amine

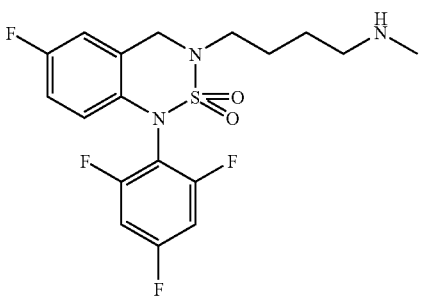

Example 37

4-[6-chloro-1-phenyl-2,2-dioxido-1,4-dihydro-3H-2,1,3-benzothiadiazin-3-yl]-N-methylbutan-1-amine

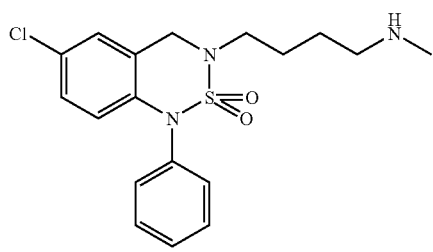

Example 38

4-[6-chloro-1-(2-fluorophenyl)-2,2-dioxido-1,4-dihydro-3H-2,1,3-benzothiadiazin-3-yl]-N-methylbutan-1-amine

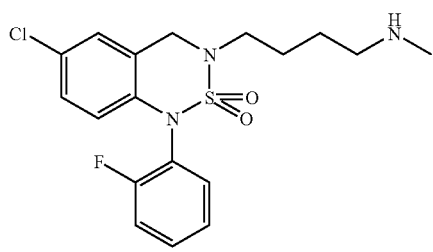

Example 39

4-[6-chloro-1-(2,6-difluorophenyl)-2,2-dioxido-1,4-dihydro-3H-2,1,3-benzothiadiazin-3-yl]-N-methylbutan-1-amine

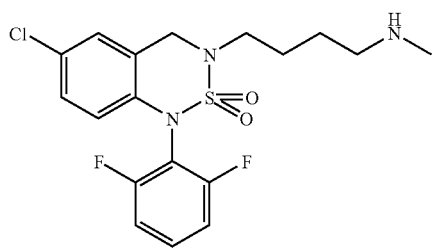

Example 40

4-[6-chloro-1-(2-fluoro-4-methylphenyl)-2,2-dioxido-1,4-dihydro-3H-2,1,3-benzothiadiazin-3-yl]-N-methylbutan-1-amine

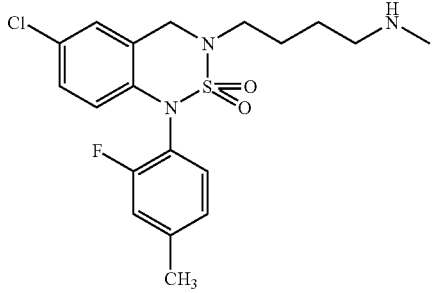

Example 41

4-[6-chloro-1-(2-chlorophenyl)-2,2-dioxido-1,4-dihydro-3H-2,1,3-benzothiadiazin-3-yl]-N-methylbutan-1-amine

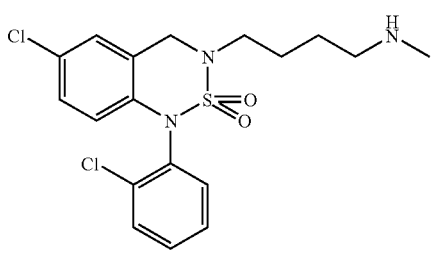

Example 42

4-[6-chloro-1-(2,4,6-trifluorophenyl)-2,2-dioxido-1,4-dihydro-3H-2,1,3-benzothiadiazin-3-yl]-N-methylbutan-1-amine

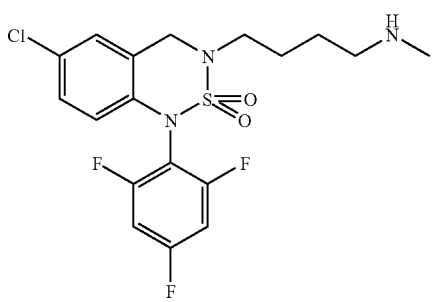

Example 43

4-[6-methyl-1-phenyl-2,2-dioxido-1,4-dihydro-3H-2,1,3-benzothiadiazin-3-yl]-N-methylbutan-1-amine

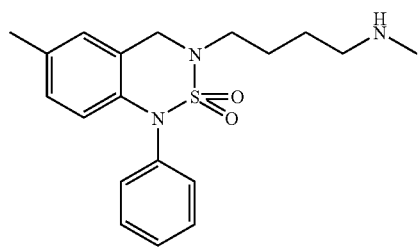

Example 44

4-[6-methyl-1-(2-fluorophenyl)-2,2-dioxido-1,4-dihydro-3H-2,1,3-benzothiadiazin-3-yl]-N-methylbutan-1-amine

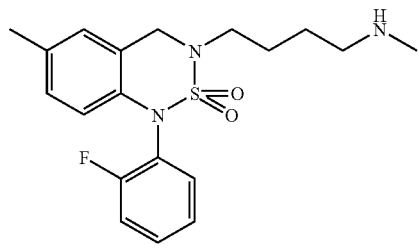

Example 45

4-[6-methyl-1-(2,6-difluorophenyl)-2,2-dioxido-1,4-dihydro-3H-2,1,3-benzothiadiazin-3-yl]-N-methylbutan-1-amine

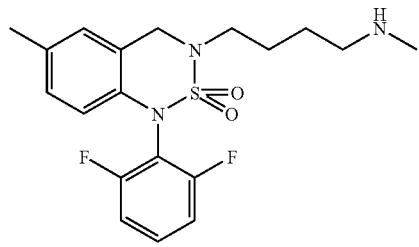

Example 46

4-[6-methyl-1-(2-fluoro-4-methylphenyl)-2,2-dioxido-1,4-dihydro-3H-2,1,3-benzothiadiazin-3-yl]-N-methylbutan-1-amine

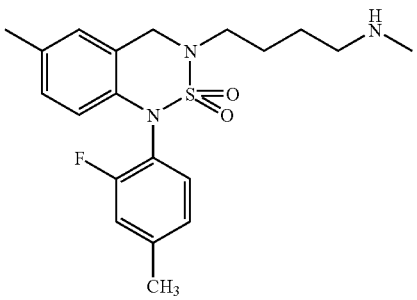

Example 47

4-[6-methyl-1-(2-chlorophenyl)-2,2-dioxido-1,4-dihydro-3H-2,1,3-benzothiadiazin-3-yl]-N-methylbutan-1-amine

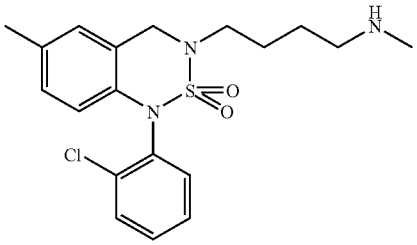

Example 48

4-[6-methyl-1-(2,4,6-trifluorophenyl)-2,2-dioxido-1,4-dihydro-3H-2,1,3-benzothiadiazin-3-yl]-N-methylbutan-1-amine

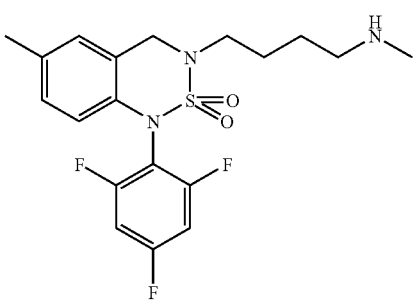

Example 49

4-[6-cyano-1-phenyl-2,2-dioxido-1,4-dihydro-3H-2,1,3-benzothiadiazin-3-yl]-N-methylbutan-1-amine

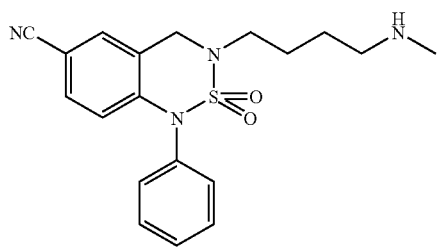

Example 50

4-[6-cyano-1-(2-fluorophenyl)-2,2-dioxido-1,4-dihydro-3H-2,1,3-benzothiadiazin-3-yl]-N-methylbutan-1-amine

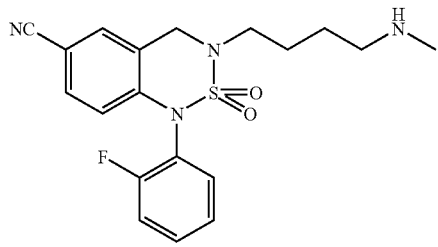

Example 51

4-[6-cyano-1-(2,6-difluorophenyl)-2,2-dioxido-1,4-dihydro-3H-2,1,3-benzothiadiazin-3-yl]-N-methylbutan-1-amine

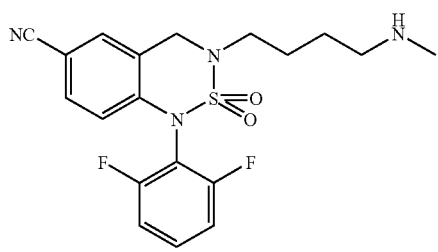

Example 52

4-[6-cyano-1-(2-fluoro-4-methylphenyl)-2,2-dioxido-1,4-dihydro-3H-2,1,3-benzothiadiazin-3-yl]-N-methylbutan-1-amine

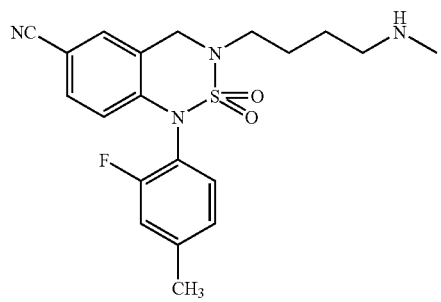

Example 53

4-[6-cyano-1-(2-chlorophenyl)-2,2-dioxido-1,4-dihydro-3H-2,1,3-benzothiadiazin-3-yl]-N-methylbutan-1-amine

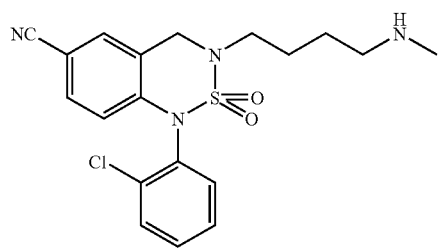

Example 54

4-[6-cyano-1-(2,4,6-trifluorophenyl)-2,2-dioxido-1,4-dihydro-3H-2,1,3-benzothiadiazin-3-yl]-N-methylbutan-1-amine

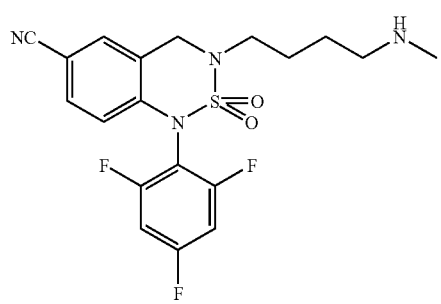

Example 55

4-[1-(2,6-difluorophenyl)-2,2-dioxido-1,4-dihydro-3H-2,1,3-benzothiadiazin-3-yl]-N-methylpropan-1-amine

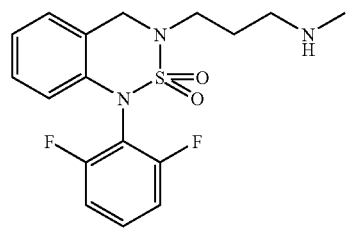

Example 56

4-[1-(2-fluoro-4-methylphenyl)-2,2-dioxido-1,4-dihydro-3H-2,1,3-benzothiadiazin-3-yl]-N-methylpropan-1-amine

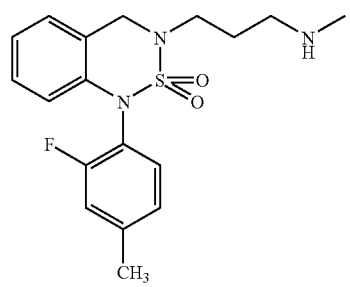

Example 57

4-[1-(2-chlorophenyl)-2,2-dioxido-1,4-dihydro-3H-2,1,3-benzothiadiazin-3-yl]-N-methylpropan-1-amine

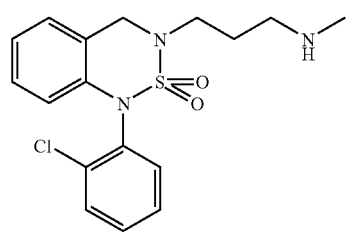

Example 58

4-[1-(2,4,6-trifluorophenyl)-2,2-dioxido-1,4-dihydro-3H-2,1,3-benzothiadiazin-3-yl]-N-methylpropan-1-amine

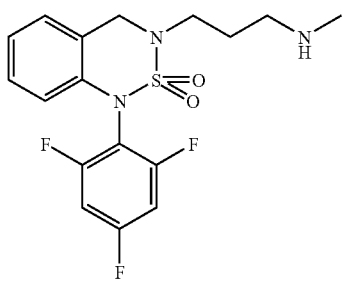

Example 59

4-[6-fluoro-1-phenyl-2,2-dioxido-1,4-dihydro-3H-2,1,3-benzothiadiazin-3-yl]-N-methylpropan-1-amine

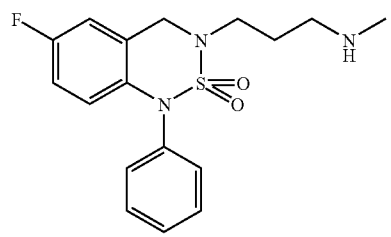

Example 60

4-[6-fluoro-1-(2,6-difluorophenyl)-2,2-dioxido-1,4-dihydro-3H-2,1,3-benzothiadiazin-3-yl]-N-methylpropan-1-amine

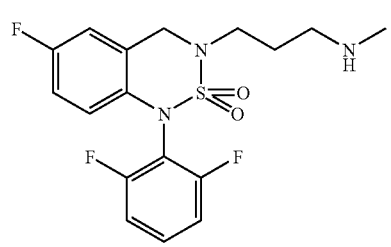

Example 61

4-[6-fluoro-1-(2-fluoro-4-methylphenyl)-2,2-dioxido-1,4-dihydro-3H-2,1,3-benzothiadiazin-3-yl]-N-methylpropan-1-amine

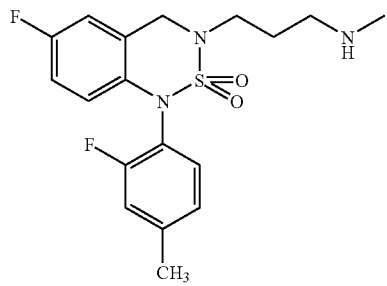

Example 62

4-[6-fluoro-1-(2-chlorophenyl)-2,2-dioxido-1,4-dihydro-3H-2,1,3-benzothiadiazin-3-yl]-N-methylpropan-1-amine

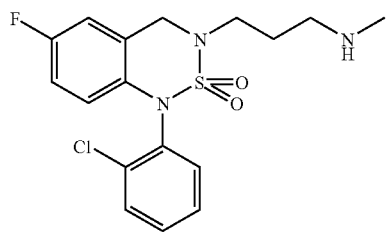

Example 63

4-[6-fluoro-1-(2,4,6-trifluorophenyl)-2,2-dioxido-1,4-dihydro-3H-2,1,3-benzothiadiazin-3-yl]-N-methylpropan-1-amine

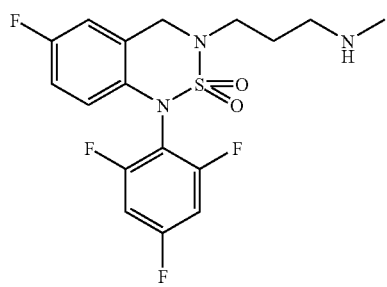

Example 64

4-[6-chloro-1-phenyl-2,2-dioxido-1,4-dihydro-3H-2,1,3-benzothiadiazin-3-yl]-N-methylpropan-1-amine

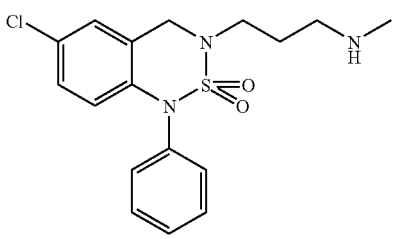

Example 65

4-[6-chloro-1-(2-fluorophenyl)-2,2-dioxido-1,4-dihydro-3H-2,1,3-benzothiadiazin-3-yl]-N-methylpropan-1-amine

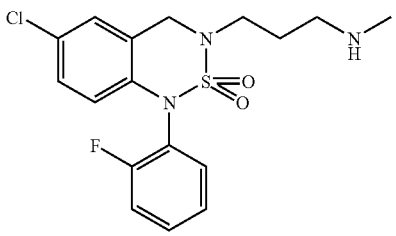

Example 66

4-[6-chloro-1-(2,6-difluorophenyl)-2,2-dioxido-1,4-dihydro-3H-2,1,3-benzothiadiazin-3-yl]-N-methylpropan-1-amine

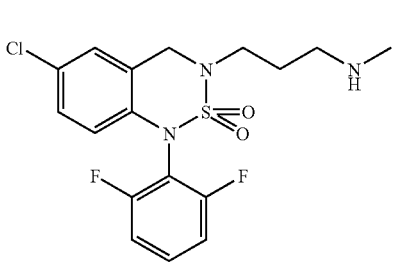

Example 67

4-[6-chloro-1-(2-fluoro-4-methylphenyl)-2,2-dioxido-1,4-dihydro-3H-2,1,3-benzothiadiazin-3-yl]-N-methylpropan-1-amine

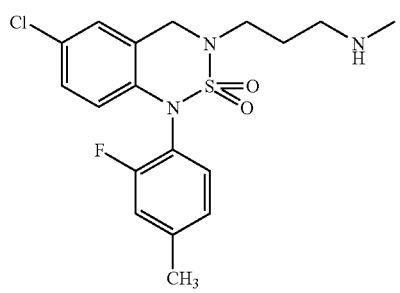

Example 68

4-[6-chloro-1-(2-chlorophenyl)-2,2-dioxido-1,4-dihydro-3H-2,1,3-benzothiadiazin-3-yl]-N-methyl-propan-1-amine

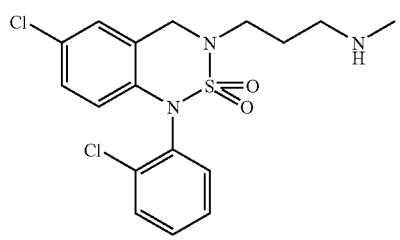

Example 69

4-[6-chloro-1-(2,4,6-trifluorophenyl)-2,2-dioxido-1,4-dihydro-3H-2,1,3-benzothiadiazin-3-yl]-N-methyl-propan-1-amine

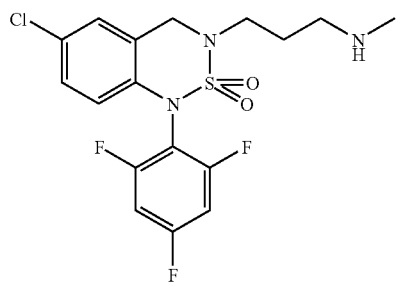

Example 70

4-[6-methyl-1-phenyl-2,2-dioxido-1,4-dihydro-3H-2,1,3-benzothiadiazin-3-yl]-N-methylpropan-1-amine

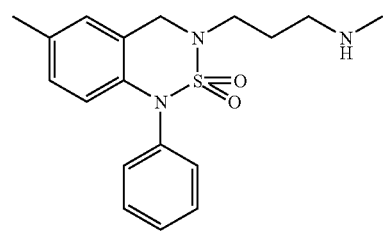

Example 71

4-[6-methyl-1-(2-fluorophenyl)-2,2-dioxido-1,4-dihydro-3H-2,1,3-benzothiadiazin-3-yl]-N-methyl-propan-1-amine

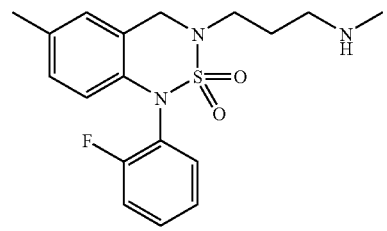

Example 72

4-[6-methyl-1-(2,6-difluorophenyl)-2,2-dioxido-1,4-dihydro-3H-2,1,3-benzothiadiazin-3-yl]-N-methyl-propan-1-amine

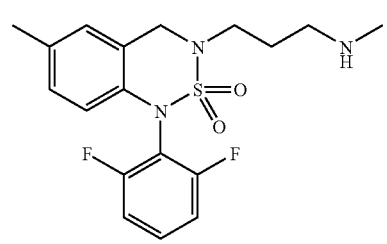

Example 73

4-[6-methyl-1-(2-fluoro-4-methylphenyl)-2,2-di-oxido-1,4-dihydro-3H-2,1,3-benzothiadiazin-3-yl]-N-methylpropan-1-amine

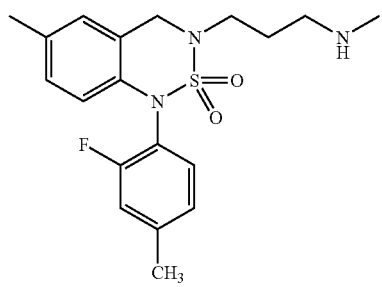

Example 74

4-[6-methyl-1-(2-chlorophenyl)-2,2-dioxido-1,4-dihydro-3H-2,1,3-benzothiadiazin-3-yl]-N-methyl-propan-1-amine

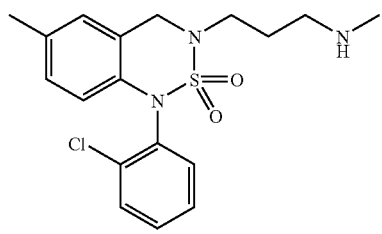

Example 75

4-[6-methyl-1-(2,4,6-trifluorophenyl)-2,2-dioxido-1,4-dihydro-3H-2,1,3-benzothiadiazin-3-yl]-N-methyl-propan-1-amine

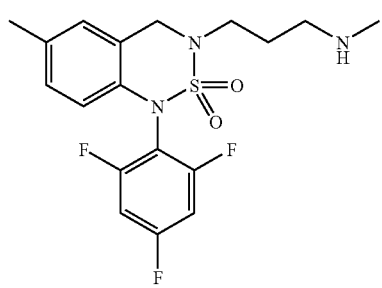

Example 76

4-[6-cyano-1-phenyl-2,2-dioxido-1,4-dihydro-3H-2,1,3-benzothiadiazin-3-yl]-N-methylpropan-1-amine

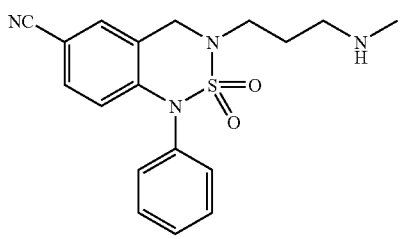

Example 77

4-[6-cyano-1-(2-fluorophenyl)-2,2-dioxido-1,4-dihydro-3H-2,1,3-benzothiadiazin-3-yl]-N-methylpropan-1-amine

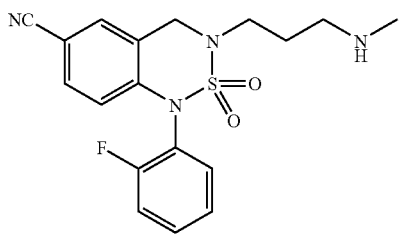

Example 78

4-[6-cyano-1-(2,6-difluorophenyl)-2,2-dioxido-1,4-dihydro-3H-2,1,3-benzothiadiazin-3-yl]-N-methyl-propan-1-amine

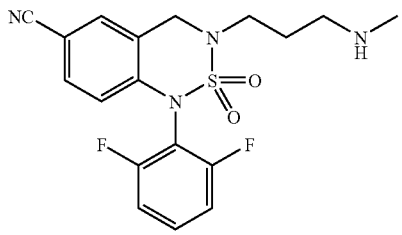

Example 79

4-[6-cyano-1-(2-fluoro-4-methylphenyl)-2,2-di-oxido-1,4-dihydro-3H-2,1,3-benzothiadiazin-3-yl]-N-methylpropan-1-amine

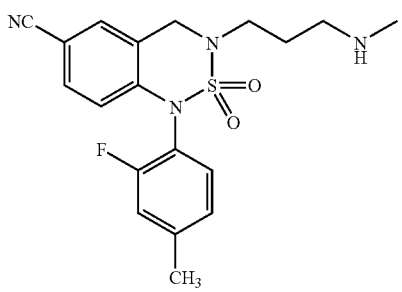

Example 80

4-[6-cyano-1-(2-chlorophenyl)-2,2-dioxido-1,4-dihydro-3H-2,1,3-benzothiadiazin-3-yl]-N-methylpropan-1-amine

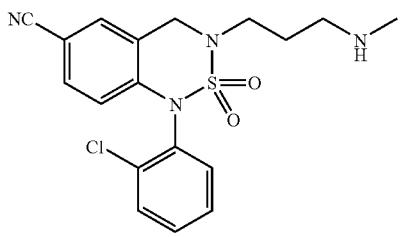

Example 81

4-[6-cyano-1-(2,4,6-trifluorophenyl)-2,2-dioxido-1,4-dihydro-3H-2,1,3-benzothiadiazin-3-yl]-N-methyl-propan-1-amine

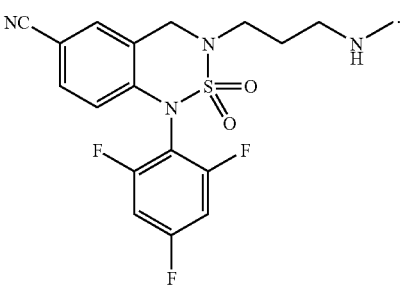

Biological Examples

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 μg/ml G418 (Gibco, Cat. No. 10131). Cells were plated at 300,000 T75 flask and cells were split twice weekly.

Functional Norepinephrine (NE) Uptake Assay

On day 1, cells were plated at 3,000 cells/well in growth medium and maintained in a cell incubator (37° C., 5% $CO_2$). On day 2, growth medium was replaced with 200 μl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 1 μM pargyline. For screening, 25 μl of compound in 4% DMSP was added directly to each well and the plate is incubated for 5 minutes at 37° C.

To initiate the norepinephrine reuptake, 16 nM (final concentration) of $^3H$ norepinephrine (specific activity; 40-80 Ci/mmol) in assay buffer was delivered in 25 μl aliquots to each well, and the plates were incubated for 5 minutes at 37° C. The reaction was aspirated from the plate and the cells washed with 250 μl of 50 mM Tris Buffer (4° C.). The plates were left to dry for 1 hour. The cells were lysed using 0.25 M NaOH solution then placed on a shake table and vigorously shaken for 10 minutes. After cell lysis, 100 μl of Microscint 20 (PerkinElmer; #87-051101) were added to the plates and the plates were sealed with film tape and replaced on the shake table for a minimum of 10 minutes. The plates were counted in a TopCount counter (PerkinElmer).

Evaluation of Results

For screening single point determinations, each compound plate contains at least 3 control wells (maximum NE reuptake determinant) and 3 non-specific wells determined by adding 20 μM of desipramine (minimum NE reuptake determinant). Determination of active compounds are calculated using a Microsoft Excel spread sheet applying the following formula:

% inhibition=[1−((mean cpm test compound wells−mean cpm non-specific wells)/(mean cpm control wells−mean cpm non-specific wells))]×100

For $IC_{50}$ determination, raw cpm values were generated in a data file from the TopCount counter. The data was organized in Microsoft Excel and transferred into PRIZM graphing and statistical program, which calculates the estimated $IC_{50}$ value. Calculation of $IC_{50}$ values were made using non-linear regression analysis with a sigmoidal dose response with variable slope. The statistical program used wells containing $^3H$ norepinephrine only as the maximal NE reuptake determinant and wells containing $^3H$ norepinephrine plus 20 μM desipramine as the minimal NE reuptake determinant (non-specific determinant). Estimation of the $IC_{50}$ value was completed on a log scale and the line was fit between the maximal and minimal NE reuptake values. In the event that the highest test concentration does not exceed 50% reuptake inhibition, data will be reported as percent maximal NE reuptake at the highest concentration tested. The results are reported in Table 1.

TABLE 1

| Example | hNET Uptake IC50 (nM)) |
|---|---|
| 1 | 129 |
| 2 | 628 |
| 3 | 1032 |
| 4 | 792 |
| 5 | 908 |
| 6 | 1503 |

TABLE 1-continued

| Example | hNET Uptake IC50 (nM) |
|---------|----------------------|
| 7 | 492 |
| 8 | 135 |
| 9 | 3552 |
| 10 | 973 |
| 11 | 200 |
| 12 | 2375 |
| 13 | 29 |
| 14 | 956 |
| 15 | 38 |
| 16 | 139 |
| 17 | 1410 |
| 18 | 2871 |
| 19 | 119 |
| 20 | 1745 |
| 21 | 30 |
| 22 | 177 |
| 23 | 81 |
| 24 | 95 |
| 25 | 47% at 10 uM |
| 26 | 36% inhibition at 10 uM |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

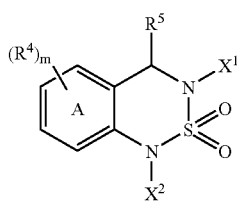

I or a pharmaceutically acceptable salt, tautomer or stereoisomer thereof;
wherein:
n is an integer from 1 to 3
m is an integer from 0 to 4;
$X^1$ is $R^1$ and $X^2$ is W; or
$X^1$ is W and $X^2$ is $R^1$;
W is:

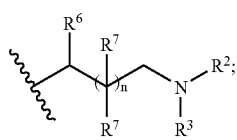

$R^1$ is $C_6$-$C_{10}$ aryl substituted with 0-3 $R^{11}$ or heteroaryl substituted with 0-3 $R^{11}$;

$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;

$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or $R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;

$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;

$R^5$ is H, $C_1$-$C_6$ alkyl, $C_6$-$C_{10}$ aryl substituted with 0-3 $R^{15}$, $C_6$-$C_{10}$ aryl-$C_1$-$C_6$ alkyl where said aryl portion is substituted with 0-3 $R^{15}$, heteroaryl substituted with 0-3 $R^{15}$, or heteroaryl-$C_1$-$C_6$ alkyl where said heteroaryl portion is substituted with 0-3 $R^{15}$;

$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N.

2. The compound of claim 1, wherein:
n is an integer from 1 to 2.

3. The compound of claim 1, wherein:
m is an integer from 0 to 1.

4. The compound of claim 1, wherein:
$R^1$ is $C_6$-$C_{10}$ aryl substituted with 0-3 $R^{11}$.

5. The compound of claim 1, wherein:
$R^1$ is phenyl, tolyl, xylyl, methoxy-phenyl, fluoro-phenyl, difluoro-phenyl, trifluoro-phenyl, chloro-phenyl, fluoro-chloro-phenyl, bromo-phenyl, trifluoromethyl-phenyl trifluoromethoxy-phenyl, methyl-fluoro-phenyl, methoxy-fluoro-phenyl, or naphthyl.

6. The compound of claim 1, wherein:
$R^1$ is heteroaryl substituted with 0-3 $R^1$.
7. The compound of claim 1, wherein:
$R^1$ is pyridinyl, methyl-pyridinyl, ethyl-pyridinyl, methoxy-pyridinyl, or quinolinyl.
8. The compound of claim 1, wherein:
$R^2$ is H, methyl, ethyl, cyclopropyl, or n-butyl.
9. The compound of claim 1, wherein:
$R^2$ is hydrogen or methyl.
10. The compound of claim 1, wherein:
$R^3$ is H, methyl, ethyl, cyclopropyl, or n-butyl.
11. The compound of claim 1, wherein:
$R^3$ is hydrogen or methyl.
12. The compound of claim 1, wherein:
$R^2$ and $R^3$, together with the nitrogen through which they are attached, form a heterocyclic ring of 6 ring atoms, where one carbon may be optionally replaced with O.
13. The compound of claim 1, wherein:
$R^4$ is, independently at each occurrence, $C_1$-$C_6$ alkyl, $C_1$-$C_6$ alkoxy, halo, $CF_3$, $OCF_3$, nitrile, or $C_6$-$C_{10}$ aryl substituted with 0-3 $R^1$.
14. The compound of claim 1, wherein:
$R^4$ is, independently at each occurrence, methyl, methoxy, fluoro, chloro, bromo, $CF_3$, $OCF_3$, nitrile, or phenyl.
15. The compound of claim 1, wherein:
$R^5$ is H, $C_1$-$C_6$ alkyl, or phenyl.
16. The compound of claim 1, wherein:
$R^5$ is H or methyl.
17. The compound of claim 1, wherein:
$R^6$ is H, $C_1$-$C_6$ alkyl, or phenyl.
18. The compound of claim 1, wherein:
$R^6$ is H or methyl.
19. The compound of claim 1, wherein $X^1$ is W and $X^2$ is $R^1$.
20. The compound of claim 1, wherein $X^1$ is $R^1$ and $X^2$ is W.
21. The compound of claim 1, selected from the group consisting of:
3-(2,2-dioxido-1-phenyl-1,4-dihydro-3H-2,1,3-benzothiadiazin-3-yl)-N-methylpropan-1-amine;
3-[1-(3-fluorophenyl)-2,2-dioxido-1,4-dihydro-3H-2,1,3-benzothiadiazin-3-yl]-N-methylpropan-1-amine;
N-methyl-3-[1-(3-methylphenyl)-2,2-dioxido-1,4-dihydro-3H-2,1,3-benzothiadiazin-3-yl]propan-1-amine;
3-[1-(3-methoxyphenyl)-2,2-dioxido-1,4-dihydro-3H-2,1,3-benzothiadiazin-3-yl]-N-methylpropan-1-amine;
3-[1-(4-chlorophenyl)-2,2-dioxido-1,4-dihydro-3H-2,1,3-benzothiadiazin-3-yl]-N-methylpropan-1-amine;
3-[1-(3-chloro-4-fluorophenyl)-2,2-dioxido-1,4-dihydro-3H-2,1,3-benzothiadiazin-3-yl]-N-methylpropan-1-amine;
3-[1-(4-fluorophenyl)-2,2-dioxido-1,4-dihydro-3H-2,1,3-benzothiadiazin-3-yl]-N-methylpropan-1-amine;
N-methyl-3-[1-(4-methylphenyl)-2,2-dioxido-1,4-dihydro-3H-2,1,3-benzothiadiazin-3-yl]propan-1-amine;
3-[1-(4-methoxyphenyl)-2,2-dioxido-1,4-dihydro-3H-2,1,3-benzothiadiazin-3-yl]-N-methylpropan-1-amine;
3-[1-(3,4-difluorophenyl)-2,2-dioxido-1,4-dihydro-3H-2,1,3-benzothiadiazin-3-yl]-N-methylpropan-1-amine;
3-[1-(2-fluorophenyl)-2,2-dioxido-1,4-dihydro-3H-2,1,3-benzothiadiazin-3-yl]-N-methylpropan-1-amine;
N-{3-[1-(2-fluorophenyl)-2,2-dioxido-1,4-dihydro-3H-2,1,3-benzothiadiazin-3-yl]propyl}cyclopropanamine;
4-[1-(2-fluorophenyl)-2,2-dioxido-1,4-dihydro-3H-2,1,3-benzothiadiazin-3-yl]-N-methylbutan-1-amine;
N-{4-[1-(2-fluorophenyl)-2,2-dioxido-1,4-dihydro-3H-2,1,3-benzothiadiazin-3-yl]butyl}cyclopropanamine;
3-[6-fluoro-1-(2-fluorophenyl)-2,2-dioxido-1,4-dihydro-3H-2,1,3-benzothiadiazin-3-yl]-N-methylpropan-1-amine;
N-{3-[6-fluoro-1-(2-fluorophenyl)-2,2-dioxido-1,4-dihydro-3H-2,1,3-benzothiadiazin-3-yl]propyl}cyclopropanamine;
4-[6-fluoro-1-(2-fluorophenyl)-2,2-dioxido-1,4-dihydro-3H-2,1,3-benzothiadiazin-3-yl]-N-methylbutan-1-amine;
N-{4-[6-fluoro-1-(2-fluorophenyl)-2,2-dioxido-1,4-dihydro-3H-2,1,3-benzothiadiazin-3-yl]butyl}cyclopropanamine;
(2S)-4-[6-fluoro-1-(2-fluorophenyl)-2,2-dioxido-1,4-dihydro-3H-2,1,3-benzothiadiazin-3-yl]-1-(methylamino)butan-2-ol;
(2S)-4-[1-(2-fluorophenyl)-2,2-dioxido-1,4-dihydro-3H-2,1,3-benzothiadiazin-3-yl]-1-(methylamino)butan-2-ol;
3-[3-(2-fluorophenyl)-2,2-dioxido-3,4-dihydro-1H-2,1,3-benzothiadiazin-1-yl]-N-methylpropan-1-amine;
4-[1-phenyl-2,2-dioxido-1,4-dihydro-3H-2,1,3-benzothiadiazin-3-yl]-N-methylbutan-1-amine;
4-[1-(2,6-difluorophenyl)-2,2-dioxido-1,4-dihydro-3H-2,1,3-benzothiadiazin-3-yl]-N-methylbutan-1-amine;
4-[1-(2-fluoro-4-methylphenyl)-2,2-dioxido-1,4-dihydro-3H-2,1,3-benzothiadiazin-3-yl]-N-methylbutan-1-amine;
4-[1-(2-chlorophenyl)-2,2-dioxido-1,4-dihydro-3H-2,1,3-benzothiadiazin-3-yl]-N-methylbutan-1-amine;
4-[1-(2,4,6-trifluorophenyl)-2,2-dioxido-1,4-dihydro-3H-2,1,3-benzothiadiazin-3-yl]-N-methylbutan-1-amine;
4-[6-fluoro-1-phenyl-2,2-dioxido-1,4-dihydro-3H-2,1,3-benzothiadiazin-3-yl]-N-methylbutan-1-amine;
4-[6-fluoro-1-(2,6-difluorophenyl)-2,2-dioxido-1,4-dihydro-3H-2,1,3-benzothiadiazin-3-yl]-N-methylbutan-1-amine;
4-[6-fluoro-1-(2-chlorophenyl)-2,2-dioxido-1,4-dihydro-3H-2,1,3-benzothiadiazin-3-yl]-N-methylbutan-1-amine;
4-[6-fluoro-1-(2-fluoro-4-methylphenyl)-2,2-dioxido-1,4-dihydro-3H-2,1,3-benzothiadiazin-3-yl]-N-methylbutan-1-amine;
4-[6-fluoro-1-(2,4,6-trifluorophenyl)-2,2-dioxido-1,4-dihydro-3H-2,1,3-benzothiadiazin-3-yl]-N-methylbutan-1-amine;
4-[6-chloro-1-phenyl-2,2-dioxido-1,4-dihydro-3H-2,1,3-benzothiadiazin-3-yl]-N-methylbutan-1-amine;
4-[6-chloro-1-(2-fluorophenyl)-2,2-dioxido-1,4-dihydro-3H-2,1,3-benzothiadiazin-3-yl]-N-methylbutan-1-amine;
4-[6-chloro-1-(2,6-difluorophenyl)-2,2-dioxido-1,4-dihydro-3H-2,1,3-benzothiadiazin-3-yl]-N-methylbutan-1-amine;
4-[6-chloro-1-(2-fluoro-4-methylphenyl)-2,2-dioxido-1,4-dihydro-3H-2,1,3-benzothiadiazin-3-yl]-N-methylbutan-1-amine;
4-[6-chloro-1-(2-chlorophenyl)-2,2-dioxido-1,4-dihydro-3H-2,1,3-benzothiadiazin-3-yl]-N-methylbutan-1-amine;
4-[6-chloro-1-(2,4,6-trifluorophenyl)-2,2-dioxido-1,4-dihydro-3H-2,1,3-benzothiadiazin-3-yl]-N-methylbutan-1-amine;
4-[6-methyl-1-phenyl-2,2-dioxido-1,4-dihydro-3H-2,1,3-benzothiadiazin-3-yl]-N-methylbutan-1-amine;
4-[6-methyl-1-(2-fluorophenyl)-2,2-dioxido-1,4-dihydro-3H-2,1,3-benzothiadiazin-3-yl]-N-methylbutan-1-amine;

4-[6-methyl-1-(2,6-difluorophenyl)-2,2-dioxido-1,4-dihydro-3H-2,1,3-benzothiadiazin-3-yl]-N-methylbutan-1-amine;
4-[6-methyl-1-(2-fluoro-4-methylphenyl)-2,2-dioxido-1,4-dihydro-3H-2,1,3-benzothiadiazin-3-yl]-N-methylbutan-1-amine;
4-[6-methyl-1-(2-chlorophenyl)-2,2-dioxido-1,4-dihydro-3H-2,1,3-benzothiadiazin-3-yl]-N-methylbutan-1-amine;
4-[6-methyl-1-(2,4,6-trifluorophenyl)-2,2-dioxido-1,4-dihydro-3H-2,1,3-benzothiadiazin-3-yl]-N-methylbutan-1-amine;
4-[6-cyano-1-phenyl-2,2-dioxido-1,4-dihydro-3H-2,1,3-benzothiadiazin-3-yl]-N-methylbutan-1-amine;
4-[6-cyano-1-(2-fluorophenyl)-2,2-dioxido-1,4-dihydro-3H-2,1,3-benzothiadiazin-3-yl]-N-methylbutan-1-amine;
4-[6-cyano-1-(2,6-difluorophenyl)-2,2-dioxido-1,4-dihydro-3H-2,1,3-benzothiadiazin-3-yl]-N-methylbutan-1-amine;
4-[6-cyano-1-(2-fluoro-4-methylphenyl)-2,2-dioxido-1,4-dihydro-3H-2,1,3-benzothiadiazin-3-yl]-N-methylbutan-1-amine;
4-[6-cyano-1-(2-chlorophenyl)-2,2-dioxido-1,4-dihydro-3H-2,1,3-benzothiadiazin-3-yl]-N-methylbutan-1-amine;
4-[6-cyano-1-(2,4,6-trifluorophenyl)-2,2-dioxido-1,4-dihydro-3H-2,1,3-benzothiadiazin-3-yl]-N-methylbutan-1-amine;
4-[1-(2,6-difluorophenyl)-2,2-dioxido-1,4-dihydro-3H-2,1,3-benzothiadiazin-3-yl]-N-methylpropan-1-amine;
4-[1-(2-fluoro-4-methylphenyl)-2,2-dioxido-1,4-dihydro-3H-2,1,3-benzothiadiazin-3-yl]-N-methylpropan-1-amine;
4-[1-(2-chlorophenyl)-2,2-dioxido-1,4-dihydro-3H-2,1,3-benzothiadiazin-3-yl]-N-methylpropan-1-amine;
4-[1-(2,4,6-trifluorophenyl)-2,2-dioxido-1,4-dihydro-3H-2,1,3-benzothiadiazin-3-yl]-N-methylpropan-1-amine;
4-[6-fluoro-1-phenyl-2,2-dioxido-1,4-dihydro-3H-2,1,3-benzothiadiazin-3-yl]-N-methylpropan-1-amine;
4-[6-fluoro-1-(2,6-difluorophenyl)-2,2-dioxido-1,4-dihydro-3H-2,1,3-benzothiadiazin-3-yl]-N-methylpropan-1-amine;
4-[6-fluoro-1-(2-fluoro-4-methylphenyl)-2,2-dioxido-1,4-dihydro-3H-2,1,3-benzothiadiazin-3-yl]-N-methylpropan-1-amine;
4-[6-fluoro-1-(2-chlorophenyl)-2,2-dioxido-1,4-dihydro-3H-2,1,3-benzothiadiazin-3-yl]-N-methylpropan-1-amine;
4-[6-fluoro-1-(2,4,6-trifluorophenyl)-2,2-dioxido-1,4-dihydro-3H-2,1,3-benzothiadiazin-3-yl]-N-methylpropan-1-amine;
4-[6-chloro-1-phenyl-2,2-dioxido-1,4-dihydro-3H-2,1,3-benzothiadiazin-3-yl]-N-methylpropan-1-amine;
4-[6-chloro-1-(2-fluorophenyl)-2,2-dioxido-1,4-dihydro-3H-2,1,3-benzothiadiazin-3-yl]-N-methylpropan-1-amine;
4-[6-chloro-1-(2,6-difluorophenyl)-2,2-dioxido-1,4-dihydro-3H-2,1,3-benzothiadiazin-3-yl]-N-methylpropan-1-amine;
4-[6-chloro-1-(2-fluoro-4-methylphenyl)-2,2-dioxido-1,4-dihydro-3H-2,1,3-benzothiadiazin-3-yl]-N-methylpropan-1-amine;
4-[6-chloro-1-(2-chlorophenyl)-2,2-dioxido-1,4-dihydro-3H-2,1,3-benzothiadiazin-3-yl]-N-methylpropan-1-amine;
4-[6-chloro-1-(2,4,6-trifluorophenyl)-2,2-dioxido-1,4-dihydro-3H-2,1,3-benzothiadiazin-3-yl]-N-methylpropan-1-amine;
4-[6-methyl-1-phenyl-2,2-dioxido-1,4-dihydro-3H-2,1,3-benzothiadiazin-3-yl]-N-methylpropan-1-amine;
4-[6-methyl-1-(2-fluorophenyl)-2,2-dioxido-1,4-dihydro-3H-2,1,3-benzothiadiazin-3-yl]-N-methylpropan-1-amine;
4-[6-methyl-1-(2,6-difluorophenyl)-2,2-dioxido-1,4-dihydro-3H-2,1,3-benzothiadiazin-3-yl]-N-methylpropan-1-amine;
4-[6-methyl-1-(2-fluoro-4-methylphenyl)-2,2-dioxido-1,4-dihydro-3H-2,1,3-benzothiadiazin-3-yl]-N-methylpropan-1-amine;
4-[6-methyl-1-(2-chlorophenyl)-2,2-dioxido-1,4-dihydro-3H-2,1,3-benzothiadiazin-3-yl]-N-methylpropan-1-amine;
4-[6-methyl-1-(2,4,6-trifluorophenyl)-2,2-dioxido-1,4-dihydro-3H-2,1,3-benzothiadiazin-3-yl]-N-methylpropan-1-amine;
4-[6-cyano-1-phenyl-2,2-dioxido-1,4-dihydro-3H-2,1,3-benzothiadiazin-3-yl]-N-methylpropan-1-amine;
4-[6-cyano-1-(2-fluorophenyl)-2,2-dioxido-1,4-dihydro-3H-2,1,3-benzothiadiazin-3-yl]-N-methylpropan-1-amine;
4-[6-cyano-1-(2,6-difluorophenyl)-2,2-dioxido-1,4-dihydro-3H-2,1,3-benzothiadiazin-3-yl]-N-methylpropan-1-amine;
4-[6-cyano-1-(2-fluoro-4-methylphenyl)-2,2-dioxido-1,4-dihydro-3H-2,1,3-benzothiadiazin-3-yl]-N-methylpropan-1-amine;
4-[6-cyano-1-(2-chlorophenyl)-2,2-dioxido-1,4-dihydro-3H-2,1,3-benzothiadiazin-3-yl]-N-methylpropan-1-amine;
4-[6-cyano-1-(2,4,6-trifluorophenyl)-2,2-dioxido-1,4-dihydro-3H-2,1,3-benzothiadiazin-3-yl]-N-methylpropan-1-amine; and
pharmaceutically acceptable salts thereof.

22. The compound of claim 1, wherein said pharmaceutically acceptable salt is a hydrochloride.

23. A composition, comprising:
a. at least one compound of formula I:

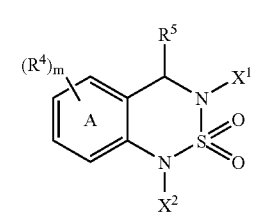

or a pharmaceutically acceptable salt, tautomer or stereoisomer thereof;
wherein:
n is an integer from 1 to 3
m is an integer from 0 to 4;
$X^1$ is $R^1$ and $X^2$ is W; or
$X^1$ is W and $X^2$ is $R^1$;

W is:

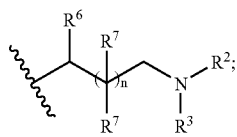

R$^1$ is C$_6$-C$_{10}$ aryl substituted with 0-3 R$^{11}$ or heteroaryl substituted with 0-3 R$^{11}$;

R$^2$ is H, C$_1$-C$_6$ alkyl, C$_3$-C$_6$ cycloalkyl, C$_2$-C$_6$ alkanol, or C$_6$-C$_{10}$ aryl-C$_1$-C$_6$ alkyl, where said aryl portion is substituted with 0-3 R$^{12}$ and said alkyl portions may be substituted with 0-3 R$^{13}$;

R$^3$ is H, C$_1$-C$_6$ alkyl, C$_3$-C$_6$ cycloalkyl, C$_2$-C$_6$ alkanol or C$_6$-C$_{10}$ aryl-C$_1$-C$_6$ alkyl, where said aryl portion is substituted with 0-3 R$^{12}$ and said alkyl portions may be substituted with 0-3 R$^{13}$; or R$^2$ and R$^3$, together with the nitrogen through which they are attached, form a heterocyclic ring or heterobicyclic ring of 3 to 12 ring atoms, where one carbon may be optionally replaced with N, O, S, or SO$_2$, where any carbon ring atom may be optionally substituted with R$^{12}$, and where said additional N atom may be optionally substituted with C$_1$-C$_4$ alkyl;

R$^4$ is, independently at each occurrence, C$_1$-C$_6$ alkyl, C$_1$-C$_6$ alkoxy, halo, CF$_3$, OCF$_3$, hydroxy, alkanoyloxy, nitro, nitrile, C$_2$-C$_6$ alkenyl, C$_2$-C$_6$ alkynyl, C$_6$-C$_{10}$ aryl substituted with 0-3 R$^{14}$, heteroaryl substituted with 0-3 R$^{14}$, alkylsulfoxide, alkylsulfone, alkylsulfonamide, C$_6$-C$_{10}$ arylsulfonamide, alkylamido, or arylamido;

R$^5$ is H, C$_1$-C$_6$ alkyl, C$_6$-C$_{10}$ aryl substituted with 0-3 R$^5$, C$_6$-C$_{10}$ aryl-C$_1$-C$_6$ alkyl where said aryl portion is substituted with 0-3 R$^{15}$, heteroaryl substituted with 0-3 R$^{15}$, or heteroaryl-C$_1$-C$_6$ alkyl where said heteroaryl portion is substituted with 0-3 R$^{15}$;

R$^6$ is H, C$_1$-C$_6$ alkyl, C$_6$-C$_{10}$ aryl substituted with 0-3 R$^{16}$, C$_6$-C$_{10}$ aryl-C$_1$-C$_6$ alkyl, where said aryl portion is substituted with 0-3 R$^{16}$, heteroaryl substituted with 0-3 R$^{16}$, or heteroaryl-C$_1$-C$_6$ alkyl where said heteroaryl portion is substituted with 0-3 R$^{16}$;

R$^7$ is, independently at each occurrence, H, alkyl, C$_1$-C$_6$ alkoxy, halo, CF$_3$, OCF$_3$, hydroxy, alkanoyloxy, nitro, nitrile, C$_2$-C$_6$ alkenyl, C$_2$-C$_6$ alkynyl, alkylsulfoxide, alkylsulfone, alkylsulfonamide, or alkylamido; or R$^7$ and one of said R$^2$ and R$^3$, together with the nitrogen and carbon through which they are attached, may optionally form a heterocyclic or heterobicyclic ring of 3 to 12 ring atoms, where one carbon may be optionally substituted with R$^{13}$ and any additional N atom substituted with C$_1$-C$_4$ alkyl;

R$^{11}$ and R$^{12}$ are, independently at each occurrence, C$_1$-C$_6$ alkyl, C$_1$-C$_6$ alkoxy, halo, CF$_3$, OCF$_3$, hydroxy, alkanoyloxy, nitro, nitrile, C$_2$-C$_6$ alkenyl, C$_2$-C$_6$ alkynyl, C$_6$-C$_{10}$ aryl, heteroaryl, alkylsulfoxide, alkylsulfone, alkylsulfonamide, C$_6$-C$_{10}$ arylsulfonamide, alkylamido, or arylamido;

R$^{13}$, R$^{14}$, R$^{15}$, and R$^{16}$ are, independently at each occurrence, C$_1$-C$_6$ alkyl, C$_1$-C$_6$ alkoxy, halo, CF$_3$, OCF$_3$, hydroxy, alkanoyloxy, nitro, nitrile, C$_2$-C$_6$ alkenyl, or C$_2$-C$_6$ alkynyl; and wherein 1-3 carbon atoms in ring A may optionally be replaced with N; and b. at least one pharmaceutically acceptable carrier.

24. A method for treating a condition selected from the group consisting of a vasomotor symptom, sexual dysfunction, genitourinary disorder, chronic fatigue syndrome, fibromyalgia syndrome, depression disorder, endogenous behavioral disorder, diabetic neuropathy, and pain in a subject in need thereof comprising the step of:

administering to said subject an effective amount of a compound of formula I:

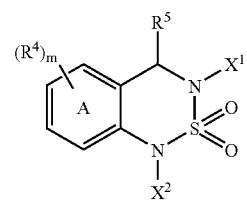

or a pharmaceutically acceptable salt, tautomer or stereoisomer thereof;

wherein:

n is an integer from 1 to 3 m is an integer from 0 to 4;

X$^1$ is R$^1$ and X$^2$ is W; or

X$^1$ is W and X$^2$ is R$^1$;

W is:

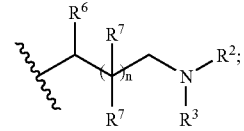

R$^1$ is C$_6$-C$_{10}$ aryl substituted with 0-3 R$^{11}$ or heteroaryl substituted with 0-3 R$^{11}$;

R$^2$ is H, C$_1$-C$_6$ alkyl, C$_3$-C$_6$ cycloalkyl, C$_2$-C$_6$ alkanol, or C$_6$-C$_{10}$ aryl-C$_1$-C$_6$ alkyl, where said aryl portion is substituted with 0-3 R$^{12}$ and said alkyl portions may be substituted with 0-3 R$^{13}$;

R$^3$ is H, C$_1$-C$_6$ alkyl, C$_3$-C$_6$ cycloalkyl, C$_2$-C$_6$ alkanol or C$_6$-C$_{10}$ aryl-C$_1$-C$_6$ alkyl, where said aryl portion is substituted with 0-3 R$^{12}$ and said alkyl portions may be substituted with 0-3 R$^{13}$; or R$^2$ and R$^3$, together with the nitrogen through which they are attached, form a heterocyclic ring or heterobicyclic ring of 3 to 12 ring atoms, where one carbon may be optionally replaced with N, O, S, or SO$_2$, where any carbon ring atom may be optionally substituted with R$^{12}$, and where said additional N atom may be optionally substituted with C$_1$-C$_4$ alkyl;

R$^4$ is, independently at each occurrence, C$_1$-C$_6$ alkyl, C$_1$-C$_6$ alkoxy, halo, CF$_3$, OCF$_3$, hydroxy, alkanoyloxy, nitro, nitrile, C$_2$-C$_6$ alkenyl, C$_2$-C$_6$ alkynyl, C$_6$-C$_{10}$ aryl substituted with 0-3 R$^{14}$, heteroaryl substituted with 0-3 R$^{14}$, alkylsulfoxide, alkylsulfone, alkylsulfonamide, C$_6$-C$_{10}$ arylsulfonamide, alkylamido, or arylamido;

R$^5$ is H, C$_1$-C$_6$ alkyl, C$_6$-C$_{10}$ aryl substituted with 0-3 R$^{15}$, C$_6$-C$_{10}$ aryl-C$_1$-C$_6$ alkyl where said aryl portion is substituted with 0-3 R$^{15}$, heteroaryl substituted with 0-3 R$^{15}$, or heteroaryl-C$_1$-C$_6$ alkyl where said heteroaryl portion is substituted with 0-3 R$^{15}$;

R$^6$ is H, C$_1$-C$_6$ alkyl, C$_6$-C$_{10}$ aryl substituted with 0-3 R$^{16}$, C$_6$-C$_{10}$ aryl-C$_1$-C$_6$ alkyl, where said aryl portion is substituted with 0-3 R$^{16}$, heteroaryl substituted with 0-3

$R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N;

or pharmaceutically acceptable salt, tautomer or stereoisomer thereof.

25. The method of claim 24, wherein said vasomotor symptom is hot flush.

26. The method of claim 24, wherein said sexual dysfunction is desire-related or arousal-related.

27. The method of claim 24, wherein said condition is chronic fatigue syndrome.

28. The method of claim 24, wherein said condition is fibromyalgia syndrome.

29. The method of claim 24, wherein said condition is a depression disorder selected from the group consisting of major depressive disorder, generalized anxiety disorder, panic disorder, attention deficit disorder with or without hyperactivity, sleep disturbance, social phobia, and combinations thereof.

30. The method of claim 24, wherein said condition is diabetic neuropathy.

31. The method of claim 24, wherein said condition is pain.

32. The method of claim 31, wherein said pain is acute centralized pain, acute peripheral pain, or a combination thereof.

33. The method of claim 31, wherein said pain is chronic centralized pain, chronic peripheral pain, or a combination thereof.

34. The method of claim 31, wherein said pain is neuropathic pain, visceral pain, musculoskeletal pain, bony pain, cancer pain, inflammatory pain, or a combination thereof.

35. The method of claim 34, wherein said neuropathic pain is associated with diabetes, post traumatic pain of amputation, lower back pain, cancer, chemical injury, toxins, major surgery, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, viral infection, bacterial infection, metastatic infiltration, adiposis dolorosa, burns, central pain conditions related to thalamic conditions, or a combination thereof.

36. The method of claim 35, wherein said neuropathic pain is post-herpetic neuralgia.

37. The method of claim 34, wherein said visceral pain is associated with ulcerative colitis, irritable bowel syndrome, irritable bladder, Crohn's disease, rheumatologic (arthralgias), tumors, gastritis, pancreatitis, infections of the organs, biliary tract disorders, or a combination thereof.

38. The method of claim 31, wherein said pain is female-specific pain.

39. A process for the preparation of a compound of Formula II:

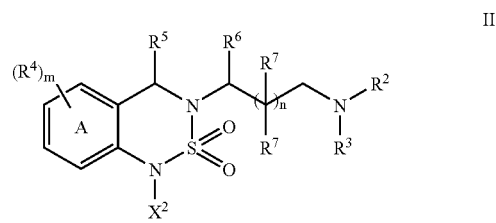

or a pharmaceutically acceptable salt, tautomer or stereoisomer thereof;

wherein:

n is an integer from 1 to 3 m is an integer from 0 to 4;

$R^1$ is $C_6$-$C_{10}$ aryl substituted with 0-3 $R^{11}$ or heteroaryl substituted with 0-3 $R^{11}$;

$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;

$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or $R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;

$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;

$R^5$ is H, $C_1$-$C_6$ alkyl, $C_6$-$C_{10}$ aryl substituted with 0-3 $R^{15}$, $C_6$-$C_{10}$ aryl-$C_1$-$C_6$ alkyl where said aryl portion is substituted with 0-3 $R^{15}$, heteroaryl substituted with 0-3 $R^{15}$, or heteroaryl-$C_1$-$C_6$ alkyl where said heteroaryl portion is substituted with 0-3 $R^{15}$;

$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;

$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or $R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;

$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;

$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and wherein 1-3 carbon atoms in ring A may optionally be replaced with N;

said process comprising:

reacting $G_{a1}$-$R^1$ with a compound of formula IIA:

*[Structure IIA shown]* to form a compound of formula IIB:

*[Structure IIB shown]* wherein, $G_{a1}$ and $G_{a2}$ are independently, activating groups;

$G_{p1}$ is a protecting group;

T is —N($R^2$)($G_{p1}$), $G_{a2}$, or —N($R^2$)($R^3$);

wherein, if T is —N($R^2$)($R^3$), the compound of formula II is formed; or if T is —N($R^2$)($G_{p1}$), the process further comprises:
 deprotecting the compound of formula IIB to form a deprotected compound;
 wherein,
 if $R^3$ in the compound of formula II is H, then the compound of formula II is formed; or
 if $R^3$ is other than H, the process further comprises reacting the deprotected compound with activated-$R^3$,
 wherein the compound of formula II is formed; or if T is $G_{a2}$, the process further comprises:
 reacting the compound of formula IIB with —N($R^2$)($R^3$) to form the compound of formula II; or
 reacting the compound of formula IIB with —N($R^2$)($G_{p1}$) to form a protected compound;
 deprotecting the protected compound to form a deprotected compound;
 wherein,
 if $R^3$ in the compound of formula II is H, then the compound of formula II is formed; or
 if $R^3$ is other than H, the process further comprises reacting the deprotected compound with activated-$R^3$,
 wherein the compound of formula II is formed.

40. The process of claim 39, wherein activated-$R^3$ is halo-$R^3$.

41. The process of claim 39, wherein the compound of formula IIA is formed by:

reacting sulfamide with a compound of formula IIC:

*[Structure IIC shown]* thereby forming a compound of formula IIA.

42. The process of claim 41, wherein the step of reacting sulfamide with a compound of formula IC is performed in the presence of a reducing agent.

43. The process of claim 41, wherein the compound of formula IIC is formed by:

reacting a compound of formula IID:

*[Structure IID shown]* with a compound of formula IIE:

*[Structure IIE shown]* wherein, $G_{a3}$ is an activating group;

thereby forming the compound of formula IIC.

44. The process of claim 43, wherein the activating group is selected from the group consisting of halo, tosylate, mesylate, and triflate.

45. The process of claim 44, wherein the activating group is Cl.

46. The process of claim 39, wherein the protecting group is selected from the group consisting of BOC, benzyl, acetyl, PMB, $C_1$-$C_6$ alkyl, Fmoc, Cbz, trifluoroacetyl, tosyl and triphenylmethyl.

47. The process of claim 46, wherein the protecting group is BOC.

48. The process of claim 39, wherein the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

49. The process of claim 39, wherein any one of the steps is performed at or above 30° C. or any one of the steps includes a purification step comprising at least one of: filtration, extraction, chromatography, trituration, or recrystallization.

50. The process of claim 39, wherein any one of the steps is performed in: a protic solvent, an aprotic solvent, a polar solvent, a nonpolar solvent, a protic polar solvent, an aprotic nonpolar solvent, or an aprotic polar solvent.

51. A process for the preparation of a compound of formula II:

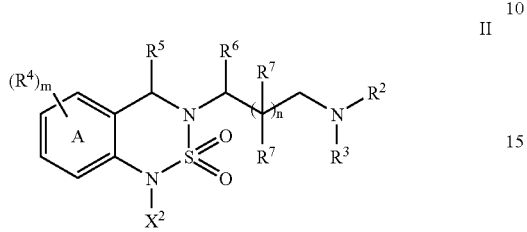

or a pharmaceutically acceptable salt, tautomer or stereoisomer thereof;
wherein:
n is an integer from 1 to 3
m is an integer from 0 to 4;
$R^1$ is $C_6$-$C_{10}$ aryl substituted with 0-3 $R^{11}$ or heteroaryl substituted with 0-3 $R^{11}$;
$R^2$ is H, $C_1$-$C_6$ alkyl, $C_3$-$C_6$ cycloalkyl, $C_2$-$C_6$ alkanol, or $C_6$-$C_{10}$ aryl-$C_1$-$C_6$ alkyl, where said aryl portion is substituted with 0-3 $R^{12}$ and said alkyl portions may be substituted with 0-3 $R^{13}$;
$R^3$ is H, $C_1$-$C_6$ alkyl, $C_3$-$C_6$ cycloalkyl, $C_2$-$C_6$ alkanol or $C_6$-$C_{10}$ aryl-$C_1$-$C_6$ alkyl, where said aryl portion is substituted with 0-3 $R^{12}$ and said alkyl portions may be substituted with 0-3 $R^{13}$; or
$R^2$ and $R^3$, together with the nitrogen through which they are attached, form a heterocyclic ring or heterobicyclic ring of 3 to 12 ring atoms, where one carbon may be optionally replaced with N, O, S, or $SO_2$, where any carbon ring atom may be optionally substituted with $R^{12}$, and where said additional N atom may be optionally substituted with $C_1$-$C_4$ alkyl;
$R^4$ is, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl substituted with 0-3 $R^{14}$, heteroaryl substituted with 0-3 $R^{14}$, alkylsulfoxide, alkylsulfone, alkylsulfonamide, $C_6$-$C_{10}$ arylsulfonamide, alkylamido, or arylamido;
$R^5$ is H;
$R^6$ is H, $C_1$-$C_6$ alkyl, $C_6$-$C_{10}$ aryl substituted with 0-3 $R^{16}$, $C_6$-$C_{10}$ aryl-$C_1$-$C_6$ alkyl, where said aryl portion is substituted with 0-3 $R^{16}$, heteroaryl substituted with 0-3 $R^{16}$, or heteroaryl-$C_1$-$C_6$ alkyl where said heteroaryl portion is substituted with 0-3 $R^{16}$;
$R^7$ is, independently at each occurrence, H, alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, alkylsulfoxide, alkylsulfone, alkylsulfonamide, or alkylamido; or
$R^7$ and one of said $R^2$ and $R^3$, together with the nitrogen and carbon through which they are attached, may optionally form a heterocyclic or heterobicyclic ring of 3 to 12 ring atoms, where one carbon may be optionally substituted with $R^{13}$ and any additional N atom substituted with $C_1$-$C_4$ alkyl;
$R^{11}$ and $R^{12}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, $C_2$-$C_6$ alkynyl, $C_6$-$C_{10}$ aryl, heteroaryl, alkylsulfoxide, alkylsulfone, alkylsulfonamide, $C_6$-$C_{10}$ arylsulfonamide, alkylamido, or arylamido;
$R^{13}$, $R^{14}$, $R^{15}$, and $R^{16}$ are, independently at each occurrence, $C_1$-$C_6$ alkyl, $C_1$-$C_6$ alkoxy, halo, $CF_3$, $OCF_3$, hydroxy, alkanoyloxy, nitro, nitrile, $C_2$-$C_6$ alkenyl, or $C_2$-$C_6$ alkynyl; and
wherein 1-3 carbon atoms in ring A may optionally be replaced with N;
said process comprising:
reacting a compound of formula IIF:

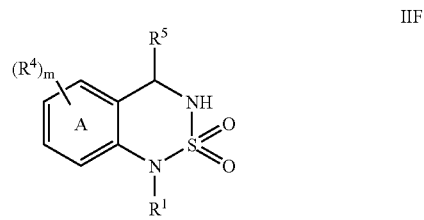

with a compound of formula IIG:

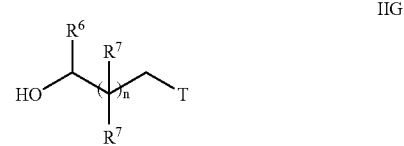

to form a compound of formula IIB:

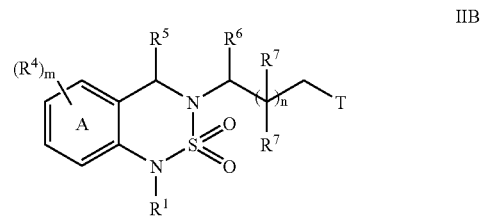

wherein,
T is $—N(R^2)(G_{p1})$, $G_{a2}$, or $—N(R^2)(R^3)$;
wherein,
if T is $—N(R^2)(R^3)$, the compound of formula II is formed;
if T is $—N(R^2)(G_{p1})$, the process further comprises:
deprotecting the compound of formula IIB to form a deprotected compound;
wherein,
if $R^3$ in the compound of formula II is H, then the compound of formula II is formed; or
if $R^3$ is other than H, the process further comprises reacting the deprotected compound with activated-$R^3$,
wherein the compound of formula II is formed; or
if T is $G_{a2}$, the process further comprises:
reacting the compound of formula IIB with $—N(R^2)(R^3)$ to form the compound of formula II; or
reacting the compound of formula IIB with $—N(R^2)(G_{p1})$ to form a protected compound;
deprotecting the protected compound to form a deprotected compound;

wherein,
if $R^3$ in the compound of formula II is H, then the compound of formula II is formed; or
if $R^3$ is other than H, the process further comprises reacting the deprotected compound with activated-$R^3$,
wherein the compound of formula II is formed.

52. The process of claim 51, wherein the reacting step is performed in the presence of dialkyl azodicarboxylate and triphenylphosphine ($PPh_3$).

53. The process of claim 52, wherein the dialkyl azodicarboxylate is diisopropyl azodicarboxylate.

54. The process of claim 51, wherein activated-$R^3$ is halo-$R^3$.

55. The process of claim 51, wherein T is Cl.

56. The process of claim 51, wherein the compound of formula IIF is prepared by:
reacting sulfamide with a compound of formula IIH:

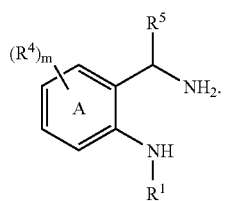

IIH

57. The process of claim 56, wherein the compound of formula IIH is prepared by:
reducing a compound of formula IIJ:

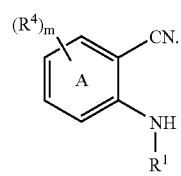

IIJ

58. The process of claim 57, wherein the reducing step comprises contacting the compound of formula IIJ with borane.

59. The process of claim 57, wherein the compound of formula IIJ is prepared by:
reacting $R^1NH_2$ with a compound of formula IIK:

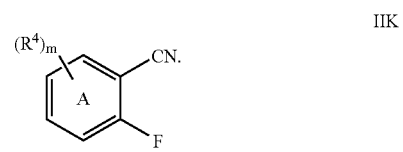

IIK

60. The process of claim 59, wherein the reacting step is performed in the presence of a base.

61. The process of claim 60, wherein the base is potassium tertiary butoxide (KOt-Bu).

62. The process of claim 51, wherein the activating group is selected from the group consisting of halo, tosylate, mesylate, triflate, and oxo.

63. The process of claim 62, wherein the activating group is Br.

64. The process of claim 51, wherein the protecting group is selected from the group consisting of BOC, benzyl, acetyl, PMB, $C_1$-$C_6$ alkyl, Fmoc, Cbz, trifluoroacetyl, tosyl and triphenylmethyl.

65. The process of claim 64, wherein the protecting group is BOC.

66. The process of claim 51, wherein the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

67. The process of claim 51, wherein any one of steps is performed at or above 30° C. or any one of steps further comprises a purification step comprising at least one of: filtration, extraction, chromatography, trituration, or recrystallization.

68. The process of claim 51, wherein any one of the steps is performed in: a protic solvent, an aprotic solvent, a polar solvent, a nonpolar solvent, a protic polar solvent, an aprotic nonpolar solvent, or an aprotic polar solvent.

* * * * *